US008927273B2

(12) United States Patent
Ideno et al.

(10) Patent No.: US 8,927,273 B2
(45) Date of Patent: Jan. 6, 2015

(54) PROCESS FOR PRODUCING CYTOTOXIC LYMPHOCYTES

(75) Inventors: Mitsuko Ideno, Kyoto (JP); Nobuko Muraki, Koka (JP); Kinuko Ogawa, Otsu (JP); Masayuki Kishimoto, Otsu (JP); Tatsuji Enoki, Kyotanabe (JP); Hiroaki Sagawa, Kusatsu (JP); Ikunoshin Kato, Koka (JP)

(73) Assignee: Takara Bio Inc., Otsu-shi (JP)

( * ) Notice: Subject to any disclaimer, the term of this patent is extended or adjusted under 35 U.S.C. 154(b) by 946 days.

(21) Appl. No.: 10/568,745

(22) PCT Filed: Aug. 19, 2004

(86) PCT No.: PCT/JP2004/012238
§ 371 (c)(1),
(2), (4) Date: Feb. 21, 2006

(87) PCT Pub. No.: WO2005/019450
PCT Pub. Date: Mar. 3, 2005

(65) Prior Publication Data
US 2009/0221077 A1    Sep. 3, 2009

(30) Foreign Application Priority Data

| Aug. 22, 2003 | (JP) | 2003-298208 |
| Jan. 5, 2004 | (JP) | 2004-000699 |
| Apr. 9, 2004 | (JP) | 2004-115648 |
| Jul. 29, 2004 | (JP) | 2004-222441 |

(51) Int. Cl.
*C12N 5/07* (2010.01)
*C12N 5/0783* (2010.01)

(52) U.S. Cl.
CPC .......... *C12N 5/0636* (2013.01); *C12N 2501/58* (2013.01)
USPC ........... 435/347; 435/372; 435/373; 435/377; 435/386

(58) Field of Classification Search
None
See application file for complete search history.

(56) References Cited

U.S. PATENT DOCUMENTS

| 5,102,988 A | 4/1992 | Kimizuka et al. |
| 5,198,423 A | 3/1993 | Taguchi et al. |
| 5,354,686 A | 10/1994 | Haberman |
| 5,827,642 A | 10/1998 | Riddell et al. |
| 5,866,115 A | 2/1999 | Kanz et al. |
| 6,287,864 B1 | 9/2001 | Bagnis et al. |
| 6,316,257 B1 | 11/2001 | Flyer et al. |
| 6,472,204 B1 | 10/2002 | Asada et al. |
| 6,692,964 B1 | 2/2004 | June et al. |
| 6,734,014 B1 | 5/2004 | Hwu et al. |
| 6,821,778 B1 | 11/2004 | Engleman et al. |
| 7,067,318 B2 | 6/2006 | June et al. |
| 7,172,869 B2 | 2/2007 | June et al. |
| 2002/0119568 A1 | 8/2002 | Berenson et al. |
| 2003/0022210 A1 | 1/2003 | Bonyhadi et al. |
| 2004/0101519 A1 | 5/2004 | June et al. |
| 2004/0115809 A1 | 6/2004 | Sagawa et al. |
| 2005/0042208 A1 | 2/2005 | Sagawa et al. |
| 2005/0227354 A1 | 10/2005 | Sagawa et al. |
| 2006/0166924 A1 | 7/2006 | Kato et al. |
| 2006/0246587 A1 | 11/2006 | June et al. |
| 2008/0227204 A1 | 9/2008 | Sagawa et al. |

FOREIGN PATENT DOCUMENTS

| EP | 0 207 751 A1 | 1/1987 |
| EP | 0409655 A2 | 1/1991 |
| EP | 0523948 | 1/1993 |
| EP | 0795606 A1 | 9/1997 |
| EP | 0870839 | 10/1998 |
| EP | 1424387 A1 | 6/2004 |
| EP | 1 496 109 A1 | 1/2005 |
| EP | 1666589 A1 | 6/2006 |
| JP | 3-80076 A | 4/1991 |
| JP | 3104178 B2 | 5/1991 |
| JP | 3-284700 A | 12/1991 |
| JP | 4297494 | 10/1992 |
| JP | 5-271291 A | 10/1993 |
| JP | 6-172203 A | 6/1994 |
| JP | 6306096 | 11/1994 |
| JP | 9-25299 A | 1/1997 |
| JP | 10-29952 A | 2/1998 |
| JP | 2729712 | 3/1998 |
| JP | 11505419 | 5/1999 |
| JP | 2001314183 | 11/2001 |
| JP | 2003-80817 A | 3/2003 |
| JP | 2004-500095 A | 1/2004 |
| WO | WO 8802774 A1 * | 4/1988 |
| WO | WO-8901942 | 3/1989 |
| WO | WO-90/13653 A1 | 11/1990 |
| WO | WO-95/04078 A1 | 2/1995 |
| WO | WO-95/11963 A1 | 5/1995 |

(Continued)

OTHER PUBLICATIONS

Lamers et al., Cancer Gene Therapy (2002) 9, 613-623.*
Ochoa et al., Cancer Res. Feb. 15, 1989;49(4):963-8.*
Johnston et al., Experimental Cell Research 201,91-98 (1992).*
Rider et al., J Immunol. Jan. 1, 1988;140(1):200-7.*
Sigma product sheet for "1,2-Dioctanoyl-sn-glycerol," 2 pages, downloaded on Mar. 8, 2011 from http://www.sigmaaldrich.com/catalog/ProductDetail.do?D7=0&N5=SEARCH_CONCAT_PNO%7CBRAND_KEY&N4=D5156%7CSIGMA&N25=0&QS=ON&F=SPEC.*

(Continued)

*Primary Examiner* — Zachary Skelding
(74) *Attorney, Agent, or Firm* — Birch, Stewart, Kolasch & Birch, LLP

(57) ABSTRACT

The present invention provides a method for preparing a cytotoxic lymphocyte characterized in that the method comprises the step of carrying out at least one step selected from induction, maintenance and expansion of a cytotoxic lymphocyte using a medium containing serum and plasma at a total concentration of 0% by volume or more and less than 5% by volume, in the presence of fibronectin, a fragment thereof or a mixture thereof.

18 Claims, 1 Drawing Sheet

(56) References Cited

FOREIGN PATENT DOCUMENTS

| WO | WO-9528479 | 10/1995 |
|---|---|---|
| WO | WO-96/00782 A1 | 1/1996 |
| WO | WO 96/06929 A2 | 3/1996 |
| WO | WO-9606929 | 3/1996 |
| WO | WO-9616674 | 6/1996 |
| WO | WO 97/01194 A1 | 1/1997 |
| WO | WO-9705239 | 2/1997 |
| WO | WO-9711604 | 3/1997 |
| WO | WO 97/11694 A1 | 4/1997 |
| WO | WO-9718318 | 5/1997 |
| WO | WO 97/32970 A1 | 9/1997 |
| WO | WO-9812306 | 3/1998 |
| WO | WO-9833888 | 8/1998 |
| WO | WO 99/05301 | 2/1999 |
| WO | WO 99/33863 A1 | 7/1999 |
| WO | WO-9933869 | 7/1999 |
| WO | WO 00/09168 A1 | 2/2000 |
| WO | WO-00/56368 A1 | 9/2000 |
| WO | WO 01/62895 A2 | 8/2001 |
| WO | WO 02/14481 A1 | 2/2002 |
| WO | WO-03/016511 A1 | 2/2003 |
| WO | WO 03/080817 A1 | 2/2003 |
| WO | WO-03/080817 A1 | 10/2003 |
| WO | WO 2004-018667 A1 | 3/2004 |
| WO | WO 2005/019450 A1 | 3/2005 |

OTHER PUBLICATIONS

Gallagher et al., Clin. exp. Immunol. (1988) 74, 166-170.*
Parhar et al., Eur Cytokine Netw. May-Jun. 1992;3(3):299-306.*
Mazumder et al., Cancer. Feb. 15, 1984;53(4):896-905.*
Wolf et al., Vox Sang. May 2005;88(4):249-55.*
Parker et al., Hum Gene Ther. Nov. 20, 2000;11(17):2377-87.*
Gibco/Invitrogen Publication "A Guide to Serum-Free Cell Culture," 2003, pp. 1-7.*
Kaldjian et al. J Immunol Methods. Mar. 4, 1992;147(2):189-95.*
Li et al. (J Immunother. Mar. 1997;20(2):123-30).*
"Animal Cell Culture," Freshney, Ed., 1986, IRL Press; Oxford, Washington DC, pp. 27-40.
"Animal Cell Culture," Freshney, Ed., 1986, IRL Press, Oxford, Washington DC, Sections 2.1,3.2.2-3.2.6,5,6.1-6.3,3.1-3.4.
Proc. Natl. Acad. Sci., USA, vol. 80, No. 16, pp. 3218 to 3222 (1983).
Eur. J. Immunol. vol. 21, pp. 1559 to 1562. (1991).
Cell Immunol., vol. 135, No. 1, pp. 105 to 117 (1991).
"Animal Cell Culture: A Practical Approach", Edited by R.I. Freshney, Moscow, 1989, pp. 44, 53, 77.
Advisory Action for U.S. Appl. No. 10/509,055, dated Jun. 9, 2009.
Advisory Action for U.S. Appl. No. 11/790,025, dated Apr. 2, 2010.
Azuma et al., "Functional Expression of B7/BB1 on Activated T Lymphocytes", J. Exp. Med., vol. 177, Mar. 1993, pp. 845-850.
Blue et al. "Enhancement of CD2-Mediated T Cell Activation by the Interactioin of VLA-4 with Fibronectin", Cellular Immunology, vol. 138, 1991, pp. 238-244.
Board of Patent Appeals and Interferences Decision—Examiner Reversed for U.S. Appl. No. 10/344,534, dated May 28, 2010.
Chinese Office Action for Application No. 200480024172.7, dated Jan. 15, 2010.
Communication from USPTO regarding Information Disclosure Statement for U.S. Appl. No. 10/344,534, dated Jul. 23, 2009.
Examiner Interview Summary for U.S. Appl. No. 10/344,534, dated Feb. 5, 2008.
Examiner Interview Summary for U.S. Appl. No. 10/344,534, dated Jun. 4, 2008.
Examiner Interview Summary for U.S. Appl. No. 10/486,512, dated Aug. 2, 2007.
Extended European Search Report, Application No. EP 09004189. 8-1222/2070542, Dec. 8, 2009, 6 pages.
Johnson et al, "Expression and Function of Insulin-Like Growth Factor Receptors on Anti-CD3-Activated Human T Lymphyocytes", Journal of Immunology, vol. 148, No. 1, Jan. 1, 1992, pp. 63-71.
Jung et al., "Induction of Cytotoxicity in Human Peripheral Blood Mononuclear Cells by Monoclonal Antibody OKT3", Journal of Immunology, vol. 139, No. 2, Jul. 15, 1987, pp. 639-644.
Kanto et at, "Neutralization of Transforming Growth Factor β-1 Augments Hepatitis C Virus-Specific Cytotoxic T Lymphocyte Induction In Vitro", Journal of Clinical Immunology, vol. 17, No. 6, 1997, pp. 462-471.
Katzman et al., "Fibronectin and Cellular Cytotoxicity: Evidence Against a Role for Fibronectin in Natural Killer Activity", J. Lab. Clin. Med., vol. 110, No. 1, Jul. 1987, pp. 75-82.
Lucivero et al., "Functional Characteristics of Cord Blood T Lymphocytes After Lectin and Anti-CD3 Stimulation", Int. J. Clin. Lab. Res., vol. 26, 1996, pp. 255-261.
Neri et al., "Calcein-Acetyoxymethyl Cytotoxicity Assay: Standardization of a Method Allowing Additional Analyses on Recovered Effector Cells and Supernatants", Clin. and Diag. Lab. Immunol., vol. 8, No. 6, Nov. 2001, pp. 1131-1135.
Partial European Search Report, Application No. 09004189.8-1222/ 2070542, Aug. 3, 2009, 3 pages.
Pawelec et al., "Extrathymic T Cell Differentiation in Vitro From Human CD34+ Stem Cells", Journal of Leukocyte Biology, vol. 64, Dec. 1998, pp. 733-739.
Tamura et al., "Expression and Function of c-Met, a Receptor for Hepatocyte Growth Factor, During T-Cell Development", Scandinavian Journal of Immunology, 1998, vol. 47, pp. 296-301.
US Office Action for U.S. Appl. No. 10/486,512, dated Apr. 19, 2010.
US Office Action for U.S. Appl. No. 10/486,512, dated Jun. 23, 2009.
US Office Action for U.S. Appl. No. 10/486,512, dated Sep. 30, 2009.
US Office Action for U.S. Appl. No. 10/509,055, dated Apr. 14, 2010.
US Office Action for U.S. Appl. No. 10/509,055, dated Sep. 3, 2009.
US Office Action for U.S. Appl. No. 11/790,025, dated Dec. 18, 2009.
US Office Action for U.S. Appl. No. 11/790,025, dated May 7, 2009.
US Office Action for U.S. Appl. No. 11/831,423, dated Mar. 18, 2010.
US Office Action for U.S. Appl. No. 11/831,423, dated May 27, 2009.
US Office Action for U.S. Appl. No. 11/831,423, dated Nov. 4, 2009.
Office Action dated Mar. 5, 2010 for Japanese Application No. 2005-513357.
US Office Action, dated Jul. 26, 2010, for U.S. Appl. No. 10/344,534.
US Office Action, dated Jun. 16, 2010, for U.S. Appl. No. 10/344,534.
US Office Action, dated Jun. 7, 2010, for U.S. Appl. No. 11/831,423.
US Office Action, dated Mar. 19, 2007, for U.S. Appl. No. 10/344,534.
US Office Action, dated Nov. 22, 2010, for U.S. Appl. No. 10/486,512.
US Office Action, dated Oct. 22, 2010, for U.S. Appl. No. 10/509,055.
US Office Action, dated Oct. 29, 2010, for U.S. Appl. No. 10/486,512.
"Animal Cell Culture: A Practical Approach", Edited by R.I. Freshney, IRL Press, Oxford, Washington, D.C., 1986, pp. 26-41.
Animal Cell Culture Methods, edited by R. Freshney, Moscow, "MIR", 1989, pp. 44, 53, 77 (the original English "Animal Cell Culture—A Practical Approach"), edited by R.I. Freshney, IRL Press, Oxford, Washington, D.C.
Benigni, Febio et al.; Phenotype and Homing of CD4 Tumor-Specific T Cells is Modulated by Tumor Bulk; The Journal of Immunology; 2005, 175, pp. 739-748.
Dardalhon et al., "Highly efficient gene transfer in naive human T cells with a murine leukemia virus-based vector," Blood, vol. 96, No. 3, 2000, pp. 885-893.
Funaro et al., "Stimulation of T Cells via CD44 Requires Leukocyte-Function-Associated Antigen Interactions and Interleukin-2 Production", Human Immunology, vol. 40, 1994, pp. 267-278.
Gattinoni et al., "Acquisition of full effector function in vitro paradoxically impairs the in vivo antitumor efficacy of adoptively transferred CD8+ T cells," J. Clin. Invest., vol. 115, No. 6, 2005, pp. 1616-1626.
Halvorson et al., "alpha4 and alpha5 integrins costimulate the CD3-dependent proliferation of fetal thymocytes," Cell. Immunol., vol. 189, No. 1, 1998, pp. 1-9.

(56) References Cited

OTHER PUBLICATIONS

Hibino et al., "Tenascin Suppresses CD3-Mediated T Cell Activation", Biochemical and Biophysical Research Communications, vol. 250, 1998, pp. 119-124.
Ideno et al., "RetroNectin® Kumiawaseta T Saibo Kakudai Baiyo (II): Kakudai Baiyo sareta T Saibo Shudan wa NaiveT-yo Saibo no Hiritsu ga Takaku, Takai Kogen Nishikino o Hakki," Dai 65 Kai Annual Meeting of the Japan Cancer Assocation Kiji, 2006, pp. 330.
Ideno et al., "Soshikitai Human Fibronectin Fragment Shigeki ni yoru Kasseika CTL no Tairyo Expansion-ho," Dai 62 Kai Annual Meeting of the Japan Cancer Association Kiji, 2003, pp. 175.
International Search Report in International Application No. PCT/JP02/08298 mailed Dec. 3, 2002.
JPO International Search Report, Appl. No. PCT/JP2006/315881, Oct. 10, 2006.
JPO International Search Report, Appl. No. PCT/JP2006/319105, Jan. 9, 2007.
Kim Young-June et al., "4-1BB Costimulation Promotes Human T Cell Adhesion to Fibronectin", Cellular Immunology 192, 13-23 (1999).
Koberda et al., "Effect of anti-CD3/anti-CD28/interleukin-2 stimulation of mononuclear cells on transforming growth factor B inhibition of lymphokine-activated killer cell generation," J. Cancer Res. Clin. Oncol., vol. 119, 1993, pp. 131-136.
Matsuyama et al., "Activation of CD4 cells by fibronectin and anti-CD3 antibody. A synergistic effect mediated by the VLA-5 fibronectin receptor complex," J. Exp. Med., vol. 170, No. 4, 1989, pp. 1133-1148.
Mosher, Deane F., Fibronectin, Academic Press Inc., 1-24, authored by Deane F. Mosher, published in 1988.
Muraki et al., "Retronectin® Kumiawaseta T Saibo Kakudai Baiyo (I): Kakudai Baiyo ga Anteika shi, NaiveT-yo Saibo ga Kohiritsu de Zoshoku," Dai 65 Kai Annual Meeting of the Japan Cancer Association Kiji, 2006, pp. 330.
Office Action in Chinese Application No. 200480024172.7 mailed Jan. 15, 2010, including English translation.
Office Action in Chinese Application No. 200480024172.7 mailed Nov. 30, 2007, including English translation.
Rao, W. H. et al, "Potent Costimulation of Effector T Lymphocytes by Human Collagen Type I," J Immunol, 2000, vol. 165, pp. 4935-4940.
Retronectin, 2010, Takara Bio. Inc., http://catalog.takara-bio.co.jp/en/PDFFiles/T100A_B_e.pdf.p. 1-8.
Sagawa et al., "Ko-CD3 Kotai to RetroNectin??o Kumiawaseru Koto ni yoru LAK Saibo Inyu Ryoho no Kairyo," Dai 62 Kai Annual Meeting of the Japan Cancer Association Kiji, 2003, pp. 438.
Sekine, "Expansion of Lymphocytes by Culture with Immobilized Anti-CD3 Monoclonal Antibody and Interleukin-2 for Use in Adoptive Immunotherapy of Cancer Patients", Saibo Baiyo (Cell Culture), vol. 17, No. 6, 1991, pp. 192-195.
Shuqin et al., "Induction of Allogenic Cytotoxic T Lymphocytes and Their Culture", Journal of South China Normal University (Natural Science Edition), No. 4, 1994, pp. 11-17 (including partial English language translation).
Simon, Markus M. et al., The outer surface lipoprotein A of *Borrelia burgdorferi* provides direct and indirect augmeting/co-stimulatory signals for the activation of CD4+ and CD8+ T cells, Immunol. Lett., 1995, vol. 46, No. 3, pp. 137-142.
Stohl et al., "Generation of Cytolytic Activity with Anti-CD3 Monoclonal Antibodies Involves Both IL-2-Independent and -Dependent Components", J. Immunol., vol. 144, No. 10, May 15, 1990, pp. 3718-3725.
Sturm, A., et al, "Dual Function of the Extracellular Matrix: Stimulatory for Cell Cycle Progression of Naive T Cells and Antiapoptotic for Tissue-Derived Memory T Cells," The Journal of Immunology, 2004, vol. 173, pp. 3889-3900.
Supplementary European Search Report issued by the EPO in corresponding European Application No. 06782667.7 on Sep. 16, 2009.
Takayama et al., "Adoptive immunotherapy to lower postsurgical recurrence rates of hepatocellular carcinoma: a randomised trial", The Lancet, vol. 356, 2000, pp. 802-807.

US Office Action for U.S. Appl. No. 10/344,534, dated Nov. 6, 2009.
US Office Action for U.S. Appl. No. 10/344,534, mailed May 13, 2008.
US Office Action for U.S. Appl. No. 10/344,534, Nov. 24, 2009.
US Office Action for U.S. Appl. No. 10/486,512, dated Jun. 25, 2004.
US Office Action for U.S. Appl. No. 10/509,055, dated May 11, 2007.
US Office Action for U.S. Appl. No. 10/509,055, mailed Feb. 10, 2011.
US Office Action, dated Aug. 31, 2010, for U.S. Appl. No. 11/990,443.
US Office Action, dated Dec. 28, 2010, for U.S. Appl. No. 11/992,661.
US Office Action, dated Feb. 10, 2011, for U.S. Appl. No. 10/509,055.
US Office Action, dated Jul. 6, 2011, for U.S. Appl. No. 10/509,055.
US Office Action, dated Jun. 9, 2011, for U.S. Appl. No. 11/992,661.
US Office Action, dated Mar. 16, 2011, for U.S. Appl. No. 11/990,443.
US Office Action, dated Oct. 14, 2010, for U.S. Appl. No. 11/992,661.
Whiteside et al., "Isolation of Human NK Cells and Generation of LAK Activity, Current Protocols in Immunology", 1996, Supp. 17, Unit 7.7, pp. 7.7.1-7.7.11.
Williams et al., "Fibronectin and VLA-4 in haematopoietic stem cell-microenvironment interactions," Letters to Nature, vol. 352, 1991, pp. 438-441.
Wills, M. R., et al, "Identification of Naive or Antigen-Experienced Human CD8+ T Cells by Expression of Costimulation and Chemokine Receptors: Analysis of the Human Cytomegalovirus-Specific CD8+ T Cell Response," The Journal of Immunology, 2002, vol. 168, pp. 5455-5464.
Zhou et al., "Molecular Mechanisms Underlying Differential Contribution of CD28 Versus Non-CD28 Costimulatory Molecules to IL-2 Promoter Activation," The Journal of Immunology, vol. 168, 2002, pp. 3847-3854.
United States Office Action for copending U.S. Appl. No. 11/992,661 dated Jul. 12, 2013.
Canadian Office Action for Application No. 2,479,288 dated Feb. 28, 2012.
Ochoa et al., "Long-Term Growth of Lymphokine-Activated Killer (LAK) Cells: Role of Anti-CD3, β-IL 1, Interferon-γ and -β1," The Journal of Immunology, vol. 138, No. 8, Apr. 15, 1987, pp. 2728-2733.
US Office Action for U.S. Appl. No. 10/509,055 dated May 23, 2013.
Japanese Office Action, dated Nov. 14, 2011, for Japanese Application No. 2007-530976 (w/ English translation).
Mikamo, "Bulk Culture of Human Lymphocytes", Cell Technology, 1995, 14:2, 223-227.
Saijou el al., Journal of South China Normal University (Natural Science Edition), No. 4, 1994, pp. 1-17.
Alberto R. Kornblihtt; Proc. Natl. Acad. Sci., USA, vol. 80, No. 16, pp. 3218 to 3222 (1983).
Kazuhisa Takahashi et al.; Eur. J. Immunol. vol. 21, pp. 1559 to 1562. (1991).
Pina M. Cardarelli et al.; Cell Immunol., vol. 135, No. 1, pp. 105 to 117 (1991).
Philip D. Greenberg; Advances in Immunology, vol. 49, pp. 281-355, (1991).
Pierre Reusser et al.; Blood, vol. 78, No. 5, pp. 1373-1380, Sep. 1, 1992.
Steven A. Rosenberg et al.; The New England Journal of Medicine, vol. 316, No. 15, pp. 889-897; Apr. 9, 1987.
Steven A. Rosenberg; The New England Journal of Medicine; vol. 319, No. 25; pp. 1676-1680, Dec. 22, 1988.
Monto Ho et al.; Blood, vol. 81, No. 8, pp. 2093-2101, Apr. 15, 1993.
Stanley R. Riddell et al.; The Journal of Immunology, vol. 146, No. 8, pp. 2795-2804, Apr. 15, 1991.
Stanley R. Riddell et al.; Journal of Immunological Methods, No. 128, pp. 189-201, 1990.
Torben E. Petersen et al.; Primary Structure of Fibronectin; *Fibronectin*; Edited by Deane F. Mosher, pp. 1-24, c. 1989.
Fusao Kimizuka et al.; J. Biochem., No. 110, pp. 284-291, 1991.

(56) References Cited

OTHER PUBLICATIONS

Helmut Hanenberg et al.; Human Gene Therapy, vol. 8, pp. 2193-2206, Dec. 10, 1997.
Shun et al., Zhongguo Haiyang Yaowu Drugs, 14(3); 9-13, 1995.
Mizobata, J. Wakayama Med. Soc., 46, 457-467, (1995).
Ikunoshin Kato et al.; Jpn. J. Phycol.; Mar. 2000, vol. 48, pp. 13-19.
Kohei Noguchi et al.; Anticancer Research, 1995, vol. 15, pp. 255-288.
Maria A. Bednarek et al.; The Journal of Immunology, vol. 147, No. 12, pp. 4047-4053, Dec. 15, 1991.
J. Carter et al.; Immunology 1986, vol. 57, pp. 123-139.
Joseph P. Uberti et al.; Clinical Immunology and Immunopathology, vol. 70, No. 3, Mar. 1994, pp. 234-240.
Galandrini et al.; J. of Immunology, 1994, v. 153, pp. 21-31.
S. Mizobata et al.; British Journal of Cancer, vol. 74, No. 10, pp. 1598-1604, Nov. 1996.
B. Ybarrondo et al.; Immunology, vol. 91, No. 2, pp. 186-192, Jun. 1997.
Yoli Shimizu et al.; Journal of Immunology, vol. 145,, no. pp. 59-67, Jul. 1, 1990.
Gabriella Palmieri et al.; Journal of Immunology, vol. 155, No. 11, pp. 5314-5322, Dec. 1, 1995.
Mark Avdalovic et al.; Immunology Letters, vol. 35, No. 2, pp. 101-108, Feb. 1993.
Laurie S. Davis et al.; Journal of Immunology, vol. 145, No. 3, pp. 785-793, Aug. 1, 1990.
Michael D. Pierschbacher et al.; Cell; vol. 26, No. 2, pp. 259-267, Oct. 1981.
Rao et al., J. Immunol. vol. 165 (2000) pp. 4935-4940.
Nunclon product information, VWRLabshop, p. 1 (Website search date Apr. 19, 2007).
Ostergaard et al. Eur. J. immunol. vol. 25 (1995) pp. 252-256.
Pollok et al., J. Virol. vol. 72 (1998) pp. 4882-4892.
Chen et al., J. Immunol. vol. 153 (1994) pp. 3630-3638.
Yoneda et al., Exp. Cell Res. vol. 217 (1995) pp. 169-179.
Rostagno et al., Biochem J. vol. 338 (1999) pp. 375-386.
Kornblihtt et al., FASEB J., vol. 10 (1996) pp. 248-257.
Galandrini et al., "CD44 Triggering Enhances Human NK Cell Cytotoxic Functions," J. Immunol. vol. 153, pp. 4399-4407 (Nov. 1994) (Abstract Only).
Galandrini et al., "Ligation of the Lymphocyte Homing Receptor CD44 Triggers T-Helper and Cytolytic Functions of Human T-Cells," Cytotechnology, vol. 11, Suppl. 1, pp. S100-S102 (1993) (Abstract Only).
Genetic Medicine, 1999, 32:114-119.
Paul et al., "Long-term growth and cloning of non-transformed lymphocytes," Nature, vol. 294, pp. 697-699, (1981).
Johannes et al. J. Clin. Invest, 1998, V.102, pp. 1051-1061.
Masashi Tani et al., "Gan Tokuiteki Men'eki Ryoho-CTL Ryoho no Genjo to Shorai", Cancer Therapy & Host, 2000, vol. 12, No. 4, p. 330-5, p. 330, lower right part, col. 2.
Seth A. et al., T-cell-receptor-independent activation of cytolytic activity of cytotoxic T lymphocytes mediated through CD44 and gp90MEL-14, Proc. Natl. Acad. Sci. USA, 1991, vol. 88, No. 17, p. 7877-81.
Atsushi Aruga et al.; Biotherapy, 1998, vol. 12, No. 5, pp. 875-877.
Riddell et al. Science 1992, V.257 pp. 238-241.
Galandrini et al.; The Journal of Immunology; vol. 150, pp. 4225-4235, No. 10, May 15, 1993.
Erkki Ruoslahti et al., The Journal of Biological Chemistry; vol. 256, No. 14, Jul. 25, 1981, pp. 7277-7281.
Albert R. Kornblihtt et al.; The EMBO Journal, vol. 4, No. 7, pp. 1755-1759, 1985.
Lehnert et al., Eur. J. Immunol., 1998, vol. 28, pp. 3605-3615.
Pozo et al., The Journal of Cell Biology, 1995, vol. 131, No. 2, pp. 495-508.
Janeway and Travers, 1997, Immunobiology, p. 4:2.
Kiyotoshi Sekiguchi et al., Biochemistry vol. 25, pp. 4936-4941, 1986.
Restriction Office Action from co-pending U.S. Appl. No. 11/831,423 dated Mar. 5, 2009.
Advisory Action from co-pending U.S. Appl. No. 10/509,055 dated May 8, 2009.
Non-Final Office Action from co-pending U.S. Appl. No. 10/509,055 dated Aug. 21, 2008.
Final Office Action from co-pending U.S. Appl. No. 10/509,055 dated Feb. 23, 2009.
Final Office Action from co-pending U.S. Appl. No. 10/509,055 dated Dec. 21, 2007.
Non-Final Office Action from co-pending U.S. Appl. No. 10/509,055 dated May 11, 2007.
Restriction Office Action from co-pending U.S. Appl. No. 10/509,055 dated Jan. 29, 2007.
Final Office Action from co-pending U.S. Appl. No. 10/486,512 dated Jan. 5, 2009.
Final Office Action from co-pending U.S. Appl. No. 10/486,512 dated May 30, 2008.
Non-Final Office Action from co-pending U.S. Appl. No. 10/486,512 dated Oct. 10, 2007.
Final Office Action from co-pending U.S. Appl. No. 10/486,512 dated Feb. 23, 2007.
Restriction Office Action from co-pending U.S. Appl. No. 10/486,512 dated Apr. 24, 2006.
Non-Final Office Action from co-pending U.S. Appl. No. 10/486,512 dated Jul. 25, 2006.
Restriction Office Action from co-pending U.S. Appl. No. 10/344,534 dated Jun. 20, 2005.
Non-Final Office Action from co-pending U.S. Appl. No. 10/344,534 dated Oct. 11, 2005.
Final Office Action from co-pending U.S. Appl. No. 10/344,534 dated Mar. 28, 2006.
Non-Final Office Action from co-pending U.S. Appl. No. 10/344,534 dated Sep. 25, 2006.
Final Office Action from co-pending U.S. Appl. No. 10/344,534 dated May 16, 2007.
Advisory Action from co-pending U.S. Appl. No. 10/344,534 dated Sep. 24, 2007.
Advisory Action from co-pending U.S. Appl. No. 10/344,534 dated Jan. 18, 2008.
Restriction Office Action from co-pending U.S. Appl. No. 11/790,025 dated Jan. 5, 2009.
Yu et al., "The Study of Human LAK and LI-LAK Cells' Proliferation and Activation of Antitumor in Vitro", Journal of Jinan University, Natural Science & Medicine Edition. Dec. 1998. pp. 56-60, vol. 19 Suppl.

\* cited by examiner

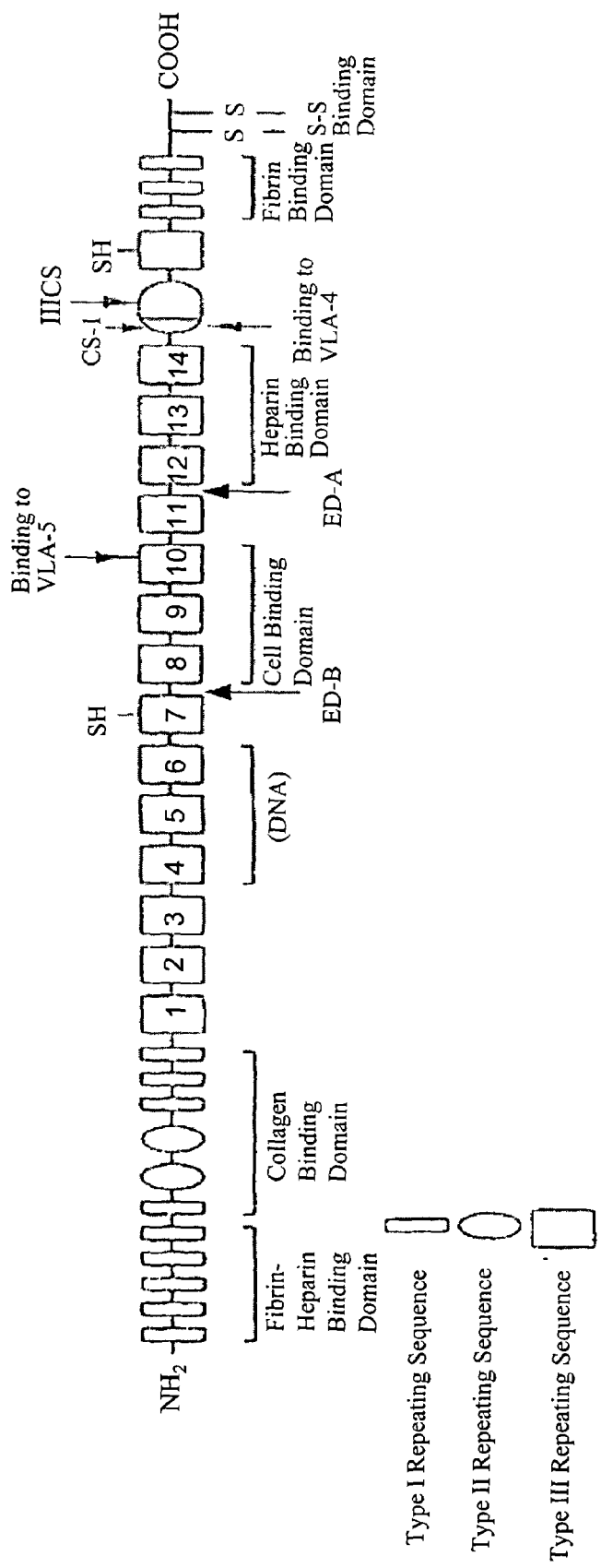

SEQUENCE LISTING

```
<160> NUMBER OF SEQ ID NOS: 30

<210> SEQ ID NO 1
<211> LENGTH: 87
<212> TYPE: PRT
<213> ORGANISM: Artificial Sequence
<220> FEATURE:
<223> OTHER INFORMATION: Chemically synthesized partial region of
      fibronectin named III-8

<400> SEQUENCE: 1

Pro Thr Asp Leu Arg Phe Thr Asn Ile Gly Pro Asp Thr Met Arg Val
1               5                   10                  15

Thr Trp Ala Pro Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr
                85

<210> SEQ ID NO 2
<211> LENGTH: 90
<212> TYPE: PRT
<213> ORGANISM: Artificial Sequence
```

```
<220> FEATURE:
<223> OTHER INFORMATION: Chemically synthesized partial region of
      fibronectin named III-9

<400> SEQUENCE: 2

Gly Leu Asp Ser Pro Thr Gly Ile Asp Phe Ser Asp Ile Thr Ala Asn
1               5                   10                  15

Ser Phe Thr Val His Trp Ile Ala Pro Arg Ala Thr Ile Thr Gly Tyr
            20                  25                  30

Arg Ile Arg His His Pro Glu His Phe Ser Gly Arg Pro Arg Glu Asp
        35                  40                  45

Arg Val Pro His Ser Arg Asn Ser Ile Thr Leu Thr Asn Leu Thr Pro
    50                  55                  60

Gly Thr Glu Tyr Val Val Ser Ile Val Ala Leu Asn Gly Arg Glu Glu
65                  70                  75                  80

Ser Pro Leu Leu Ile Gly Gln Gln Ser Thr
                85                  90

<210> SEQ ID NO 3
<211> LENGTH: 94
<212> TYPE: PRT
<213> ORGANISM: Artificial Sequence
<220> FEATURE:
<223> OTHER INFORMATION: Chemically synthesized partial region of
      fibronectin named III-10

<400> SEQUENCE: 3

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 4
<211> LENGTH: 84
<212> TYPE: PRT
<213> ORGANISM: Artificial Sequence
<220> FEATURE:
<223> OTHER INFORMATION: Chemically synthesized partial region of
      fibronectin named III-11

<400> SEQUENCE: 4

Gln Met Gln Val Thr Asp Val Gln Asp Asn Ser Ile Ser Val Lys Trp
1               5                   10                  15

Leu Pro Ser Ser Ser Pro Val Thr Gly Tyr Arg Val Thr Thr Thr Pro
            20                  25                  30

Lys Asn Gly Pro Gly Pro Thr Lys Thr Lys Thr Ala Gly Pro Asp Gln
        35                  40                  45

Thr Glu Met Thr Ile Glu Gly Leu Gln Pro Thr Val Glu Tyr Val Val
    50                  55                  60
```

Ser Val Tyr Ala Gln Asn Pro Ser Gly Glu Ser Gln Pro Leu Val Gln
 65                  70                  75                  80

Thr Ala Val Thr

<210> SEQ ID NO 5
<211> LENGTH: 92
<212> TYPE: PRT
<213> ORGANISM: Artificial Sequence
<220> FEATURE:
<223> OTHER INFORMATION: Chemically synthesized partial region of
      fibronectin named III-12

<400> SEQUENCE: 5

Ala Ile Pro Ala Pro Thr Asp Leu Lys Phe Thr Gln Val Thr Pro Thr
 1               5                  10                  15

Ser Leu Ser Ala Gln Trp Thr Pro Pro Asn Val Gln Leu Thr Gly Tyr
             20                  25                  30

Arg Val Arg Val Thr Pro Lys Glu Lys Thr Gly Pro Met Lys Glu Ile
         35                  40                  45

Asn Leu Ala Pro Asp Ser Ser Ser Val Val Val Ser Gly Leu Met Val
     50                  55                  60

Ala Thr Lys Tyr Glu Val Ser Val Tyr Ala Leu Lys Asp Thr Leu Thr
 65                  70                  75                  80

Ser Arg Pro Ala Gln Gly Val Val Thr Thr Leu Glu
             85                  90

<210> SEQ ID NO 6
<211> LENGTH: 89
<212> TYPE: PRT
<213> ORGANISM: Artificial Sequence
<220> FEATURE:
<223> OTHER INFORMATION: Chemically synthesized partial region of
      fibronectin named III-13

<400> SEQUENCE: 6

Asn Val Ser Pro Pro Arg Arg Ala Arg Val Thr Asp Ala Thr Glu Thr
 1               5                  10                  15

Thr Ile Thr Ile Ser Trp Arg Thr Lys Thr Glu Thr Ile Thr Gly Phe
             20                  25                  30

Gln Val Asp Ala Val Pro Ala Asn Gly Gln Thr Pro Ile Gln Arg Thr
         35                  40                  45

Ile Lys Pro Asp Val Arg Ser Tyr Thr Ile Thr Gly Leu Gln Pro Gly
     50                  55                  60

Thr Asp Tyr Lys Ile Tyr Leu Tyr Thr Leu Asn Asp Asn Ala Arg Ser
 65                  70                  75                  80

Ser Pro Val Val Ile Asp Ala Ser Thr
             85

<210> SEQ ID NO 7
<211> LENGTH: 90
<212> TYPE: PRT
<213> ORGANISM: Artificial Sequence
<220> FEATURE:
<223> OTHER INFORMATION: Chemically synthesized partial region of
      fibronectin named III-14

<400> SEQUENCE: 7

Ala Ile Asp Ala Pro Ser Asn Leu Arg Phe Leu Ala Thr Thr Pro Asn
 1               5                  10                  15

Ser Leu Leu Val Ser Trp Gln Pro Pro Arg Ala Arg Ile Thr Gly Tyr
             20                  25                  30

```
Ile Ile Lys Tyr Glu Lys Pro Gly Ser Pro Pro Arg Glu Val Val Pro
            35                  40                  45

Arg Pro Arg Pro Gly Val Thr Glu Ala Thr Ile Thr Gly Leu Glu Pro
 50                  55                  60

Gly Thr Glu Tyr Thr Ile Tyr Val Ile Ala Leu Lys Asn Asn Gln Lys
 65                  70                  75                  80

Ser Glu Pro Leu Ile Gly Arg Lys Lys Thr
                85                  90

<210> SEQ ID NO 8
<211> LENGTH: 25
<212> TYPE: PRT
<213> ORGANISM: Artificial Sequence
<220> FEATURE:
<223> OTHER INFORMATION: Chemically synthesized partial region of
      fibronectin named CS-1

<400> SEQUENCE: 8

Asp Glu Leu Pro Gln Leu Val Thr Leu Pro His Pro Asn Leu His Gly
 1               5                  10                  15

Pro Glu Ile Leu Asp Val Pro Ser Thr
                20                  25

<210> SEQ ID NO 9
<211> LENGTH: 274
<212> TYPE: PRT
<213> ORGANISM: Human
<220> FEATURE:
<221> NAME/KEY: misc
<222> LOCATION: (1)..(274)
<223> OTHER INFORMATION: Fibronectin fragment named C-274

<400> SEQUENCE: 9

Pro Thr Asp Leu Arg Phe Thr Asn Ile Gly Pro Asp Thr Met Arg Val
 1               5                  10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
 50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
            85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
            165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205
```

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp

<210> SEQ ID NO 10
<211> LENGTH: 271
<212> TYPE: PRT
<213> ORGANISM: Human
<220> FEATURE:
<221> NAME/KEY: misc
<222> LOCATION: (1)..(271)
<223> OTHER INFORMATION: Fibronectin fragment named H-271

<400> SEQUENCE: 10

Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
                20                  25                  30

Arg Val Arg Val Thr Pro Lys Glu Lys Thr Gly Pro Met Lys Glu Ile
            35                  40                  45

Asn Leu Ala Pro Asp Ser Ser Ser Val Val Val Ser Gly Leu Met Val
50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Thr Leu Glu Asn Val Ser Pro
                85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr
            260                 265                 270

<210> SEQ ID NO 11
<211> LENGTH: 296
<212> TYPE: PRT
<213> ORGANISM: Artificial Sequence
<220> FEATURE:
<223> OTHER INFORMATION: Synthetic fibronectin fragment named H-296

<400> SEQUENCE: 11

```
Ala Ile Pro Ala Pro Thr Asp Leu Lys Phe Thr Gln Val Thr Pro Thr
1               5                   10                  15

Ser Leu Ser Ala Gln Trp Thr Pro Pro Asn Val Gln Leu Thr Gly Tyr
            20                  25                  30

Arg Val Arg Val Thr Pro Lys Glu Lys Thr Gly Pro Met Lys Glu Ile
        35                  40                  45

Asn Leu Ala Pro Asp Ser Ser Val Val Ser Gly Leu Met Val
50                  55                  60

Ala Thr Lys Tyr Glu Val Ser Val Tyr Ala Leu Lys Asp Thr Leu Thr
65                  70                  75                  80

Ser Arg Pro Ala Gln Gly Val Val Thr Leu Glu Asn Val Ser Pro
                85                  90                  95

Pro Arg Arg Ala Arg Val Thr Asp Ala Thr Glu Thr Thr Ile Thr Ile
            100                 105                 110

Ser Trp Arg Thr Lys Thr Glu Thr Ile Thr Gly Phe Gln Val Asp Ala
        115                 120                 125

Val Pro Ala Asn Gly Gln Thr Pro Ile Gln Arg Thr Ile Lys Pro Asp
130                 135                 140

Val Arg Ser Tyr Thr Ile Thr Gly Leu Gln Pro Gly Thr Asp Tyr Lys
145                 150                 155                 160

Ile Tyr Leu Tyr Thr Leu Asn Asp Asn Ala Arg Ser Ser Pro Val Val
                165                 170                 175

Ile Asp Ala Ser Thr Ala Ile Asp Ala Pro Ser Asn Leu Arg Phe Leu
            180                 185                 190

Ala Thr Thr Pro Asn Ser Leu Leu Val Ser Trp Gln Pro Pro Arg Ala
        195                 200                 205

Arg Ile Thr Gly Tyr Ile Ile Lys Tyr Glu Lys Pro Gly Ser Pro Pro
210                 215                 220

Arg Glu Val Val Pro Arg Pro Arg Pro Gly Val Thr Glu Ala Thr Ile
225                 230                 235                 240

Thr Gly Leu Glu Pro Gly Thr Glu Tyr Thr Ile Tyr Val Ile Ala Leu
                245                 250                 255

Lys Asn Asn Gln Lys Ser Glu Pro Leu Ile Gly Arg Lys Lys Thr Asp
            260                 265                 270

Glu Leu Pro Gln Leu Val Thr Leu Pro His Pro Asn Leu His Gly Pro
        275                 280                 285

Glu Ile Leu Asp Val Pro Ser Thr
    290                 295
```

<210> SEQ ID NO 12
<211> LENGTH: 549
<212> TYPE: PRT
<213> ORGANISM: Artificial Sequence
<220> FEATURE:
<223> OTHER INFORMATION: Synthetic fibronectin fragment named CH-271

<400> SEQUENCE: 12

```
Pro Thr Asp Leu Arg Phe Thr Asn Ile Gly Pro Asp Thr Met Arg Val
1               5                   10                  15
Thr Trp Ala Pro Pro Ser Ile Asp Leu Thr Asn Phe Leu Val Arg
            20              25                  30
Tyr Ser Pro Val Lys Asn Glu Glu Asp Val Ala Glu Leu Ser Ile Ser
        35                  40                  45
Pro Ser Asp Asn Ala Val Val Leu Thr Asn Leu Leu Pro Gly Thr Glu
    50                  55                  60
Tyr Val Val Ser Val Ser Ser Val Tyr Glu Gln His Glu Ser Thr Pro
65                  70                  75                  80
Leu Arg Gly Arg Gln Lys Thr Gly Leu Asp Ser Pro Thr Gly Ile Asp
                85                  90                  95
Phe Ser Asp Ile Thr Ala Asn Ser Phe Thr Val His Trp Ile Ala Pro
            100                 105                 110
Arg Ala Thr Ile Thr Gly Tyr Arg Ile Arg His His Pro Glu His Phe
                115                 120                 125
Ser Gly Arg Pro Arg Glu Asp Arg Val Pro His Ser Arg Asn Ser Ile
    130                 135                 140
Thr Leu Thr Asn Leu Thr Pro Gly Thr Glu Tyr Val Val Ser Ile Val
145                 150                 155                 160
Ala Leu Asn Gly Arg Glu Glu Ser Pro Leu Leu Ile Gly Gln Gln Ser
                165                 170                 175
Thr Val Ser Asp Val Pro Arg Asp Leu Glu Val Val Ala Ala Thr Pro
            180                 185                 190
Thr Ser Leu Leu Ile Ser Trp Asp Ala Pro Ala Val Thr Val Arg Tyr
        195                 200                 205
Tyr Arg Ile Thr Tyr Gly Glu Thr Gly Gly Asn Ser Pro Val Gln Glu
210                 215                 220
Phe Thr Val Pro Gly Ser Lys Ser Thr Ala Thr Ile Ser Gly Leu Lys
225                 230                 235                 240
Pro Gly Val Asp Tyr Thr Ile Thr Val Tyr Ala Val Thr Gly Arg Gly
                245                 250                 255
Asp Ser Pro Ala Ser Ser Lys Pro Ile Ser Ile Asn Tyr Arg Thr Glu
            260                 265                 270
Ile Asp Lys Pro Ser Met Ala Ile Pro Ala Pro Thr Asp Leu Lys Phe
        275                 280                 285
Thr Gln Val Thr Pro Thr Ser Leu Ser Ala Gln Trp Thr Pro Pro Asn
    290                 295                 300
Val Gln Leu Thr Gly Tyr Arg Val Arg Val Thr Pro Lys Glu Lys Thr
305                 310                 315                 320
Gly Pro Met Lys Glu Ile Asn Leu Ala Pro Asp Ser Ser Ser Val Val
                325                 330                 335
Val Ser Gly Leu Met Val Ala Thr Lys Tyr Glu Val Ser Val Tyr Ala
            340                 345                 350
Leu Lys Asp Thr Leu Thr Ser Arg Pro Ala Gln Gly Val Val Thr Thr
        355                 360                 365
Leu Glu Asn Val Ser Pro Pro Arg Arg Ala Arg Val Thr Asp Ala Thr
    370                 375                 380
Glu Thr Thr Ile Thr Ile Ser Trp Arg Thr Lys Thr Glu Thr Ile Thr
385                 390                 395                 400
Gly Phe Gln Val Asp Ala Val Pro Ala Asn Gly Gln Thr Pro Ile Gln
                405                 410                 415
```

```
Arg Thr Ile Lys Pro Asp Val Arg Ser Tyr Thr Ile Thr Gly Leu Gln
                420                 425                 430

Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
        450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
                485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
        515                 520                 525

Ile Tyr Val Ile Ala Leu Lys Asn Asn Gln Lys Ser Glu Pro Leu Ile
    530                 535                 540

Gly Arg Lys Lys Thr
545

<210> SEQ ID NO 13
<211> LENGTH: 574
<212> TYPE: PRT
<213> ORGANISM: Artificial Sequence
<220> FEATURE:
<223> OTHER INFORMATION: Synthetic fibronectin fragment named CH-296

<400> SEQUENCE: 13

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
        35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220
```

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
            245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
            275                 280                 285

Thr Gln Val Thr Pro Thr Ser Leu Ser Ala Gln Trp Thr Pro Pro Asn
290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
            325                 330                 335

Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
            355                 360                 365

Leu Glu Asn Val Ser Pro Pro Arg Arg Ala Arg Val Thr Asp Ala Thr
370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
            405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
            435                 440                 445

Arg Ser Ser Pro Val Val Ile Asp Ala Ser Thr Ala Ile Asp Ala Pro
450                 455                 460

Ser Asn Leu Arg Phe Leu Ala Thr Thr Pro Asn Ser Leu Leu Val Ser
465                 470                 475                 480

Trp Gln Pro Pro Arg Ala Arg Ile Thr Gly Tyr Ile Ile Lys Tyr Glu
            485                 490                 495

Lys Pro Gly Ser Pro Pro Arg Glu Val Val Pro Arg Pro Arg Pro Gly
            500                 505                 510

Val Thr Glu Ala Thr Ile Thr Gly Leu Glu Pro Gly Thr Glu Tyr Thr
            515                 520                 525

Ile Tyr Val Ile Ala Leu Lys Asn Asn Gln Lys Ser Glu Pro Leu Ile
530                 535                 540

Gly Arg Lys Lys Thr Asp Glu Leu Pro Gln Leu Val Thr Leu Pro His
545                 550                 555                 560

Pro Asn Leu His Gly Pro Glu Ile Leu Asp Val Pro Ser Thr
            565                 570

<210> SEQ ID NO 14
<211> LENGTH: 302
<212> TYPE: PRT
<213> ORGANISM: Artificial Sequence
<220> FEATURE:
<223> OTHER INFORMATION: Synthetic fibronectin fragment named C-CS1

-continued

```
<400> SEQUENCE: 14

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Glu Leu Pro Gln Leu Val Thr Leu Pro His
        275                 280                 285

Pro Asn Leu His Gly Pro Glu Ile Leu Asp Val Pro Ser Thr
    290                 295                 300

<210> SEQ ID NO 15
<211> LENGTH: 367
<212> TYPE: PRT
<213> ORGANISM: Artificial Sequence
<220> FEATURE:
<223> OTHER INFORMATION: Synthetic fibronectin fragment named CHV-89

<400> SEQUENCE: 15

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45
```

```
Pro Ser Asp Asn Ala Val Val Leu Thr Asn Leu Leu Pro Gly Thr Glu
    50                  55                  60

Tyr Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Arg Arg Ala Arg Val
        275                 280                 285

Thr Asp Ala Thr Glu Thr Thr Ile Thr Ile Ser Trp Arg Thr Lys Thr
    290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

Thr Gly Leu Gln Pro Gly Thr Asp Tyr Lys Ile Tyr Leu Tyr Thr Leu
            340                 345                 350

Asn Asp Asn Ala Arg Ser Ser Pro Val Val Ile Asp Ala Ser Thr
        355                 360                 365
```

<210> SEQ ID NO 16
<211> LENGTH: 368
<212> TYPE: PRT
<213> ORGANISM: Artificial Sequence
<220> FEATURE:
<223> OTHER INFORMATION: Synthetic fibronectin fragment named CHV-90

<400> SEQUENCE: 16

```
Pro Thr Asp Leu Arg Phe Thr Asn Ile Gly Pro Asp Thr Met Arg Val
 1               5                  10                  15

Thr Trp Ala Pro Pro Pro Ser Ile Asp Leu Thr Asn Phe Leu Val Arg
                20                  25                  30

Tyr Ser Pro Val Lys Asn Glu Glu Asp Val Ala Glu Leu Ser Ile Ser
            35                  40                  45
```

```
Pro Ser Asp Asn Ala Val Val Leu Thr Asn Leu Leu Pro Gly Thr Glu
     50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
            115                 120                 125

Ser Gly Arg Pro Arg Glu Asp Arg Val Pro His Ser Arg Asn Ser Ile
130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
            195                 200                 205

Tyr Arg Ile Thr Tyr Gly Glu Thr Gly Gly Asn Ser Pro Val Gln Glu
210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Asp Ala Pro Ser Asn Leu Arg Phe
            275                 280                 285

Leu Ala Thr Thr Pro Asn Ser Leu Leu Val Ser Trp Gln Pro Pro Arg
            290                 295                 300

Ala Arg Ile Thr Gly Tyr Ile Ile Lys Tyr Glu Lys Pro Gly Ser Pro
305                 310                 315                 320

Pro Arg Glu Val Val Pro Arg Pro Arg Pro Gly Val Thr Glu Ala Thr
                325                 330                 335

Ile Thr Gly Leu Glu Pro Gly Thr Glu Tyr Thr Ile Tyr Val Ile Ala
            340                 345                 350

Leu Lys Asn Asn Gln Lys Ser Glu Pro Leu Ile Gly Arg Lys Lys Thr
            355                 360                 365

<210> SEQ ID NO 17
<211> LENGTH: 370
<212> TYPE: PRT
<213> ORGANISM: Artificial Sequence
<220> FEATURE:
<223> OTHER INFORMATION: Synthetic fibronectin fragment named CHV-92

<400> SEQUENCE: 17

Pro Thr Asp Leu Arg Phe Thr Asn Ile Gly Pro Asp Thr Met Arg Val
 1               5                  10                  15

Thr Trp Ala Pro Pro Ser Ile Asp Leu Thr Asn Phe Leu Val Arg
                 20                  25                  30

Tyr Ser Pro Val Lys Asn Glu Glu Asp Val Ala Glu Leu Ser Ile Ser
                 35                  40                  45
```

```
Pro Ser Asp Asn Ala Val Val Leu Thr Asn Leu Leu Pro Gly Thr Glu
    50                  55                  60

Tyr Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
        130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
        210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
                260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
        290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335

Val Ser Gly Leu Met Val Ala Thr Lys Tyr Glu Val Ser Val Tyr Ala
                340                 345                 350

Leu Lys Asp Thr Leu Thr Ser Arg Pro Ala Gln Gly Val Val Thr Thr
        355                 360                 365

Leu Glu
    370

<210> SEQ ID NO 18
<211> LENGTH: 457
<212> TYPE: PRT
<213> ORGANISM: Artificial Sequence
<220> FEATURE:
<223> OTHER INFORMATION: Synthetic fibronectin fragment named CHV-179

<400> SEQUENCE: 18

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
                20                  25                  30
```

-continued

```
Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
 50                  55                  60

Tyr Val Val Ser Val Ser Ser Val Tyr Glu Gln His Glu Ser Thr Pro
 65                  70                  75                  80

Leu Arg Gly Arg Gln Lys Thr Gly Leu Asp Ser Pro Thr Gly Ile Asp
                 85                  90                  95

Phe Ser Asp Ile Thr Ala Asn Ser Phe Thr Val His Trp Ile Ala Pro
                100                 105                 110

Arg Ala Thr Ile Thr Gly Tyr Arg Ile Arg His His Pro Glu His Phe
                115                 120                 125

Ser Gly Arg Pro Arg Glu Asp Arg Val Pro His Ser Arg Asn Ser Ile
            130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
                180                 185                 190

Thr Ser Leu Leu Ile Ser Trp Asp Ala Pro Ala Val Thr Val Arg Tyr
                195                 200                 205

Tyr Arg Ile Thr Tyr Gly Glu Thr Gly Gly Asn Ser Pro Val Gln Glu
            210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Asn Val Ser Pro Arg Arg Ala Arg Val
            275                 280                 285

Thr Asp Ala Thr Glu Thr Thr Ile Thr Ile Ser Trp Arg Thr Lys Thr
            290                 295                 300

Glu Thr Ile Thr Gly Phe Gln Val Asp Ala Val Pro Ala Asn Gly Gln
305                 310                 315                 320

Thr Pro Ile Gln Arg Thr Ile Lys Pro Asp Val Arg Ser Tyr Thr Ile
                325                 330                 335

Thr Gly Leu Gln Pro Gly Thr Asp Tyr Lys Ile Tyr Leu Tyr Thr Leu
                340                 345                 350

Asn Asp Asn Ala Arg Ser Ser Pro Val Val Ile Asp Ala Ser Thr Ala
            355                 360                 365

Ile Asp Ala Pro Ser Asn Leu Arg Phe Leu Ala Thr Thr Pro Asn Ser
            370                 375                 380

Leu Leu Val Ser Trp Gln Pro Pro Arg Ala Arg Ile Thr Gly Tyr Ile
385                 390                 395                 400

Ile Lys Tyr Glu Lys Pro Gly Ser Pro Arg Glu Val Val Pro Arg
                405                 410                 415

Pro Arg Pro Gly Val Thr Glu Ala Thr Ile Thr Gly Leu Glu Pro Gly
                420                 425                 430
```

-continued

```
Thr Glu Tyr Thr Ile Tyr Val Ile Ala Leu Lys Asn Gln Lys Ser
            435                 440                 445

Glu Pro Leu Ile Gly Arg Lys Lys Thr
    450                 455

<210> SEQ ID NO 19
<211> LENGTH: 459
<212> TYPE: PRT
<213> ORGANISM: Artificial Sequence
<220> FEATURE:
<223> OTHER INFORMATION: Synthetic fibronectin fragment named CHV-181

<400> SEQUENCE: 19

Pro Thr Asp Leu Arg Phe Thr Asn Ile Gly Pro Asp Thr Met Arg Val
1               5                   10                  15

Thr Trp Ala Pro Pro Ser Ile Asp Leu Thr Asn Phe Leu Val Arg
            20                  25                  30

Tyr Ser Pro Val Lys Asn Glu Glu Asp Val Ala Glu Leu Ser Ile Ser
            35                  40                  45

Pro Ser Asp Asn Ala Val Val Leu Thr Asn Leu Leu Pro Gly Thr Glu
    50                  55                  60

Tyr Val Val Ser Val Ser Ser Val Tyr Glu Gln His Glu Ser Thr Pro
65                  70                  75                  80

Leu Arg Gly Arg Gln Lys Thr Gly Leu Asp Ser Pro Thr Gly Ile Asp
                85                  90                  95

Phe Ser Asp Ile Thr Ala Asn Ser Phe Thr Val His Trp Ile Ala Pro
            100                 105                 110

Arg Ala Thr Ile Thr Gly Tyr Arg Ile Arg His His Pro Glu His Phe
        115                 120                 125

Ser Gly Arg Pro Arg Glu Asp Arg Val Pro His Ser Arg Asn Ser Ile
    130                 135                 140

Thr Leu Thr Asn Leu Thr Pro Gly Thr Glu Tyr Val Val Ser Ile Val
145                 150                 155                 160

Ala Leu Asn Gly Arg Glu Glu Ser Pro Leu Leu Ile Gly Gln Gln Ser
                165                 170                 175

Thr Val Ser Asp Val Pro Arg Asp Leu Glu Val Val Ala Ala Thr Pro
            180                 185                 190

Thr Ser Leu Leu Ile Ser Trp Asp Ala Pro Ala Val Thr Val Arg Tyr
        195                 200                 205

Tyr Arg Ile Thr Tyr Gly Glu Thr Gly Gly Asn Ser Pro Val Gln Glu
    210                 215                 220

Phe Thr Val Pro Gly Ser Lys Ser Thr Ala Thr Ile Ser Gly Leu Lys
225                 230                 235                 240

Pro Gly Val Asp Tyr Thr Ile Thr Val Tyr Ala Val Thr Gly Arg Gly
                245                 250                 255

Asp Ser Pro Ala Ser Ser Lys Pro Ile Ser Ile Asn Tyr Arg Thr Glu
            260                 265                 270

Ile Asp Lys Pro Ser Met Ala Ile Pro Ala Pro Thr Asp Leu Lys Phe
        275                 280                 285

Thr Gln Val Thr Pro Thr Ser Leu Ser Ala Gln Trp Thr Pro Pro Asn
    290                 295                 300

Val Gln Leu Thr Gly Tyr Arg Val Arg Val Thr Pro Lys Glu Lys Thr
305                 310                 315                 320

Gly Pro Met Lys Glu Ile Asn Leu Ala Pro Asp Ser Ser Ser Val Val
                325                 330                 335
```

```
Val Ser Gly Leu Met Val Ala Thr Lys Tyr Glu Val Ser Val Tyr Ala
            340                 345                 350

Leu Lys Asp Thr Leu Thr Ser Arg Pro Ala Gln Gly Val Val Thr Thr
        355                 360                 365

Leu Glu Asn Val Ser Pro Pro Arg Arg Ala Arg Val Thr Asp Ala Thr
    370                 375                 380

Glu Thr Thr Ile Thr Ile Ser Trp Arg Thr Lys Thr Glu Thr Ile Thr
385                 390                 395                 400

Gly Phe Gln Val Asp Ala Val Pro Ala Asn Gly Gln Thr Pro Ile Gln
                405                 410                 415

Arg Thr Ile Lys Pro Asp Val Arg Ser Tyr Thr Ile Thr Gly Leu Gln
            420                 425                 430

Pro Gly Thr Asp Tyr Lys Ile Tyr Leu Tyr Thr Leu Asn Asp Asn Ala
        435                 440                 445

Arg Ser Ser Pro Val Val Ile Asp Ala Ser Thr
    450                 455

<210> SEQ ID NO 20
<211> LENGTH: 276
<212> TYPE: PRT
<213> ORGANISM: Artificial Sequence
<220> FEATURE:
<223> OTHER INFORMATION: Synthetic fibronectin fragment named H-275-Cys

<400> SEQUENCE: 20

Met Ala Ala Ser Ala Ile Pro Ala Pro Thr Asp Leu Lys Phe Thr Gln
1               5                   10                  15

Val Thr Pro Thr Ser Leu Ser Ala Gln Trp Thr Pro Pro Asn Val Gln
            20                  25                  30

Leu Thr Gly Tyr Arg Val Arg Val Thr Pro Lys Glu Lys Thr Gly Pro
        35                  40                  45

Met Lys Glu Ile Asn Leu Ala Pro Asp Ser Ser Ser Val Val Val Ser
    50                  55                  60

Gly Leu Met Val Ala Thr Lys Tyr Glu Val Ser Val Tyr Ala Leu Lys
65                  70                  75                  80

Asp Thr Leu Thr Ser Arg Pro Ala Gln Gly Val Val Thr Thr Leu Glu
                85                  90                  95

Asn Val Ser Pro Pro Arg Arg Ala Arg Val Thr Asp Ala Thr Glu Thr
            100                 105                 110

Thr Ile Thr Ile Ser Trp Arg Thr Lys Thr Glu Thr Ile Thr Gly Phe
        115                 120                 125

Gln Val Asp Ala Val Pro Ala Asn Gly Gln Thr Pro Ile Gln Arg Thr
    130                 135                 140

Ile Lys Pro Asp Val Arg Ser Tyr Thr Ile Thr Gly Leu Gln Pro Gly
145                 150                 155                 160

Thr Asp Tyr Lys Ile Tyr Leu Tyr Thr Leu Asn Asp Asn Ala Arg Ser
                165                 170                 175

Ser Pro Val Val Ile Asp Ala Ser Thr Ala Ile Asp Ala Pro Ser Asn
            180                 185                 190

Leu Arg Phe Leu Ala Thr Thr Pro Asn Ser Leu Leu Val Ser Trp Gln
        195                 200                 205

Pro Pro Arg Ala Arg Ile Thr Gly Tyr Ile Ile Lys Tyr Glu Lys Pro
    210                 215                 220

Gly Ser Pro Pro Arg Glu Val Val Pro Arg Pro Arg Pro Gly Val Thr
225                 230                 235                 240
```

-continued

Glu Ala Thr Ile Thr Gly Leu Glu Pro Gly Thr Glu Tyr Thr Ile Tyr
                245                 250                 255

Val Ile Ala Leu Lys Asn Asn Gln Lys Ser Glu Pro Leu Ile Gly Arg
            260                 265                 270

Lys Lys Thr Cys
        275

<210> SEQ ID NO 21
<211> LENGTH: 38
<212> TYPE: DNA
<213> ORGANISM: Artificial Sequence
<220> FEATURE:
<223> OTHER INFORMATION: Synthetic primer 12S

<400> SEQUENCE: 21
aaaccatggc agctagcgct attcctgcac caactgac                             38

<210> SEQ ID NO 22
<211> LENGTH: 36
<212> TYPE: DNA
<213> ORGANISM: Artificial Sequence
<220> FEATURE:
<223> OTHER INFORMATION: Synthetic primer 14A

<400> SEQUENCE: 22
aaaggatccc taactagtct ttttccttcc aatcag                               36

<210> SEQ ID NO 23
<211> LENGTH: 40
<212> TYPE: DNA
<213> ORGANISM: Artificial Sequence
<220> FEATURE:
<223> OTHER INFORMATION: Synthetic primer Cys-A

<400> SEQUENCE: 23
aaaagcggcc gctagcgcaa gccatggtct gtttcctgtg                           40

<210> SEQ ID NO 24
<211> LENGTH: 41
<212> TYPE: DNA
<213> ORGANISM: Artificial Sequence
<220> FEATURE:
<223> OTHER INFORMATION: Synthetic primer Cys-S

<400> SEQUENCE: 24
aaaagcggcc gcactagtgc atagggatcc ggctgagcaa c                         41

<210> SEQ ID NO 25
<211> LENGTH: 658
<212> TYPE: PRT
<213> ORGANISM: Artificial Sequence
<220> FEATURE:
<223> OTHER INFORMATION: Synthetic fibronectin fragment named CH-296Na

<400> SEQUENCE: 25

Met Pro Thr Asp Leu Arg Phe Thr Asn Ile Gly Pro Asp Thr Met Arg
1               5                   10                  15

Val Thr Trp Ala Pro Pro Pro Ser Ile Asp Leu Thr Asn Phe Leu Val
            20                  25                  30

Arg Tyr Ser Pro Val Lys Asn Glu Glu Asp Val Ala Glu Leu Ser Ile
        35                  40                  45

Ser Pro Ser Asp Asn Ala Val Val Leu Thr Asn Leu Leu Pro Gly Thr
    50                  55                  60

```
Glu Tyr Val Val Ser Val Ser Ser Val Tyr Glu Gln His Glu Ser Thr
 65                  70                  75                  80

Pro Leu Arg Gly Arg Gln Lys Thr Gly Leu Asp Ser Pro Thr Gly Ile
             85                  90                  95

Asp Phe Ser Asp Ile Thr Ala Asn Ser Phe Thr Val His Trp Ile Ala
            100                 105                 110

Pro Arg Ala Thr Ile Thr Gly Tyr Arg Ile Arg His His Pro Glu His
            115                 120                 125

Phe Ser Gly Arg Pro Arg Glu Asp Arg Val Pro His Ser Arg Asn Ser
        130                 135                 140

Ile Thr Leu Thr Asn Leu Thr Pro Gly Thr Glu Tyr Val Val Ser Ile
145                 150                 155                 160

Val Ala Leu Asn Gly Arg Glu Glu Ser Pro Leu Leu Ile Gly Gln Gln
                165                 170                 175

Ser Thr Val Ser Asp Val Pro Arg Asp Leu Glu Val Val Ala Ala Thr
            180                 185                 190

Pro Thr Ser Leu Leu Ile Ser Trp Asp Ala Pro Ala Val Thr Val Arg
            195                 200                 205

Tyr Tyr Arg Ile Thr Tyr Gly Glu Thr Gly Gly Asn Ser Pro Val Gln
        210                 215                 220

Glu Phe Thr Val Pro Gly Ser Lys Ser Thr Ala Thr Ile Ser Gly Leu
225                 230                 235                 240

Lys Pro Gly Val Asp Tyr Thr Ile Thr Val Tyr Ala Val Thr Gly Arg
                245                 250                 255

Gly Asp Ser Pro Ala Ser Ser Lys Pro Ile Ser Ile Asn Tyr Arg Thr
            260                 265                 270

Glu Ile Asp Lys Pro Ser Gln Met Gln Val Thr Asp Val Gln Asp Asn
            275                 280                 285

Ser Ile Ser Val Lys Trp Leu Pro Ser Ser Pro Val Thr Gly Tyr
            290                 295                 300

Arg Val Thr Thr Thr Pro Lys Asn Gly Pro Gly Pro Thr Lys Thr Lys
305                 310                 315                 320

Thr Ala Gly Pro Asp Gln Thr Glu Met Thr Ile Glu Gly Leu Gln Pro
                325                 330                 335

Thr Val Glu Tyr Val Val Ser Val Tyr Ala Gln Asn Pro Ser Gly Glu
            340                 345                 350

Ser Gln Pro Leu Val Gln Thr Ala Val Thr Ala Ile Pro Ala Pro Thr
            355                 360                 365

Asp Leu Lys Phe Thr Gln Val Thr Pro Thr Ser Leu Ser Ala Gln Trp
        370                 375                 380

Thr Pro Pro Asn Val Gln Leu Thr Gly Tyr Arg Val Arg Val Thr Pro
385                 390                 395                 400

Lys Glu Lys Thr Gly Pro Met Lys Glu Ile Asn Leu Ala Pro Asp Ser
                405                 410                 415

Ser Ser Val Val Val Ser Gly Leu Met Val Ala Thr Lys Tyr Glu Val
            420                 425                 430

Ser Val Tyr Ala Leu Lys Asp Thr Leu Thr Ser Arg Pro Ala Gln Gly
            435                 440                 445

Val Val Thr Thr Leu Glu Asn Val Ser Pro Pro Arg Arg Ala Arg Val
        450                 455                 460

Thr Asp Ala Thr Glu Thr Thr Ile Thr Ile Ser Trp Arg Thr Lys Thr
465                 470                 475                 480
```

Glu Thr Ile Thr Gly Phe Gln Val Asp Ala Val Pro Ala Asn Gly Gln
                485                 490                 495

Thr Pro Ile Gln Arg Thr Ile Lys Pro Asp Val Arg Ser Tyr Thr Ile
            500                 505                 510

Thr Gly Leu Gln Pro Gly Thr Asp Tyr Lys Ile Tyr Leu Tyr Thr Leu
        515                 520                 525

Asn Asp Asn Ala Arg Ser Ser Pro Val Val Ile Asp Ala Ser Thr Ala
    530                 535                 540

Ile Asp Ala Pro Ser Asn Leu Arg Phe Leu Ala Thr Thr Pro Asn Ser
545                 550                 555                 560

Leu Leu Val Ser Trp Gln Pro Pro Arg Ala Arg Ile Thr Gly Tyr Ile
                565                 570                 575

Ile Lys Tyr Glu Lys Pro Gly Ser Pro Arg Glu Val Val Pro Arg
            580                 585                 590

Pro Arg Pro Gly Val Thr Glu Ala Thr Ile Thr Gly Leu Glu Pro Gly
        595                 600                 605

Thr Glu Tyr Thr Ile Tyr Val Ile Ala Leu Lys Asn Asn Gln Lys Ser
    610                 615                 620

Glu Pro Leu Ile Gly Arg Lys Lys Thr Asp Glu Leu Pro Gln Leu Val
625                 630                 635                 640

Thr Leu Pro His Pro Asn Leu His Gly Pro Glu Ile Leu Asp Val Pro
                645                 650                 655

Ser Thr

<210> SEQ ID NO 26
<211> LENGTH: 1989
<212> TYPE: DNA
<213> ORGANISM: Artificial Sequence
<220> FEATURE:
<223> OTHER INFORMATION: Synthetic polynucleotide coding CH-296Na

<400> SEQUENCE: 26
catatgccca ctgacctgcg attcaccaac attggtccag acaccatgcg tgtcacctgg    60
gctccacccc catccattga tttaaccaac ttcctggtgc gttactcgcc tgtgaaaaat    120
gaggaagatg ttgcagagtt gtcaatttct ccttcagaca atgcagtggt cttaacaaat    180
ctcctgcctg gtacagaata tgtagtgagt gtctccagtg tctacgaaca acatgagagc    240
acacctctta gaggaagaca gaaaacaggt cttgattccc caactggcat tgacttttct    300
gatattactg ccaactcttt tactgtgcac tggattgctc ctcgagccac catcactggc    360
tacaggatcc gccatcatcc cgagcacttc agtgggagac tcgagaaga tcgggtgccc    420 cactctcgga attccatcac cctcaccaac ctcactccag gcacagagta tgtggtcagc    480
atcgttgctc ttaatggcag agaggaaagt cccttattga ttggccaaca atcaacagtt    540
tctgatgttc cgagggacct ggaagttgtt gctgcgaccc ccaccagcct actgatcagc    600
tgggatgctc ctgctgtcac agtgagatat tacaggatca cttacggaga aacaggagga    660
aatagccctg tccaggagtt cactgtgcct gggagcaagt ctacagctac catcagcggc    720
cttaaacctg gagttgatta taccatcact gtgtatgctg tcactggccg tggagacagc    780
cccgcaagca gcaagccaat tccattaat taccgaacag aaattgacaa accatcccag    840
atgcaagtga ccgatgttca ggacaacagc attagtgtca agtggctgcc ttcaagttcc    900
cctgttactg gttacagagt aaccaccact cccaaaaatg gaccaggacc aacaaaaact    960
aaaactgcag gtccagatca aacagaaatg actattgaag gcttgcagcc cacagtggag   1020

-continued

```
tatgtggtta gtgtctatgc tcagaatcca agcggagaga gtcagcctct ggttcagact    1080
gcagtaaccg ctattcctgc accaactgac ctgaagttca ctcaggtcac acccacaagc    1140
ctgagcgccc agtggacacc acccaatgtt cagctcactg gatatcgagt gcgggtgacc    1200
cccaaggaga agaccggacc aatgaaagaa atcaaccttg ctcctgacag ctcatccgtg    1260
gttgtatcag gacttatggt ggccaccaaa tatgaagtga gtgtctatgc tcttaaggac    1320
actttgacaa gcagaccagc tcagggtgtt gtcaccactc tggagaatgt cagcccacca    1380
agaagggctc gtgtgacaga tgctactgag accaccatca ccattagctg gagaaccaag    1440
actgagacga tcactggctt ccaagttgat gccgttccag ccaatggcca gactccaatc    1500
cagagaacca tcaagccaga tgtcagaagc tacaccatta caggtttaca accaggcact    1560
gactacaaga tctacctgta caccttgaat gacaatgctc ggagctcccc tgtggtcatc    1620
gacgcctcca ctgccattga tgcaccatcc aacctgcgtt tcctggccac cacacccaat    1680
tccttgctgg tatcatggca gccgccacgt gccaggatta ccggctacat catcaagtat    1740
gagaagcctg ggtctcctcc cagagaagtg gtccctcggc cccgcccttgg tgtcacagag    1800 gctactatta ctggcctgga accgggaacc gaatatacaa tttatgtcat tgccctgaag    1860
aataatcaga gagcgagcc cctgattgga aggaaaaaga cagacgagct tccccaactg    1920 gtaaccettc cacaccccaa tcttcatgga ccagagatct ggatgttcc ttccacataa    1980 tagaagctt                                                            1989

<210> SEQ ID NO 27
<211> LENGTH: 22
<212> TYPE: DNA
<213> ORGANISM: Artificial Sequence
<220> FEATURE:
<223> OTHER INFORMATION: Synthetic primer CH-296Na1

<400> SEQUENCE: 27
atcatatgcc cactgacctg cg                                             22

<210> SEQ ID NO 28
<211> LENGTH: 23
<212> TYPE: DNA
<213> ORGANISM: Artificial Sequence
<220> FEATURE:
<223> OTHER INFORMATION: Synthetic primer CH-296Na2

<400> SEQUENCE: 28
ataagcttct attatgtgga agg                                            23

<210> SEQ ID NO 29
<211> LENGTH: 22
<212> TYPE: DNA
<213> ORGANISM: Artificial Sequence
<220> FEATURE:
<223> OTHER INFORMATION: Synthetic primer CH-296Na3

<400> SEQUENCE: 29
accatcactg gctacaggat cc                                             22

<210> SEQ ID NO 30
<211> LENGTH: 4
<212> TYPE: PRT
<213> ORGANISM: Artificial Sequence
<220> FEATURE:
<223> OTHER INFORMATION: Synthetic peptide
```

```
<400> SEQUENCE: 30

Met Ala Ala Ser
1
```

PROCESS FOR PRODUCING CYTOTOXIC LYMPHOCYTES

TECHNICAL FIELD

The present invention relates to a method for preparing a cytotoxic lymphocyte, which is useful in the medical field.

BACKGROUND ART

A living body is protected from foreign substances mainly by an immune response, and an immune system has been established by various cells and the soluble factors produced thereby. Among them, leukocytes, especially lymphocytes, play a key role. The lymphocytes are classified in two major types, B lymphocyte (which may be hereinafter referred to as B cell) and T lymphocyte (which may be hereinafter referred to as T cell), both of which specifically recognize an antigen and act on the antigen to protect the living body.

T cell is subclassified to helper T cell having CD (Cluster of Differentiation)4 marker (hereinafter referred to as $T_H$), mainly involved in assisting in antibody production and induction of various immune responses, and cytotoxic T cell having CD8 marker ($T_c$: cytotoxic T lymphocyte, also referred to as killer T cell, which may be hereinafter referred to as CTL), mainly exhibiting a cytotoxic activity. CTL, which plays the most important role in recognizing, destroying and eliminating tumor cell, virus-infected cell or the like, does not produce an antibody specifically reacting with an antigen like B cell, but directly recognizes and acts on antigens (antigenic peptide) from a target cell which is associated with major histocompatibility complex [MHC, which may be also referred to as human leukocyte antigen (HLA) in human] Class I molecules existing on the surface of the target cell membrane. At this time, T cell receptor (hereinafter referred to as TCR) existing on the surface of the CTL membrane specifically recognizes the above-mentioned antigenic peptides and MHC Class I molecules, and determines whether the antigenic peptide is autologous or nonautologous. Target cell which has been determined to be nonautologous is then specifically destroyed and eliminated by CTL.

Recent years, a therapy which would cause a heavy physical burden on a patient, such as pharmacotherapy and radiotherapy, has been reconsidered, and an interest has increased in an immunotherapy with a light physical burden on a patient. Especially, there has been remarked an effectiveness of adoptive immunotherapy in which CTL capable of specifically reacting with an antigen of interest is induced ex vivo from lymphocyte derived from a human having normal immune function, or the lymphocyte is expanded without induction, and then transferred to a patient. For instance, it has been suggested that in an animal model adoptive immunotherapy is an effective therapy for virus infection and tumor (for example, authored by Greenberg, P. D., published in 1992, *Advances in Immunology* and Reusser P. and three others, *Blood*, 1991, 78(5), 1373-1380). In this therapy, it is important to maintain or increase the cell number in a state in which the antigen-specific cytotoxic activity of the CTL is maintained or enhanced.

In the adoptive immunotherapy as described above, it is necessary to administer cytotoxic lymphocytes in the number of cells of a given amount or larger in order to obtain a therapeutic effect. In other words, it can be said that it is the greatest problem to obtain the above number of cells ex vivo in a short period of time.

In order to maintain and enhance an antigen-specific cytotoxic activity of CTL, there has been generally employed a method of repeating stimulation with an antigen of interest when a specific response to an antigen for CTL is induced. However, in this method, the number of CTL finally obtained may usually be decreased, so that a sufficient number of cells cannot be obtained.

As a method for preparing T cell which is effective for the treatment of a disease, there has been known, for instance, adoptive immunotherapy using a lymphokine-activated killer cell (LAK cell) (for example, Rosenberg S. A. et al., *N. Engl. J. Med.* 1987, 316(15), 889-897) and adoptive immunotherapy using a tumor-infiltrating lymphocyte (TIL) induced with interleukin-2 (IL-2) in a high concentration (for example, Rosenberg S. A. et al., *N. Engl. J. Med.*, 1988, 319(25), 1676-1680 and Ho M. and nine others, Blood, 1993, 81(8), 2093-2101).

Next, regarding the preparation of the antigen-specific CTL, there has been reported a method for isolating and expanding a CMV-specific CTL clone using autologous CMV infected fibroblast and IL-2 (for example, Riddell S. A. and four others, *J. Immunol.*, 1991, 146(8), 2795-2804) or using anti-CD3 monoclonal antibody (anti-CD3 mAb) and IL-2 (for example, Greenberg, P. D. and one other, *J. Immunol. Methods*, 1990, 128(2), 189-201).

Furthermore, WO 96/06929 discloses an REM method (rapid expansion method). This REM method is a method for expanding a primary T cell population containing antigen-specific CTL and $T_H$ in a short period of time. In other words, this method is characterized in that a large amount of T cell can be provided by proliferating individual T cell clones, and that the number of antigen-specific CTL is increased using an anti-CD3 antibody, IL-2, and PBMC (peripheral blood mononuclear cell) made deficient in an ability for proliferation by irradiation, and Epstein-Barr virus (hereinafter simply referred to as EBV)-infected cells.

In addition, WO 97/32970 discloses a modified REM method, wherein the method is a method using as a feeder cell a nondividing mammal cell strain expressing a T-cell stimulating component which is distinguishable from PBMC to reduce an amount of PBMC used.

The lymphokine-activated killer cell (LAK cell) is a functional cell population having a cytotoxic activity, which is obtained by adding IL-2 to peripheral blood (peripheral blood leukocyte), umbilical cord blood, tissue fluid or the like containing lymphocytes, and culturing the cells in vitro for several days. During the culture, proliferation of the LAK cell is further accelerated by adding an anti-CD3 antibody thereto and culturing the cell. The LAK cell thus obtained has a cytotoxic activity non-specifically to various cancer cells and other targets. The LAK cell is also used in the adoptive immunotherapy in the same manner as the above-mentioned CTL.

As described above, utilization of IL-2 is essential in the step of obtaining a cytotoxic lymphocyte, for instance, CTL, LAK cell, TIL or the like. The cell is further activated by binding of IL-2 to interleukin-2 receptor (IL-2R) on a cell surface. In addition, IL-2R has been known as an activation marker for a lymphocyte. From these viewpoints, it is important to improve IL-2R expression on the cell surface. In addition, in the induction of CTL, it is important to improve an efficiency for inducing a precursor cell of CTL subjected to stimulation by an antigen as CTL, i.e., to improve a proportion (ratio) of the CD8-positive cell in a group of cells after the induction.

Usually, serum or plasma is also added thereto in a ratio of 5% by volume to 20% by volume, when these lymphocytes are expanded ex vivo. This serum or plasma is a component required when a cell such as a lymphocyte is cultured ex vivo. However, risk of various virus infections and the like cannot be excluded, since serum or plasma is derived from blood of a nonautologous animal (human, bovid or the like). In addition, it is impossible to completely deny the presence of a virus or a pathogenic microorganism undetectable with current detection technique.

In this regard, in recent years, more and more serum or plasma derived from a patient (autologous serum or plasma) is used. However, it may lead to significant risk for the patient to take a large amount of blood from the patient for obtaining serum or plasma in an amount required for culture, since it causes a heavy physical burden on the patient. In order to avoid this risk, a small amount of serum or plasma is used to expand for obtaining lymphocytes required for treatment, which is to be consequently culture with low concentration of serum or plasma. Generally, growth of cells such as lymphocytes is unstable in the culture under low-serum or low-plasma conditions; thereby cells cannot be obtained in an amount required for the treatment. Furthermore, serum-free culture is strongly required for avoiding the physical burden and the risk of infection as mentioned above. However, most cells cannot grow under such culture conditions.

Therefore, a method for expanding a lymphocyte with low-serum or serum-free (low-plasma or plasma-free) is strongly required.

If a method for expanding a lymphocyte under serum-free (plasma-free) conditions is established, difference in serum or plasma among lots can be eliminated, and negative elements resulting from the serum or plasma from a patient (such as immunosuppressive components) can be excluded, whereby the advantage obtained by the establishment of such system is inestimable.

Fibronectin is a gigantic glycoprotein having a molecular weight of 250 thousands, which exists in an animal blood, on the surface of a cultured cell, or in an extracellular matrix of a tissue, and has been known to have various functions. A domain structure thereof is divided into seven portions (hereinafter refer to FIG. 1), wherein three kinds of similar sequences are contained in an amino acid sequence thereof, repetitions of each of these sequences constituting the entire sequence. Three kinds of the similar sequences are referred to as type I, type II and type III. Among them, the type III is constituted by 71 to 96 amino acid residues, wherein a coincidence ratio of these amino acid residues is 17 to 40%. In fibronectin, there are fourteen type III sequences, among which the 8th, 9th or 10th sequence (each being hereinafter referred to as III-8, III-9 or III-10) is contained in a cell binding domain, and the 12th, 13th or 14th sequence (each being hereinafter referred to as III-12, III-13 or III-14) is contained in a heparin binding domain. In addition, a VLA (very late activation antigen)-5 binding region is contained in III-10, and its core sequence is RGDS. In addition, a region referred to as IIICS exists at a C-terminal side of the heparin binding domain. A region referred to as CS-1 consisting of 25 amino acids and having a binding activity to VLA-4 exists in IIICS (for example, authored by Deane F. Momer, published in 1988, *FIBRONECTIN*, ACADEMIC PRESS INC., P1-8, Kimizuka F. and eight others, *J. Biochem.*, 1991, 110(2), 284-291 and Hanenberg H. and five others, *Human Gene Therapy*, 1997, 8(18), 2193-2206).

DISCLOSURE OF INVENTION

An object of the present invention is to provide a method for preparing a cytotoxic lymphocyte having a cytotoxic activity at a high level, Which is highly secure and suitably used in the medical field.

Summarizing the present invention, a first embodiment of the present invention relates to a method for preparing a cytotoxic lymphocyte characterized in that the method comprises a step of carrying out at least one step selected from induction, maintenance and expansion of a cytotoxic lymphocyte using a medium containing serum and plasma at a total concentration of 0% by volume or more and less than 5% by volume of the medium, in the presence of fibronectin, a fragment thereof or a mixture thereof. The cytotoxic lymphocyte prepared in the first embodiment of the present invention is exemplified by a cytotoxic lymphocyte which highly expresses an interleukin-2 receptor as compared to a cytotoxic lymphocyte prepared in the absence of fibronectin, a fragment thereof or a mixture thereof. In addition, the cytotoxic lymphocyte prepared in the first embodiment of the present invention is exemplified by a cytotoxic lymphocyte which contains CD8-positive cell in a higher ratio as compared to a cytotoxic lymphocyte prepared in the absence of fibronectin, a fragment thereof or a mixture thereof. Furthermore, the cytotoxic lymphocyte prepared in the first embodiment of the present invention is exemplified by a cytotoxic lymphocyte of which expansion fold is higher as compared to that of a cytotoxic lymphocyte prepared by the method for preparing a cytotoxic lymphocyte in the absence of fibronectin, a fragment thereof or a mixture thereof. Also, the cytotoxic lymphocyte prepared in the first embodiment of the present invention is exemplified by a cytotoxic lymphocyte which has a cytotoxic activity enhanced or highly maintained as compared to that of a cytotoxic lymphocyte prepared in the absence of fibronectin, a fragment thereof or a mixture thereof.

In the first embodiment of the present invention, use of fibronectin, a fragment thereof or a mixture thereof is exemplified by use wherein these are immobilized on a solid phase. Here, the solid phase is exemplified by a cell culture equipment or a cell culture carrier. The cell culture equipment is exemplified by a petri dish, a flask or a bag, and the cell culture carrier is exemplified by beads, a membrane or a slide glass.

In the first embodiment of the present invention, the cytotoxic lymphocyte is exemplified by a lymphokine-activated killer cell.

In the first embodiment of the present invention, the fibronectin fragment is exemplified by a polypeptide (m) comprising at least any one of the amino acid sequences shown in SEQ ID NOs: 1 to 8 of Sequence Listing, or a polypeptide (n) comprising at least one amino acid sequence having substitution, deletion, insertion or addition of one or the plural number of amino acids in any one of the above-mentioned amino acid sequences, wherein the polypeptide (n) has a function equivalent to that of the above-mentioned polypeptide (m). The fibronectin fragment is exemplified by those which have a cell adhesion activity and/or a heparin binding activity. The fibronectin fragment is also exemplified by at least one polypeptide selected from the group consisting of polypeptides having any one of the amino acid sequences shown in SEQ ID NOs: 9 to 20 and 25 of Sequence Listing.

In the first embodiment of the present invention, one embodiment of the preparation method which is carried out in a cell culture equipment is exemplified by a method which satisfies the conditions of:
(a) a ratio of the number of cells to a culture area in the cell culture equipment at initiation of culture being 1 cell/cm$^2$ to 5×10$^5$ cells/cm$^2$; and/or
(b) a concentration of cells in a medium at initiation of culture being 1 cell/mL to 5×10$^5$ cells/mL.

In addition, such preparation method is exemplified by a method which does not require a step of diluting a cell culture solution.

In the first embodiment of the present invention, when at least any one of induction, maintenance and expansion of a cytotoxic lymphocyte is carried out in the presence of fibronectin, a fragment thereof or a mixture thereof in a cell culture equipment containing a medium, the method is exemplified by, for example, a method which comprises at least one step of diluting the cell culture solution, step of exchanging the medium, or step of exchanging the cell culture equipment, wherein the culture conditions immediately after at least one step of diluting the cell culture solution, step of exchanging the medium, or step of exchanging the cell culture equipment satisfy the conditions of:
(c) a concentration of cells in the cell culture solution being $2\times05$ cells/mL to $1\times10^8$ cells/mL; or
(d) a ratio of the number of cells in the cell culture solution to a culture area in the cell culture equipment being $1\times10^5$ cells/cm$^2$ to $1\times10^8$ cells/cm$^2$.

In the preparation method of the first embodiment of the present invention, when at least any one of induction, maintenance and expansion of a cytotoxic lymphocyte is carried out in the presence of fibronectin, a fragment thereof or a mixture thereof in a cell culture equipment containing a medium, the method is exemplified by, but not limited to, a method comprising at least one step of diluting the cell culture solution, step of exchanging the medium or step of exchanging the cell culture equipment, wherein a total concentration of serum and plasma in the medium immediately after at least one step of diluting the cell culture solution, step of exchanging the medium, or step of exchanging the cell culture equipment is same as that at initiation of culture or lowered as compared to that at initiation of culture.

In the first embodiment of the present invention, a method further comprising a step of transducing a foreign gene into a cytotoxic lymphocyte is used as an example. Here, the transduction of the foreign gene is exemplified by a step comprising use of retrovirus, adenovirus, adeno-associated virus or simian virus.

A second embodiment of the present invention relates to a cytotoxic lymphocyte obtained by the method of the first embodiment of the present invention.

A third embodiment of the present invention relates to a medicament comprising as an effective ingredient the cytotoxic lymphocyte obtained by the method of the first embodiment of the present invention.

A fourth embodiment of the present invention relates to a medium for culturing a cytotoxic lymphocyte, characterized in that the medium comprises as an effective ingredient fibronectin, a fragment thereof or a mixture thereof, and that a total concentration of serum and plasma in the medium is 0% by volume or more and less than 5% by volume.

The present invention provides a method for preparing a cytotoxic lymphocyte, which is highly secure and of which burden on a patient is reduced.

BRIEF DESCRIPTION OF THE DRAWINGS

FIG. 1 is a schematic view showing a domain structure of fibronectin.

BEST MODE FOR CARRYING OUT THE INVENTION

The present invention has been completed by the findings that, by preparing a cytotoxic lymphocyte in the presence of fibronectin and/or a fibronectin fragment in the method for induction, maintenance or expansion of a cytotoxic lymphocyte, a cytotoxic lymphocyte has a sufficient cytotoxic activity even at a high expansion fold, a high expression level of IL-2R, and a high ratio of the CD8-positive cell, even if the content of the serum or plasma in the medium is lowered or eliminated.

Incidentally, the preparation of a cytotoxic lymphocyte as used herein refers to a step encompassing each of the steps of induction (activation), maintenance and expansion of the cell, or the combined steps thereof. The preparation of a cytotoxic lymphocyte of the present invention is also referred to culture of a cytotoxic lymphocyte.

The present invention will be explained concretely hereinbelow.

(1) Fibronectin and Fragment Thereof Used in the Present Invention

The fibronectin and a fragment thereof as mentioned herein may be those obtained from nature, or those which are artificially synthesized. The fibronectin and a fragment thereof can be prepared in a substantially pure form from a substance of natural origin, on the basis of the disclosure, for instance, of Ruoslahti E., et al. [*J. Biol. Chem.,* 256(14), 7277-7281 (1981)]. The term "substantially pure fibronectin or fibronectin fragment" as referred to herein means that these fibronectin and fibronectin fragment do not substantially contain other proteins and the like existing together with fibronectin in nature. Each of the above-mentioned fibronectin and a fragment thereof can be used in the present invention alone or in admixture of plural kinds.

Here, it is known that there are a large number of splicing variants of fibronectin. As the fibronectin used in the present invention, any variant can be used so long as the desired effects of the present invention are exhibited. For example, in the case of fibronectin derived from plasma, it is known that a region referred to as ED-B present in upstream of a cell binding domain and a region referred to as ED-A present between the cell binding domain and the heparin binding domain are deleted. Such fibronectin derived from plasma can also be used in the present invention.

The useful information relating to the fibronectin fragments which can be used in the present invention and the preparation of the fragments can be obtained from Kimiduka F., et al. [*J. Biochem.,* 110, 284-291 (1991)], Kornbrihtt A. R., et al. [*EMBO J.,* 4(7), 1755-1759 (1985)], Sekiguchi K., et al. [*Biochemistry,* 25(17), 4936-4941 (1986)], and the like. In addition, the amino acid sequence of fibronectin is disclosed in Genbank Accession No. NM_002026 (NP_002017).

In the present invention, the fibronectin fragment is exemplified by, for instance, a polypeptide (m) comprising at least one amino acid sequence comprising any of the regions of III-8 (amino acid sequence shown in SEQ ID NO: 1 of Sequence Listing), III-9 (amino acid sequence shown in SEQ ID NO: 2 of Sequence Listing), III-10 (amino acid sequence shown in SEQ ID NO: 3 of Sequence Listing), III-11 (amino acid sequence shown in SEQ ID NO: 4 of Sequence Listing), III-12 (amino acid sequence shown in SEQ ID NO: 5 of Sequence Listing), III-13 (amino acid sequence shown in SEQ ID NO: 6 of Sequence Listing), III-14 (amino acid sequence shown in SEQ ID NO: 7 of Sequence Listing), and CS-1 (amino acid sequence shown in SEQ ID NO: 8 of Sequence Listing) (see FIG. 1), or a polypeptide (n) comprising at least one amino acid sequence having substitution, deletion, insertion or addition of one or the plural number of amino acids in any of the amino acid sequences described above, wherein the polypeptide (n) has a function equivalent to that of the above-mentioned polypeptide (m).

In addition, as the fragment, a fragment having a cell adhesion activity and/or a heparin binding activity can be preferably used. The cell adhesion activity can be evaluated by assaying binding of the fragment (its cell binding domain) used in the present invention to a cell using a known method. For instance, the method as mentioned above includes a method of Williams D. A., et al. [Nature, 352, 438-441 (1991)]. The method is a method of determining the binding of a cell to a fragment immobilized on a culture plate. In addition, the heparin binding activity can be evaluated by assaying binding of the fragment (its heparin binding domain) used in the present invention to heparin using a known method. For instance, the binding of the fragment to heparin can be evaluated in the same manner by using heparin, for instance, a labeled heparin in place of the cell in the above-mentioned method of Williams D. A., et al.

Further, the fibronectin fragment is exemplified by a polypeptide selected from C-274 (amino acid sequence shown in SEQ ID NO: 9 of Sequence Listing), H-271 (amino acid sequence shown in SEQ ID NO: 10 of Sequence Listing), H-296 (amino acid sequence shown in SEQ ID NO: 11 of Sequence Listing), CH-271 (amino acid sequence shown in SEQ ID NO: 12 of Sequence Listing), CH-296 (amino acid sequence shown in SEQ ID NO: 13 of Sequence Listing), C-CS1 (amino acid sequence shown in SEQ ID NO: 14 of Sequence Listing), or CH-296Na (amino acid sequence shown in SEQ ID NO: 25 of Sequence Listing). Here, CH-296Na is a polypeptide prepared for the first time in the present application.

Each of the above-mentioned fragments CH-271, CH-296, CH-296Na, C-274 and C-CS1 is a polypeptide having a cell binding domain with a binding activity to VlA-5. Also, C-CS1, H-296, CH-296 and CH-296Na are polypeptides having CS-1 with a binding activity to VLA-4. Further, H-271, H-296, CH-271, CH-296 and CH-296Na are polypeptides having a heparin binding domain. Here, CH-296Na is a polypeptide comprising a region from the cell binding domain to CS-1 of fibronectin derived from plasma. Specifically, CH-296Na is a polypeptide wherein the region (ED-A) ranging from Asn at position 1631 to Thr at position 1720 is deleted from the polypeptide comprising the region from Pro at position 1270 to Thr at position 2016 of the amino acid sequence of the fibronectin disclosed in Genbank Accession No. NM_002026 (NP_002017).

In the present invention, a fragment in which each of the above domains is modified can also be used. The heparin binding domain of the fibronectin is constituted by three type III sequences (III-12, III-13 and III-14). A fragment containing a heparin binding domain having deletion of one or two of the above type III sequences can also be used in the present invention. For instance, the fragments may be exemplified by CHV-89 (amino acid sequence shown in SEQ ID NO: 15 of Sequence Listing), CHV-90 (amino acid sequence shown in SEQ ID NO: 16 of Sequence Listing) or CHV-92 (amino acid sequence shown in SEQ ID NO: 17 of Sequence Listing), which is a fragment in which a cell binding site of the fibronectin (VLA-5 binding domain: Pro1239 to Ser1515) and one of the III type sequences are bound, or CHV-179 (amino acid sequence shown in SEQ ID NO: 18 of Sequence Listing) or CHV-181 (amino acid sequence shown in SEQ ID NO: 19 of Sequence Listing), which is a fragment in which the cell binding site of the fibronectin and two of the type III sequences are bound. CHV-89, CHV-90 and CHV-92 contain III-13, III-14 and III-12, respectively, and CHV-179 contains III-13 and III-14, and CHV-181 contains III-12 and III-13, respectively.

In addition, a fragment having addition of an additional amino acid to each of the above-mentioned fragments can be used in the present invention. For instance, the fragment can be prepared by adding a desired amino acid to each of the above-mentioned fragment in accordance with the method for preparing H-275-Cys described in Preparation Examples set forth below. For instance, H-275-Cys (amino acid sequence shown in SEQ ID NO: 20 of Sequence Listing) is a fragment having a heparin binding domain of the fibronectin, and cysteine residue at a C-terminal.

The fragment used in the present invention may be those comprising a polypeptide comprising an amino acid sequence having substitution, deletion, insertion or addition of one or the plural number of amino acids in an amino acid sequence of a polypeptide constituting a fragment at least partially containing an amino acid sequence of naturally occurring fibronectin exemplified above, wherein the polypeptide has a function equivalent to that of the fragment, so long as the desired effects of the present invention are obtained.

It is preferable that the substitution or the like of the amino acids is carried out to an extent that it can change physicochemical characteristics and the like of an inherent polypeptide within the range that the function of the polypeptide can be maintained. For instance, it is preferable that the substitution or the like of amino acids is conservative, within the range that the characteristics inherently owned by the polypeptide (for instance, hydrophobicity, hydrophilicity, electric charge, pK and the like) are not substantially changed. For instance, it is preferable that the substitution of the amino acids is substitutions within each of the groups of: 1. glycine, alanine; 2. valine, isoleucine, leucine; 3. aspartic acid, glutamic acid, asparagine, glutamine; 4. serine, threonine; 5. lysine, arginine; 6. phenylalanine, tyrosine, and that deletion, addition or insertion of amino acids is deletion, addition or insertion in the amino acids having characteristics similar to the characteristics of the surroundings of the subject site in the polypeptide within the range that the characteristics of the surroundings of the subject site are not substantially changed.

The substitution or the like of the amino acids may be those naturally occurring being caused by difference between species or individuals, or may be artificially induced. Artificial induction may be carried out by a known method. The induction may be carried out by, for example, but not limited specifically to, preparing a given nucleic acid having substitution, deletion, addition or insertion of one or the plural number of nucleotides in the nucleic acid encoding the above-mentioned region or the given fragment derived from naturally occurring fibronectin, and using the nucleic acid to prepare a polypeptide comprising an amino acid sequence having substitution or the like in the amino acid sequence of the polypeptide constituting the above-mentioned region or given fragment derived from naturally occurring fibronectin, having a function equivalent to that of the fragment or the like, using a known method.

In addition, the phrase "having a function equivalent" herein refers to that the polypeptide, which is a comparative control, has at least any of the functions of (i) a function of enhancing or maintaining a cytotoxic activity of a cytotoxic lymphocyte, (ii) a function of enhancing an expression level of IL-2R, (iii) a function of improving a ratio of CD8-positive cell, or (iv) a function of improving expansion fold of a cytotoxic lymphocyte, each of which is possessed by the naturally occurring fibronectin fragment. The above-mentioned functions can be appropriately confirmed in accordance with the method described in Examples set forth below. In addition, as the fragment comprising a polypeptide having substitution or the like of amino acids, the fragment having a cell adhesion activity and/or a heparin binding activity is preferred. The cell adhesion activity and the heparin binding activity can be evaluated in accordance with the above-mentioned methods for determining those activities.

As the fragment comprising a polypeptide having substitution or the like of amino acids, for instance, a fragment having one or more amino acids inserted as a linker between two different domains can also be used in the present invention.

Incidentally, as the fibronectin, similarly to the above-mentioned fragment, there can be used in the present invention a polypeptide having an amino acid sequence having substitution, deletion, insertion or addition of one or the plural number of amino acids in an amino acid sequence constituting the polypeptide of the fibronectin, wherein the polypeptide has at least any of the functions of the above-mentioned (i) to (iv).

The fibronectin fragment as referred to herein can also be prepared from a genetic recombinant on the basis of the description of, for instance, U.S. Pat. No. 5,198,423. For instance, each of the fragments of H-271 (SEQ ID NO: 10), H-296 (SEQ ID NO: 11), CH-271 (SEQ ID NO: 12) and CH-296 (SEQ ID NO: 13) and a method of preparing these fragments are described in detail in the specification of this patent. In addition, CH-296Na (SEQ ID NO: 25) and the preparation method thereof are described in the section of (3) CH-296Na and Examples set forth below. In addition, the above-mentioned C-274 (SEQ ID NO: 9) fragment can be obtained in accordance with the method described in U.S. Pat. No. 5,102,988. Further, a C-CS1 (SEQ ID NO: 14) fragment can be obtained in accordance with the method described in Japanese Patent Gazette No. 3104178. Each of the fragment of CHV-89 (SEQ ID NO: 15), CHV-90 (SEQ ID NO: 16) or CHV-179 (SEQ ID NO: 18) can be obtained in accordance with the method described in Japanese Patent Gazette No. 2729712. In addition, the CHV-181 (SEQ ID NO: 19) fragment can be obtained in accordance with the method described in WO 97/18318. The CHV-92 (SEQ ID NO: 17) fragment can be obtained by genetic engineering technique using a plasmid constructed in a usual manner on the basis of the plasmid described in the literatures by referring to Japanese Patent Gazette No. 2729712 and WO 97/18318.

These fragments or fragments which can be derived from these fragments in a usual manner can be prepared by using microorganisms deposited to the International Patent Organism Depositary, National Institute of Advanced Industrial Science and Technology, Tsukuba Central 6, 1-1, Higashi 1-chome, Tsukuba-shi, Ibaraki-ken, Japan (Zip code 305-8566) under the following accession numbers, or by modifying a plasmid carried in each microorganism in accordance with a known method.

FERM BP-2264 (*Escherichia coli* carrying a plasmid encoding H-271,
  Date of Deposit: Jan. 30, 1989);
FERM BP-2800 (*Escherichia coli* carrying a plasmid encoding CH-296,
  Date of Deposit: May 12, 1989);
FERM BP-2799 (*Escherichia coli* carrying a plasmid encoding CH-271,
  Date of Deposit: May 12, 1989);
FERM BP-7420 (*Escherichia coli* carrying a plasmid encoding H-296,
  Date of Deposit: May 12, 1989);
FERM BP-1915 (*Escherichia coli* carrying a plasmid encoding C-274,
  Date of Deposit: Jun. 17, 1988);
FERM BP-5723 (*Escherichia coli* carrying a plasmid encoding C-CS1,
  Date of Deposit: Mar. 5, 1990);
FERM BP-10073 (*Escherichia coli* carrying a plasmid encoding CH-296Na,
  Date of Deposit: Jul. 23, 2004);
FERM P-12182 (*Escherichia coli* carrying a plasmid encoding CHV-89,
  Date of Deposit: Apr. 8, 1991); and
FERM P-12183 (*Escherichia coli* carrying a plasmid encoding CHV-179,
  Date of Deposit: Apr. 8, 1991).

Since the fibronectin is a gigantic glycoprotein, it is not necessarily easy to prepare and use a naturally occurring protein for the industrial purpose and for the purpose of the preparation of the medicament. In addition, since the fibronectin is a multifunctional protein, there may be considered some disadvantages caused by a region different from the region exhibiting the effect by the method of the present invention depending on the circumstances of its use. For these reasons, a fibronectin fragment can be preferably used in the present invention, more preferably a recombinant fibronectin fragment obtained as described above can be used from the viewpoints of availability, easy handling and safety. Further, there can be especially preferably used a fibronectin fragment which can exhibit an effect such as improvement in an expansion fold of a lymphocyte, increase in an expression level of IL-2R in an expanded lymphocyte, improvement in a ratio of CD8-positive cell in an expanded lymphocyte population, or increase in a cytotoxic activity as described below. In addition, the molecular weight of the fibronectin fragment used in the present invention is, but not particularly limited to, preferably from 1 to 200 kD, more preferably from 5 to 190 kD, even more preferably from 10 to 180 kD. The molecular weight can be determined, for example, by SDS-polyacrylamide gel electrophoresis.

Here, in the amino acid sequence of the polypeptide constituting the fibronectin fragment of the present invention, the partial amino acid sequence other than the amino acid sequence of the polypeptide constituting a naturally occurring fibronectin fragment is arbitrary and not limited specifically, so long as the exhibition of the desired effects of the present invention is not inhibited.

(2) Method for Preparing Cytotoxic Lymphocyte of the Present Invention

The method for preparing the cytotoxic lymphocyte of the present invention will be concretely explained below. The method of the present invention is a method for preparing a cytotoxic lymphocyte comprising the step of carrying out at least any one of induction, maintenance and expansion of a cytotoxic lymphocyte using a medium containing serum and plasma at a total concentration of 0% by volume or more and less than 5%, in the presence of the above-mentioned fibronectin, a fragment thereof or a mixture thereof.

The "cytotoxic lymphocyte" as used herein means a group of cells containing a cytotoxic lymphocyte. In a narrow sense, the cytotoxic lymphocyte may refer only to a cytotoxic lymphocyte contained in the above-mentioned group of cells in some cases. In addition, the preparation of the cytotoxic lymphocyte in the present invention encompasses any of induction from a precursor cell which can be formed into the cytotoxic lymphocyte of the present invention to a lymphocyte having a cytotoxic activity, maintenance of the cytotoxic lymphocyte, and expansion of the cytotoxic lymphocyte using the cytotoxic lymphocyte and/or the precursor cell. In the method for preparing a cytotoxic lymphocyte of the present invention, the kind of a cell subjected to the method, conditions for culture and the like are appropriately adjusted, to carry out induction, maintenance or expansion of the cytotoxic lymphocyte.

The cytotoxic lymphocyte of the present invention includes, but not particularly limited to, for instance, lymphokine-activated killer cell (LAK cell), cytotoxic T cell (CTL), tumor-infiltrating lymphocyte (TIL), NK cell and the like, each having a cytotoxic activity.

In the present invention, the precursor cell which can be formed into a cytotoxic lymphocyte, i.e., the precursor cell which has an ability of differentiating into the lymphocyte, is exemplified by peripheral blood mononuclear cell (PBMC), NK cell, naive cell, memory cell, hemopoietic stem cell, umbilical cord blood mononuclear cell and the like. In addition, so long as a cell is a hemocyte, the cell can be used as a precursor cell in the present invention. Any of these cells which are collected from a living body can be used directly or those which are subjected to frozen storage can be used. Incidentally, in the method for preparing a cytotoxic lymphocyte of the present invention, a material containing the above-mentioned cells, for instance, a blood such as peripheral blood or umbilical cord blood; one obtained by removing components such as erythrocyte and plasma from the blood; a marrow fluid and the like can be used.

One of the major characteristics of the method for preparing a cytotoxic lymphocyte of the present invention resides in that the cytotoxic lymphocyte is prepared in the presence of an effective ingredient selected from fibronectin, a fragment thereof or a mixture thereof. Here, the method for preparing a cytotoxic lymphocyte of the present invention is carried out during the entire period of culture of the cytotoxic lymphocyte, or during any part of the period. In other words, the present invention encompasses those embodiments which comprise the above-mentioned step in a part of the steps of preparing a cytotoxic lymphocyte.

Furthermore, while a conventional method for expanding a cytotoxic lymphocyte required addition of serum and plasma at 5 to 20% by volume in a medium, the method for preparing a cytotoxic lymphocyte of the present invention is characterized in that the total concentration of serum and plasma in a medium is 0% by volume or more and less than 5% by volume. The total concentration of serum and plasma in a medium can be set to be preferably 0% by volume or more and 4% by volume or less, and especially preferably 0% by volume or more and 3% by volume or less. In an especially preferred embodiment of the present invention, preparation of sufficient amount of cytotoxic lymphocyte can be carried out without adding serum or plasma to a medium at all, and is a very useful method from the viewpoint of security or amelioration of burden on a patient. In addition, in the present invention, when the amount of serum and plasma used is desired to be further reduced, the amount of serum and plasma used can be gradually reduced in the middle of culture. In other words, the amount of serum and plasma used can be reduced more than usual by reducing the concentration of serum and plasma in a fresh medium used upon dilution of a cell culture solution, exchange of a medium or exchange of a cell culture equipment described below, for the concentration of serum and plasma at initiation of the culture, or by not adding serum or plasma in the fresh medium. Therefore, the present invention provides a method for preparing a cytotoxic lymphocyte, comprising at least one step of diluting the cell culture solution, step of exchanging the medium or step of exchanging the cell culture equipment, wherein the total concentration of serum and plasma in the medium immediately after at least one step of diluting the cell culture solution, step of exchanging the medium or step of exchanging the cell culture equipment is same as that at initiation of culture or lowered as compared to that at initiation of culture.

Here, origin of the serum or plasma may be any of autologous (meaning that the origin of the cytotoxic lymphocyte used is same as that of the precursor cell) serum or plasma or nonautologous (meaning that the origin of the cytotoxic lymphocyte used is different from that of the precursor cell) serum or plasma. Preferably, autologous serum or plasma can be used, from the viewpoint of security.

In the method of the present invention, the preparation of a cytotoxic lymphocyte, i.e., the induction, maintenance and/or expansion of the cytotoxic lymphocyte is usually performed in a medium containing given components in the presence of the above-mentioned effective ingredient of the present invention.

For instance, in the method of the present invention, when the induction or expansion of the cytotoxic lymphocyte is intended, the number of cells (cytotoxic lymphocytes and/or precursor cells) at the initiation of culture used in the present invention is not particularly limited. For instance, the number of cells is exemplified by from 1 cell/mL to $1 \times 10^8$ cells/mL, preferably from 1 cell/mL to $5 \times 10^7$ cells/mL, and more preferably from 1 cell/mL to $2 \times 10^7$ cells/mL. In addition, the culture conditions are not particularly limited, and usual conditions for cell culture can be employed. For instance, cells can be cultured under the conditions of 37° C. in the presence of 5% $CO_2$ and the like. In addition, the medium can be diluted by adding a fresh medium, the medium can be exchanged, or the cell culture equipment can be exchanged at appropriate intervals.

The medium used in the method for preparing a cytotoxic lymphocyte of the present invention is not particularly limited except for the total concentration of serum and plasma, and a known medium prepared by mixing components necessary for maintaining and growing a cytotoxic lymphocyte or its precursor cell can be used. For instance, a commercially available medium can be appropriately selected to be used. These media may contain appropriate proteins, cytokines and other components in addition to the inherent constituents. Preferably, a medium containing IL-2 is used in the present invention. The concentration of IL-2 in the medium is, but not particularly limited to, for instance, preferably from 0.01 to $1 \times 10^5$ U/mL, more preferably from 0.1 to $1 \times 10^4$ U/mL.

As the cell culture equipment used in the method for preparing a cytotoxic lymphocyte of the present invention, for example, without particular limitation, a petri dish, a flask, a bag, a large culture bath, a bioreactor and the like can be used. Here, as a bag, a $CO_2$ gas-permeable bag for cell culture can be used as described in Examples 34 to 38 and 45 to 52 described below. In addition, upon industrial preparation of a large amount of cytotoxic lymphocytes, a large culture bath can be used. Furthermore, any of those of open system and closed system can be used for the culture. Preferably, the culture is carried out in those of closed system, from the viewpoint of security of the resulting lymphocyte.

In addition, a precursor cell which can be formed into a cytotoxic lymphocyte can be co-cultured in a medium further containing an anti-CD3 antibody. The concentration of the anti-CD3 antibody in a medium is, but not particularly limited to, for instance, preferably from 0.001 to 100 µg/mL, especially preferably from 0.01 to 100 µg/mL. The anti-CD3 antibody can be added for the purpose of activating a receptor on a lymphocyte. Also, besides the above, a lymphocyte-stimulating factor such as lectin can be added. The concentration of the component in a medium is not particularly limited, so long as the desired effects can be obtained.

Besides the coexistence of these components including an effective ingredient of the present invention, by dissolving the components in a medium, there may be used by immobilization on an appropriate solid phase, for instance, a cell culture equipment (including any of those of open system and closed system), such as a petri dish, a flask or a bag, or to a cell culture carrier such as beads, a membrane or a slide glass. Here, immobilization on beads can be carried out in accordance with the description of Examples 61 and 62 described below, and the prepared beads can be used in accordance with the description of Examples 63 and 64 described below. The materials for those solid phases are not particularly limited so long as the materials can be used for cell culture. When the components are immobilized on, for instance, the above-mentioned equipment, it is preferable to immobilize a given amount of each component on the amount of the medium to be placed in the equipment so that the medium has a similar proportion to a desired concentration of the case where the components are used by dissolving the components in a medium upon placing the medium in the equipment. The amount of the components immobilized is not particularly limited, so long as the desired effects can be obtained. The above-mentioned carrier is used by immersing the carrier in a culture medium in the cell culture equipment during the cell culture. When the above-mentioned components are immobilized on the above-mentioned carrier, it is preferable to immobilize a given amount of each component on the amount of the medium to be placed in the equipment so that the medium has a similar proportion to a desired concentration of the case where the components are used by dissolving the components in a medium upon placing the carrier in the medium. The amount of the components immobilized is not particularly limited, so long as the desired effects can be obtained.

For instance, the immobilization of the fibronectin fragment can be carried out in accordance with the methods described in WO 97/18318 and WO 00/09168.

Once various components mentioned above or the effective ingredient of the present invention is immobilized on the solid phase, the cytotoxic lymphocyte can be easily separated from the effective ingredient or the like after the lymphocyte is obtained by the method of the present invention only by separating the lymphocyte from the solid phase, so that the contamination of the effective ingredient into the lymphocyte can be prevented.

Furthermore, there may be used together with the above-mentioned components a compound selected from the group consisting of acidic polysaccharides, acidic oligosaccharides, acidic monosaccharides and salts thereof which are effective for induction of a cytotoxic T cell having an antigen-specific cytotoxic activity, described in WO 02/14481, or a substance selected from the following (A) to (D):

(A) a substance having a binding activity to CD44;
(B) a substance capable of regulating a signal emitted by binding of a CD44 ligand to CD44;
(C) a substance capable of inhibiting binding of a growth factor to a growth factor receptor; and
(D) a substance capable of regulating a signal emitted by binding of a growth factor to a growth factor receptor.

The above-mentioned substance having a binding activity to CD44 is exemplified by, for instance, a CD44 ligand and/or an anti-CD44 antibody. The substance capable of regulating a signal emitted by binding of a CD44 ligand to CD44 includes, for instance, various inhibitors or activators for phosphoenzymes and dephosphorylases. The substance capable of inhibiting binding of a growth factor to a growth factor receptor includes, for instance, a substance having a binding activity to a growth factor and forming a complex with the growth factor, thereby inhibiting the binding of the growth factor to a growth factor receptor, or a substance having a binding activity to a growth factor receptor, thereby inhibiting the binding of the growth factor to a growth factor receptor. Furthermore, the substance capable of regulating a signal emitted by binding of a growth factor to a growth factor receptor includes, for instance, various inhibitors or activators for phosphoenzymes and dephosphorylases. The concentration of these components in the medium is not particularly limited, so long as the desired effects can be obtained. Also, these components may be used by immobilization on the appropriate solid phase as mentioned above in addition to the coexistence of these components in the medium by dissolving the components in the medium.

Here, each of various substances mentioned above can be used alone or in admixture of two or more kinds.

In the present invention, the phrase "in the presence of the above-mentioned effective ingredient" refers to the fact that the above-mentioned effective ingredient is present in a state that the effective ingredient can exhibit its function when the induction, maintenance or expansion of the cytotoxic lymphocyte is carried out, and the existing manner is not particularly limited. For instance, when the effective ingredient is dissolved in the medium to be used, the content of the effective ingredient of the present invention in the medium in which culture is carried out is not particularly limited, so long as the desired effects are obtained. The content of the effective ingredient is, for instance, preferably from 0.0001 to 10000 µg/mL, more preferably from 0.001 to 10000 µg/1 mL, even more preferably 0.005 to 5000 µg/mL, especially preferably from 0.01 to 1000 µg/mL.

When the expression level of IL-2R is determined for the cytotoxic lymphocyte obtained by the method of the present invention, a significant increase in expression level of IL-2R is recognized as compared to a cytotoxic lymphocyte obtained by carrying out at least any one of induction, maintenance and expansion in the absence of fibronectin, a fragment thereof or a mixture thereof. Here, the expression level of IL-2R can be determined by a known method, for instance, using an anti-IL-2R antibody.

As described above, the cytotoxic lymphocyte obtained by the method of the present invention has an increased expression level of IL-2R. IL-2R is an activation marker which is expressed on a surface of an activated T cell, and with the expression of this molecule, cytokine production, cytotoxic activity, proliferation activation or the like is activated. Therefore, the cytotoxic lymphocyte obtained by the method of the present invention is a group of cells having a high function.

In addition, since the cytotoxic lymphocyte obtained by the method of the present invention has an increased expression level of IL-2R, the cytotoxic lymphocyte has an increased sensitivity to a stimulation by IL-2 added to a medium, or IL-2 produced by a precursor cell of a cytotoxic lymphocyte, a lymphocyte itself or other coexisting cell. For this reason, the cytotoxic lymphocyte can be activated by itself even under the environment of a smaller amount of IL-2 (for instance, in a living body or the like).

Further, in the cytotoxic lymphocyte obtained by the method of the present invention, the existence ratio of (CD8-positive) cell having a CD8 marker is high as compared to that of the cytotoxic lymphocyte obtained by carrying out at least any one of induction, maintenance and expansion in the absence of fibronectin, a fragment thereof or a mixture thereof. This fact has some advantages, for instance, 1. that the CD8-positive cell produces a cytokine such as interferon-γ, thereby causing immunological activation to change a helper T cell balance into the Th1 dominant system, 2. that the CD8-positive cell is a cellular immunocyte that can efficiently exclude a foreign substance such as a virus or a tumor cell, 3. that when the CD8-positive cell is obtained, the CD8-positive cell can be enriched with culturing the cell in accordance with the method of the present invention, while the CD8-positive cell has been conventionally purified with magnet beads or a flow cytometer, 4. that the cytotoxic lymphocyte is suitably used as a precursor cell during the induction of CTL, because the ratio of the CD8-positive cell is high, 5. that even a cell population having a lower ratio of the CD8-positive cell can be cultured with increasing the ratio of the CD8-positive cell and the like. Therefore, the method of the present invention is very useful in the preparation of a cytotoxic lymphocyte.

Here, the ratio of the CD8-positive cell in the cytotoxic lymphocyte obtained by the method of the present invention can be determined by, for instance, but not particularly limited to, using an anti-CD8 antibody.

In addition, the cytotoxic lymphocyte prepared according to the method of the present invention has an excellent characteristic that high cytotoxic activity as previously observed is maintained, even when a cell after the culture is maintained over a long period of time, or the cell is proliferated. In other words, the cytotoxic lymphocyte maintains a high cytotoxic activity as compared to a cytotoxic lymphocyte obtained by carrying out at least any one of induction, maintenance and expansion in the absence of fibronectin, a fragment thereof or a mixture thereof. Therefore, there can be maintained as a lymphocyte having a stable cytotoxic activity by cloning the cultured cytotoxic lymphocyte. In addition, the induced cytotoxic lymphocyte can be proliferated and expanded by stimulating the cytotoxic lymphocyte with an antigen, various kinds of cytokines, or an anti-CD3 antibody. A known method can be used for the maintenance or expansion of the cytotoxic lymphocyte without being particularly limited.

The maintenance of the above-mentioned cytotoxic lymphocyte refers to the maintenance of the cytotoxic lymphocyte with keeping its cytotoxic activity. The culture conditions during the maintenance are not particularly limited, and the conditions used for ordinary cell culture can be used. For instance, the cells can be cultured under the conditions of 37° C. in the presence of 5% $CO_2$, and the like. In addition, the medium can be exchanged with a fresh one at appropriate time intervals. The medium to be used and other components simultaneously used therewith and the like are the same as those mentioned above.

One of the major characteristics of the maintenance and expansion of the cytotoxic lymphocyte in the method of the present invention resides in that the method comprises respectively continuously culturing and expanding the cytotoxic lymphocyte in a medium containing serum and plasma at a total concentration of 0% by volume or more and less than 5% by volume, in the presence of the effective ingredient of the present invention, i.e. fibronectin, a fragment thereof or a mixture thereof. According to the expansion, the cell number of the cytotoxic lymphocyte can be increased in a state that the cytotoxic activity owned by the cytotoxic lymphocyte is maintained. In other words, as one embodiment of the method of the present invention, there is provided a method for expanding a cytotoxic lymphocyte.

The cytotoxic lymphocyte obtained by the method of the present invention has an ability to recognize a desired target cell, and for example, destroys the cell which is to be the target by its cytotoxic activity. The cytotoxic activity of the cytotoxic lymphocyte can be assessed by a known method. For example, the cytotoxic activity of the cytotoxic lymphocyte to a target cell labeled with a radioactive substance, a fluorescent substance or the like can be assessed by determining radioactivity or fluorescence intensity from the target cell destroyed by the cytotoxic lymphocyte. The cytotoxic activity can also be detected by determining the amount of cytokine such as GM-CSF or IFN-γ specifically released from a cytotoxic lymphocyte or the target cell. In addition, the cytotoxic activity can be directly confirmed by use of an antigenic peptide-MHC complex labeled with a fluorescent dye and the like. In this case, the cytotoxic activity of the cytotoxic lymphocyte can be assessed, for example, by contacting a cytotoxic lymphocyte with a first fluorescent marker coupled with a cytotoxic lymphocyte-specific antibody, followed by contacting with an antigenic peptide-MHC complex coupled with a second fluorescent marker, and carrying out FACS (fluorescence-activated cell sorting) analysis on the presence of double-labeled cell.

Further, the method for preparing a cytotoxic lymphocyte of the present invention has the feature that the culture can be initiated at a low number of cells. A large amount of lymphocytes is required in order to carry out adopted immunotherapy, but it is difficult to obtain a large amount of lymphocytes from a patient. In addition, in an ordinary expansion of the cytotoxic lymphocyte, there have been necessitated selection of a cell culture equipment having an appropriate culture area depending upon the number of cells to be used, and culture at an appropriate amount of the medium. In other words, usually, the culture is initiated under the high density conditions that the amount (number) of cells to a culturing area in a cell culture equipment [i.e. area ($cm^2$) of a surface area of the equipment contacting with the medium] is $1 \times 10^6$ cells/$cm^2$ or more, and the cell concentration is $1 \times 10^6$ cells/mL or more. When the culture is carried out under the conditions below this cell level, an expansion fold [a ratio of the number of cells after the expansion to the number of cells before the expansion (the number of cells after expansion/the number of cells before expansion)] becomes very low, whereby requiring a long-term culture period before the cytotoxic lymphocytes are obtained in a large amount. Therefore, generally, a large number of lymphocytes are currently prepared by, for instance, initiating the culture using a small cell culture equipment, and thereafter using a stepwise, large-scaled cell culture equipment, or a method of increasing the number of cell culture equipments and repeating dilution procedures. As described above, a plurality of culture systems are required in the ordinary expansion of the cytotoxic lymphocyte.

According to the method of the present invention, even when initiated with a small amount of cells, the cell can be cultured with a high expansion fold regardless of the size of a cell culture equipment. Therefore, a complicated procedure which has been conventionally conducted, such as an exchange of the cell culture equipment or the cell culture solution and the dilution procedures of the cell culture solution, become unnecessary. In other words, according to the method of the present invention, the expansion of the cytotoxic lymphocyte can be satisfactorily carried out by culture procedures using one cell culture equipment, i.e., one culture system. Therefore, according to the method of the present invention, a method for preparing a cytotoxic lymphocyte which does not require the step of diluting the cell culture solution can be accomplished. Especially, when LAK cell is expanded according to the method of the present invention, LAK cell can be expanded by adding a precursor cell which can be formed into a LAK cell and a medium to a large-volume cell culture equipment, and adding only IL-2 thereto in subsequent steps. The present invention is very useful in the aspect that a large amount of LAK cell can be obtained by a simple procedure. Here, the fibronectin fragment can be preferably used as the effective ingredient of the present invention to be used from the viewpoint of obtaining a higher expansion fold. As described above, according to the method of the present invention, a necessary amount of the cytotoxic lymphocyte can be obtained in a shorter time period.

For instance, when at least any one of induction, maintenance and expansion of a cytotoxic lymphocyte is initiated at a low number of cells in a cell culture equipment containing a medium in the presence of the effective ingredient of the present invention, the induction, maintenance or expansion can be carried out by using an amount of the cell satisfying the conditions selected from the followings (a) and (b) at a low concentration or low density at the initiation of culture:

(a) a ratio of the amount of cells to the culture area in the cell culture equipment to be used being preferably from 1 cell/$cm^2$ to $5\times10^5$ cells/$cm^2$, more preferably from 10 cells/$cm^2$ to $1\times10^5$ cells/$cm^2$, especially preferably from $1\times10^2$ cells/$cm^2$ to $5\times10^4$ cells/$cm^2$; and (b) a concentration of the cells in the medium being preferably from 1 cell/mL to $5\times10^5$ cells/mL, more preferably from 10 cells/mL to $1\times10^5$ cells/mL, and especially preferably from $1\times10^2$ cells/mL to $5\times10^4$ cells/mL.

The amount of cells as used herein refers to the number of cytotoxic lymphocytes and/or precursor cells.

In addition, in the method of the present invention, there can be exemplified a method comprising carrying out at least any one of induction, maintenance and expansion of a cytotoxic lymphocyte in one culturing system, which does not require the step of dilution procedure of the cell culture solution.

Furthermore, the method for preparing a cytotoxic lymphocyte of the present invention has the feature that the culture can also be carried out at a large number of cells. In other words, in the case where a method for preparing a cytotoxic lymphocyte in a cell culture equipment including a medium includes at least one step of diluting the cell culture solution with a fresh medium, step of exchanging the medium, or step of exchanging the cell culture equipment during the culture, even when the culture conditions immediately after these steps are set to be at a high concentration (for example, the concentration of the cells in the cell culture solution being from $2\times10^5$ cells/mL to $1\times10^8$ cells/mL, preferably from $2\times10^5$ cells/mL to $5\times10^7$ cells/mL, more preferably from $2\times10^5$ cells/mL to $2\times10^7$ cells/mL) or at a high density (for example, the ratio of the number of the cells in the cell culture solution to the culture area in the cell culture equipment being from $1\times10^5$ cells/$cm^2$ to $1\times10^8$ cells/$cm^2$, preferably from $1\times10^5$ cells/$cm^2$ to $5\times10^7$ cells/$cm^2$, more preferably from $1\times10^5$ cells/$cm^2$ to $2\times10^7$ cells/$cm^2$), the method of the present invention can accomplish a good expansion fold as compared to that of the conventional method. In usual expansion of a cytotoxic lymphocyte, the number of the cells at the initiation of culture is often set to be at a comparably high concentration or high density, and the cell concentration in the cell culture solution or the cell density in the cell culture equipment is set to be low, in accordance with increase in proliferation ratio of the cells. The culture at a large number of cells of the present invention refers to preparation of a cytotoxic lymphocyte of which conditions are set to be at a high concentration or at a high density, wherein the concentration of cells in the cell culture solution is from $2\times10^5$ cells/mL to $1\times10^8$ cells/mL, or the ratio of the number of cells in the cell culture solution to the culture area in the cell culture equipment is from $1\times10^5$ cells/$cm^2$ to $1\times10^8$ cells/$cm^2$ upon setting the cell concentration or cell density during the culture. Here, as used herein, the expression "immediately after the step of diluting the cell culture solution with a fresh medium, step of exchanging the medium, or step of exchanging the cell culture equipment" does not comprise the initiation of the culture.

Advantages of being able to carrying out the culture at a large number of cells as described above include reduction in the amount of the medium, the medium additives such as serum and plasma, the cell culture equipment which are used, labor, and space for the culture. Adoptive immunotherapy needs a large amount of lymphocytes, thereby needs a very large amount of medium or cell culture equipment to be used. Accordingly, it requires an extensive space for the culture and labor. The above is to be a great problem for spread of adoptive immunotherapy. Therefore, since the method of the present invention can solve the problem as described above, it is a very creative invention for institution or management of a facility.

As previously described, the method of the present invention can be applied to any of cell culture at a low concentration or low density, or cell culture at a high concentration or high density. Therefore, use of the method of the present invention enables preparation of a cytotoxic lymphocyte at various cell concentrations or cell densities, depending on culture conditions.

In addition, in the method of the present invention, the cell can be co-cultured with an appropriate feeder cell. When the cytotoxic lymphocyte is co-cultured with the feeder cell, it is desired that the medium is one that is suitable for maintenance and growth of both the cytotoxic lymphocyte and the feeder cell. As the medium, a commercially available medium can be used.

The feeder cell used for the method of the present invention is not particularly limited, so long as the feeder cell stimulates cytotoxic lymphocyte cooperatively with an anti-CD3 antibody to activate T cell receptor. In the present invention, for instance, PBMC or B cell transformed with Epstein-Barr virus (EBV-B cell) is used. Usually, a feeder cell is used after its proliferating ability is taken away by means of irradiation or the like. Incidentally, the content of the feeder cell in the medium may be determined according to the known method. For instance, the content is preferably from $1\times10^5$ cells/mL to $1\times10^7$ cells/mL.

In a particularly preferred embodiment of the present invention, non-virus-infected cell, for instance, a cell other than EBV-B cell, is used as a feeder cell. By using the non-virus-infected cell, the possibility that EBV-B cell is admixed in an expanded cytotoxic lymphocyte can be eliminated, thereby making it possible to increase the safety in medical treatments utilizing cytotoxic lymphocyte, such as adoptive immunotherapy.

In addition, in the method of the present invention, the cell can also be co-cultured with an appropriate antigen-presenting cell. The antigen-presenting cell can be prepared by adding an antigenic peptide to a cell having an antigen-presenting ability, thereby allowing the cell to present the antigenic peptide on its surface [see, for instance, Bendnarek M. A., et al., *J. Immunol.*, 147(12), 4047-4053 (1991)]. In addition, in the case where a cell having an antigen-presenting ability has an ability to process an antigen, an antigen is added to the cell, whereby the antigen is incorporated into the cell and processed therein, and fragmented antigenic peptides are presented on the cell surface. Incidentally, when an antigenic peptide is added to a cell having an antigen-presenting ability, an antigenic peptide matching the MHC restriction or an antigenic peptide which is not restricted by the MHC of the antigen-presenting cell used and the cytotoxic lymphocyte to be induced is used.

Incidentally, the antigen used in the present invention is not particularly limited, and includes, for instance, exogenous antigens such as bacteria and viruses, endogenous antigens such as tumor-associated antigens (cancer antigens), and the like.

In the present invention, it is preferable that the antigen-presenting cell is made non-proliferative. In order to make the cell non-proliferative, the cell may be, for instance, subjected to irradiation with X-ray or the like, or a treatment with an agent such as mitomycin.

When LAK cell is prepared by the preparation method of the present invention, the culture of LAK cell is carried out by incubating a precursor cell which can be formed into LAK cell together with IL-2 in the presence of the above-mentioned effective ingredient. The precursor cell which can be formed into LAK cell includes, but not particularly limited to, for instance, peripheral blood mononuclear cell (PBMC), NK cell, umbilical cord blood mononuclear cell, hemopoietic stem cell, blood components containing these cells, and the like.

In addition, the general conditions for culturing LAK cell may be set in accordance with the known conditions [for instance, see *Saibo Kogaku* (Cell Technology), 14(2), 223-227, (1995); Saibo Baiyo (*Cell Culture*) 17(6), 192-195, (1991); *THE LANCET*, 356, 802-807, (2000); *Current Protocols in Immunology*, supplement 17, UNIT 7.7], except that the above-mentioned medium is used. The culture conditions are not particularly limited, and the conditions which are used in ordinary cell culture can be employed. For instance, the culture can be carried out under the conditions of 37° C. in the presence of 5% $CO_2$, and the like. This co-culture is usually carried out for about 2 to about 15 days. In addition, the step of diluting the cell culture solution, the step of exchanging the medium, or the step of exchanging the cell culture equipment can be carried out at appropriate intervals.

In the same manner as those for the above-mentioned induction, maintenance or expansion of the LAK cell, as to CTL and TIL, a group of cells having a high cytotoxic activity can be prepared by culturing the cells in the presence of fibronectin, a fragment thereof or a mixture thereof. In the present invention, there is no particular limitation in the procedures of activating these cells so long as fibronectin, a fragment thereof or a mixture thereof is coexistent therewith and a medium containing serum and plasma at a total concentration of 0% by volume or more and less than 5% by volume is used. The procedures can be carried out using a medium appropriate for culture or activation of the above-mentioned cells. As to the amount of fibronectin, a fragment thereof or a mixture thereof used, the method of adding the component and the like, appropriate ones may be selected in accordance with the above-mentioned method.

Here, the method for expanding a cytotoxic lymphocyte of the present invention is not limited particularly, so long as the above-mentioned effective ingredient is present in the culture system used in the method, and the total concentration of serum and plasma in the medium is 0% by volume or more and less than 5% by volume. The present invention encompasses those embodiments wherein the above-mentioned effective ingredient is present in the culture system, and wherein the total concentration of serum and plasma in the medium is 0% by volume or more and less than 5% by volume in the conventional method for expanding a cytotoxic lymphocyte other than those described above.

Diseases to which the cytotoxic lymphocyte prepared by the method of the present invention is administered are exemplified by, but not limited specifically to, for example, cancer, malignant tumor, hepatitis, or infectious diseases such as influenza, caused by a virus, a bacteria or a fungus. In addition, when a foreign gene is further introduced thereto as described below, the effects can be also expected for various genetic diseases. The cytotoxic lymphocyte prepared by the method of the present invention can also be utilized for donor lymphocyte infusion and the like for the purpose of prevention from an infectious disease after bone marrow transplantation or X-ray irradiation.

In another embodiment of the present invention, there is provided a medium for culturing a cytotoxic lymphocyte, comprising as an effective ingredient fibronectin, a fragment thereof or a mixture thereof, wherein the total concentration of serum and plasma in the medium is 0% by volume or more and less than 5% by volume. The medium further comprises other optional ingredient, for instance, a medium component, a protein, and a cytokine (preferably IL-2), which are used for known cell culture, and other desired components. Here, the medium can be prepared in accordance with a known method, using the effective ingredient of the present invention, and autologous or nonautologous serum or plasma so as to have a total concentration of 0% by volume or more and less than 5% by volume in the medium. The content of the effective ingredient of the present invention and the like in the medium is not limited particularly, so long as the desired effects of the present invention can be obtained. The content can be appropriately determined as desired, for example, in accordance with the content of the effective ingredient and the like in the above-mentioned medium used in the method of the present invention. One embodiment of the medium of the present invention encompasses a medium containing a cell culture carrier to which fibronectin, a fragment thereof or a mixture thereof is immobilized and a medium provided being included in the cell culture equipment to which fibronectin, a fragment thereof or a mixture thereof is immobilized.

Usually, in the lymphocyte-containing culture obtained by using the method for preparing a cytotoxic lymphocyte as described above, cells other than cytotoxic lymphocyte such as helper T cell are admixed therein. However, since lymphocytes having a cytotoxic activity are contained in a large amount in the lymphocyte-containing culture obtained by the present invention, the cells in the culture can be harvested from the culture by centrifugation or the like, and directly used as a cytotoxic lymphocyte obtained by the method of the present invention. Moreover, if the above-mentioned effective ingredient or the like is immobilized on a cell culture equipment or the like, there is no risk of admixture of the component or the like in the resulting cytotoxic lymphocyte.

In addition, a cell population (or culture) rich in a cytotoxic lymphocyte can be further separated from the culture by a known method, and used as a cytotoxic lymphocyte obtained by the method of the present invention. In other words, the method for preparing a cytotoxic lymphocyte of the present invention can comprise the step of selecting a cell population rich in a cytotoxic lymphocyte from the culture obtained by the method.

The method of selecting a cell population rich in a cytotoxic lymphocyte is not particularly limited. The method is exemplified by, for instance, a method comprising selectively collecting only the desired cell from the culture using a cell culture equipment or carrier to which an antibody against a cell surface antigen expressed on the desired cell surface, for instance, an anti-CD8 antibody, is bound, or a method using a flow cytometer. The above-mentioned carrier is exemplified by magnetic beads or a column. In addition, the cell population rich in the desired cell can be obtained by removing by adsorbing out cells other than the desired cell from the culture. For instance, the helper T cell can be removed from the lymphocyte culture using an antibody against a cell surface antigen expressed on a surface of the helper T cell, for instance, an anti-CD4 antibody. In this step, a flow cytometer can be also used.

Further, the present invention provides a cytotoxic lymphocyte obtained by the method for preparing a cytotoxic lymphocyte of the present invention mentioned above. The lymphocyte has a high cytotoxic activity, which has a characteristic that there is little lowering of the cytotoxic activity, even when the lymphocyte is subjected to the continuous culture or expansion over a long period of time. In addition, the present invention provides a medicament (therapeutic agent) comprising the lymphocyte as an effective ingredient. Especially, the above-mentioned therapeutic agent comprising the lymphocyte is suitably used in adoptive immunotherapy. In the adoptive immunotherapy, the lymphocyte having a cytotoxic activity suitable for treating a patient is administered to the patient by, for instance, intravenous administration. The therapeutic agent is very useful for use in the above-mentioned diseases or donor lymphocyte infusion. The therapeutic agent can be prepared by, for instance, blending the lymphocyte prepared by the method of the present invention as an effective ingredient with, for instance, a known organic or inorganic carrier suitable for non-oral administration, an excipient, a stabilizing agent and the like, according to a method known in the pharmaceutical field. Incidentally, various conditions for the therapeutic agent, such as the content of lymphocyte of the present invention in the therapeutic agent and the dose of the therapeutic agent, can be appropriately determined according to the known adoptive immunotherapy.

The method for preparing a cytotoxic lymphocyte of the present invention can further comprise the step of transducing a foreign gene into the lymphocyte. In other words, one embodiment of the present invention provides a method for preparing a cytotoxic lymphocyte, further comprising the step of transducing a foreign gene into a cytotoxic lymphocyte. Here, the term "foreign" refers to those which are foreign to a lymphocyte into which a gene is to be transduced.

By carrying out the method for preparing a cytotoxic lymphocyte of the present invention, especially the method for expanding a cytotoxic lymphocyte, the ability for proliferation of the cultured lymphocyte is enhanced. Therefore, by combining the method for preparing a cytotoxic lymphocyte of the present invention with the step of transducing a gene, increase in the gene-transducing efficiency is expected.

Methods of transducing a foreign gene are not particularly limited, and an appropriate method can be selected from a known method for transducing a gene. The step of transducing a gene can be carried out at any given point during the preparation of a cytotoxic lymphocyte. For instance, it is preferable to carry out the step simultaneously with any step of the above-mentioned induction, maintenance and/or expansion of the lymphocyte or after the step, from the viewpoint of working efficiency.

As the above-mentioned method for transducing a gene, any of methods using a viral vector, and methods without using the vector can be employed in the present invention. The details of those methods have been already published in numerous literatures.

The above-mentioned viral vector is not particularly limited, and a known viral vector ordinarily used in the method for transducing a gene, for instance, retroviral vector, lentiviral vector, adenoviral vector, adeno-associated viral vector, simian viral vector, vaccinia viral vector, sendai viral vector, or the like is used. Especially preferably, as the viral vector, retrovirus, adenovirus, adeno-associated virus or simian virus is used. As the above-mentioned viral vector, those lacking replication ability so that the viral vector cannot self-replicate in an infected cell are preferable.

The retroviral vector is used for the purpose of gene therapy or the like because there can be stably incorporated a foreign gene inserted into the vector in chromosomal DNA in the cell into which the vector is to be transduced. Since the vector has a high infection efficiency to the cell during mitosis and proliferation, the gene transduction is preferably carried out in the step for preparing a cytotoxic lymphocyte, for instance, the step of expansion.

As the method for transducing a gene without using a viral vector, there can be employed, but not particularly limited to, for instance, a method using a carrier such as liposome or ligand-polylysine, calcium phosphate method, electroporation method, particle gun method or the like. In this case, there is transduced a foreign gene incorporated into plasmid DNA or linear DNA.

The foreign gene to be transduced into a cytotoxic lymphocyte in the present invention is not particularly limited, and an arbitrary gene which is desired to be transduced into the above-mentioned cell can be selected. As the gene as described above, besides a gene encoding a protein (for instance, an enzyme, a cytokine, a receptor or the like), for instance, a gene encoding an antisense nucleic acid, siRNA (small interfering RNA) or a ribozyme can be used. In addition, an appropriate marker gene which is capable of selecting a cell into which a gene is transduced may be transduced simultaneously.

The above-mentioned foreign gene can be, for instance, inserted into a vector, a plasmid or the like, so that the foreign gene is expressed under the control of an appropriate promoter, and used. In addition, in order to achieve an efficient transcription of a gene, there may exist in a vector other regulating element which cooperates with a promoter or a transcription initiation site, for instance, an enhancer sequence or a terminator sequence. In addition, for the purpose of inserting a foreign gene into a chromosome of a lymphocyte in which the gene is transduced by homologous recombination, for instance, a foreign gene may be arranged between flanking sequences comprising nucleotide sequences each having homology to nucleotide sequences located on both sides of the desired target insertion site of the gene in the chromosome. The foreign gene to be transduced may be one that is a naturally occurring or an artificially generated, or may be one in which DNA molecules having different origins from each other are bound by a known means such as ligation. Moreover, the foreign gene may be one having a sequence in which a mutation is introduced into a naturally occurring sequence depending upon its purpose.

According to the method of the present invention, for instance, a gene encoding an enzyme associated with the resistance to a drug used for the treatment of a patient with cancer or the like can be transduced into a cytotoxic lymphocyte, thereby giving the lymphocyte a drug resistance. If the cytotoxic lymphocyte as described above is used, adoptive immunotherapy and drug therapy can be combined, and, therefore, higher therapeutic effects can be obtained. The drug resistance gene is exemplified by, for instance, a multidrug resistance gene.

On the other hand, conversely to the above-mentioned embodiment, a gene so as to give a sensitivity against a particular drug can be transduced into a cytotoxic lymphocyte, thereby giving sensitivity against the drug. In this case, the lymphocyte after being transplanted to a living body can be removed by administering the drug. The gene for giving sensitivity against a drug is exemplified by, for instance, a thymidine kinase gene.

(3) CH-296Na

In the present invention, there are also provided a novel polypeptide having the amino acid sequence (x) shown in SEQ ID NO: 25 (CH-296Na) of Sequence Listing, or a polypeptide having an amino acids sequence (y) having deletion, insertion, addition or substitution of one or the plural number of amino acids in the amino acid sequence (x), wherein the polypeptide having the amino acid sequence (y) has a function equivalent to that of the polypeptide having the amino acid sequence (x), and a nucleic acid encoding the novel polypeptide. The nucleic acid is exemplified by a nucleic acid comprising (1) a DNA comprising the nucleotide sequence shown in SEQ ID NO: 26 (a nucleic acid encoding CH-296Na); (2) a DNA encoding a polypeptide comprising a nucleotide sequence having deletion, substitution, insertion or addition of one or the plural number of nucleotides in the nucleotide sequence shown in SEQ ID NO: 26, wherein the polypeptide has a function equivalent to that of the polypeptide encoded by the DNA (1); or (3) a DNA which hybridizes to a DNA comprising the nucleotide sequence shown in SEQ ID NO: 26 under stringent conditions, which encodes a polypeptide having a function equivalent to that of the polypeptide encoded by the DNA (1).

Here, in the present specification, the novel polypeptide is referred to as the polypeptide of the present invention, and the nucleic acid encoding the polypeptide is referred to as the nucleic acid of the present invention, in some cases.

Hereinafter, the polypeptide of the present invention, the nucleic acid encoding the polypeptide, and the method for preparing the polypeptide will be described.

The polypeptide of the present invention includes those having an amino acid sequence having one or more of substitution, deletion, insertion or addition of one or the plural number of amino acids in the above-mentioned amino acid sequence, so long as the polypeptide has any of the desired functions [functions of the above-mentioned (i) to (iv)] in the preparation of a cytotoxic lymphocyte as mentioned above. The polypeptide of the present invention other than CH-296Na is exemplified by a polypeptide having one or more of any of substitution, deletion, insertion or addition of preferably 1 to 20 amino acids, more preferably 1 to 10 amino acids, and further preferably 1 to 5 amino acids in the amino acid sequence shown in SEQ ID NO: 25 of Sequence Listing. Here, substitution or the like of an amino acid can be carried out to an extent where it can change physicochemical characteristics and the like of an inherent polypeptide within the range where the function of the polypeptide can be maintained. The detail and the method for preparing the polypeptide is as described above.

The nucleic acid shown in SEQ ID NO: 26 of Sequence Listing encoding the polypeptide of the present invention can be obtained as a DNA fragment encoding CH-296Na by carrying out PCR using a cDNA encoding human fibronectin derived from plasma as a template. As a primer used in the PCR is not limited specifically. For example, Primer CH-296Na1 or Primer CH-296Na2 shown in SEQ ID NO: 27 or 28 of Sequence Listing can be used as the primer. In addition, the nucleic acid can be obtained by binding a plasmid of the above-mentioned FERM BP-2800 (*Escherichia coli* carrying a plasmid encoding CH-296) and a DNA fragment having a sequence which is present between a cell binding domain and heparin binding domain of a native fibronectin derived from plasma (11 of the type III repetitive sequence in FIG. 1) using appropriate restriction site.

In addition, the nucleic acid of the present invention also includes a nucleic acid having one or more of any of substitution, deletion, insertion or addition of one or the plural number of nucleotide in the nucleotide sequence of the nucleic acid shown in SEQ ID NO: 26 of Sequence Listing. For example, the nucleic acid is exemplified by a nucleic acid having one or more of any of substitution, deletion, insertion or addition of 1 to 60 nucleotides, more preferably 1 to 30 nucleotides, further preferably 1 to 15 nucleotides in the nucleotide sequence shown in SEQ ID NO: 26 of Sequence Listing. Here, substitution or the like of a nucleotide can be carried out to an extent where it can change physicochemical characteristics of a polypeptide and the like encoded by the nucleic acid within the range where the function of the polypeptide can be maintained. The detail and the method for substitution or the like of a nucleotide are pursuant to the description for those of the above-mentioned substitution or the like of an amino acid.

Furthermore, the nucleic acid of the present invention includes a nucleic acid, which hybridizes to a nucleic acid comprising the nucleotide sequence shown in SEQ ID NO: 26 under stringent conditions, and which encodes a polypeptide having a function equivalent to that of the polypeptide of the present invention, i.e., at least any of the functions of the (i) to (iv) in the preparation of the cytotoxic lymphocyte mentioned above. The "stringent conditions" are not limited specifically, and can be set by appropriately determining temperature and salt concentration upon hybridization, preferably additionally upon washing, depending on the DNA which hybridizes to the DNA comprising the nucleotide sequence shown in SEQ ID NO: 26. The stringent conditions include, for example, the conditions described in a literature such as Sambrook et al., *Molecular cloning, A laboratory manual* $3^{rd}$ edition, 2001, published by Cold Spring Harbor Laboratory Press.

Specifically, for example, the stringent conditions are exemplified by incubation at 50° C., preferably at 65° C., in a solution containing 6×SSC (1×SSC being 0.15 M NaCl, 0.015 M sodium citrate, pH 7.0), 0.5% SDS, 5×Denhardt's (0.1% bovine serum albumin (BSA), 0.1% polyvinyl pyrrolidone, 0.1% Ficoli 400) and 100 µg/mL salmon sperm DNA. When Tm value of the DNA used is known, the above-mentioned temperature may be lower than that value by 5 to 12° C. Furthermore, conditions, such as carrying out the step of removing the DNA hybridizing non-specifically by washing, wherein from the viewpoint of improving accuracy, washing is carried out under conditions of, for example, 2×SSC, more stringently 0.1×SSC and the like and/or conditions of higher temperature, such as 25° C. or more, more stringently 37° C. or more, further stringently 42° C. or more, even more stringently 50° C. or more, varying depending on the Tm value of the DNA used, may be added.

The present invention also encompasses a nucleic acid molecule which hybridizes to the polynucleotide of the present invention under lower stringent conditions. Variation of stringency of the hybridization and signal detection is carried out mainly by manipulation of form amide concentration (lower percentile of formamide causes lowered stringency), salt concentration or temperature. For example, lower stringent conditions include overnight incubation at 37° C. in a solution containing 6×SSPE (20×SSPE=3 M NaCl; 0.2 M NaH$_2$PO$_4$; 0.02 M EDTA, pH 7.4), 0.5% SDS, 30% formamide, 100 µg/mL salmon sperm blocking DNA; followed by washing with 1×SSPE and 0.1% SDS at 50° C. Furthermore, in order to accomplish lower stringency, the washing carried out after the stringent hybridization can be carried out at a higher salt concentration (for example, 5×SSC).

The above-mentioned conditions can be modified by adding and/or substituting an alternative blocking reagent used for suppressing background in a hybridization experiment. Typical blocking reagent includes Denhardt's reagent, BLOTTO, heparin, denatured salmon sperm DNA and commercially available product formulation. In addition, other elements other than the above-mentioned hybridization conditions are needed to be modified depending on such modification, in some cases.

On the other hand, a polypeptide having the amino acid sequence shown in SEQ ID NO: 25 of Sequence Listing can be obtained by genetic engineering technique, using the nucleic acid this obtained. In other words, the polypeptide can be obtained by inserting the nucleic acid into an appropriate expression vector including, but not being limited specifically to, pET vector, pCold vector and the like, to express the polypeptide by a known method, for example, in *Escherichia coli* or the like.

EXAMPLES

The present invention will be more concretely described by means of the examples, without intending to limit the scope of the present invention thereto in any way.

Preparation Example 1 Preparation of Fibronectin Fragment (1) Preparation of Fibronectin Fragment H-271, a fragment derived from human fibronectin, was prepared from *Escherichia coli* HB101/pHD101 (FERM BP-2264) in accordance with the method described in U.S. Pat. No. 5,198,423.

In addition, H-296, CH-271 and CH-296, fragments derived from human fibronectin, were each prepared from a culture obtained by culturing *Escherichia coli* HB101/pHD102 (FERM BP-7420), *Escherichia coli* HB101/pCH101 (FERM BP-2799) or *Escherichia coli* HB101/pCH102 (FERM BP-2800), in accordance with the method described in the above-mentioned gazette.

C-274, a fragment derived from human fibronectin, was prepared from a culture obtained by culturing *Escherichia coli* JM109/pTF7221 (FERM BP-1915) in accordance with the method described in U.S. Pat. No. 5,102,988.

C-CS1, a fragment derived from human fibronectin, was prepared from a culture obtained by culturing *Escherichia coli* HB101/pCS25 (FERM BP-5723) in accordance with the method described in Japanese Patent Gazette No. 3104178.

CHV-89 and CHV-179, fragments derived from human fibronectin, were each prepared from a culture obtained by culturing *Escherichia coli* HB101/pCHV89 (FERM P-12182) or *Escherichia coli* RB101/pCHV179 (FERM P-12183), in accordance with the method described in Japanese Patent Gazette No. 2729712.

In addition, CHV-90, a fragment derived from human fibronectin, was prepared in accordance with the method described in Japanese Patent Gazette No. 2729712. Concretely, a plasmid pCHV90 was constructed in accordance with the procedures described in the gazette, and thereafter a transformant carrying the plasmid was cultured, and CHV-90 was prepared from the culture.

CHV-181, a fragment derived from human fibronectin, was prepared by constructing the plasmid (pCHV181) comprising a DNA encoding CHV-181 in accordance with the method described in WO 97/18318, thereafter culturing *Escherichia coli* HB101/pCHV181 into which the plasmid had been introduced, and preparing the fragment from the culture in the same manner as that for the above CHV-179.

(2) Preparation of CHV-92

As to pCHV181, a plasmid for expressing the above-mentioned polypeptide CHV-181, there was constructed a plasmid CHV92 having deletion of a region encoding a 111-13 region in the region encoding CHV-181. The deletion procedures were performed in accordance with procedures for deleting a 111-14 coding region from a plasmid pCHV179, which are described in Japanese Patent Gazette No. 2729712.

*Escherichia coli* HB101 transformed with the above-mentioned plasmid pCHV92 (*Escherichia coli* HB101/pCHV92) was cultured, and the purification procedures were carried out in accordance with the method of purifying the CHV-89 polypeptide described in Japanese Patent Gazette No. 2729712, to obtain a purified CHV-92 preparation from the resulting culture.

(3) Preparation of H-275-Cys

A plasmid for expressing a polypeptide H-275-Cys was constructed in accordance with the following procedures. Concretely, a plasmid pCH102 was prepared from *Escherichia coli* HB101/pCH102 (FERM BP-2800). PCR was carried out using a primer 12S having the nucleotide sequence shown in SEQ ID NO: 21 of Sequence Listing and a primer 14A having the nucleotide sequence shown in SEQ ID NO: 22 of Sequence Listing with the above plasmid as a template, to give a DNA fragment of about 0.8 kb, encoding a heparin binding domain of fibronectin. The resulting DNA fragment was digested with NcoI and BamHI (both manufactured by TAKARA BIO INC.), and thereafter ligated with pTV118N (manufactured by TAKARA BIO INC.) which had been digested with NcoI and BamHI, to construct a plasmid pRH1.

A plasmid vector pINIII-ompA$_1$ [Ghrayeb J., et al., *EMBO J.*, 3(10), 2437-2442 (1984)] was digested with BamHI and HincII (manufactured by TAKARA BIO INC.) to collect a DNA fragment of about 0.9 kb, containing a lipoprotein terminator region. This fragment was mixed and ligated with the above-mentioned plasmid pRH1 which had been digested with BamHI and HincII, to give a plasmid pRH1-T containing a lac promoter, a DNA fragment encoding a heparin binding domain and a lipoprotein terminator in this order.

The reaction for PCR was carried out by using a primer Cys-A having the nucleotide sequence shown in SEQ ID NO: 23 of Sequence Listing and a primer Cys-S having the nucleotide sequence shown in SEQ ID NO: 24 of Sequence Listing with this plasmid pRH1-T as a template. Thereafter, the collected amplified DNA fragment was digested with NotI (manufactured by TAKARA BIO INC.), and the DNA fragment was further self-ligated. A cyclic DNA thus obtained was digested with SpeI and ScaI (manufactured by TAKARA BIO INC.) to give a DNA fragment of 2.3 kb, and the resulting fragment was mixed and ligated with a DNA fragment of 2.5 kb, obtained by digesting the plasmid pRH1-T with SpeI and ScaI (manufactured by TAKARA BIO INC.), to give a plasmid pRH-Cys. The plasmid encodes a polypeptide H-275-Cys in which four amino acids Met-Ala-Ala-Ser were added to an N-terminal side of the above-mentioned H-271, and further Cys was added to a C-terminal of the H-271. The polypeptide H-275-Cys was prepared by the following method. *Escherichia coli* HB101 which had been transformed with the above-mentioned plasmid pRH-Cys (*Escherichia coli* HB101/pRH-Cys) was cultured overnight at 37° C. in 120 mL of an LB medium. The bacterial cells collected from the culture medium were suspended in 40 mL of a buffer for disruption (50 mM Tris-HCl, 1 mM EDTA, 150 mM NaCl, 1 mM DTT, 1 mM PMSF, pH 7.5), and the suspension was subjected to ultrasonic treatment to disrupt the bacterial cells. The supernatant obtained by centrifugation was applied to Hi Trap-heparin column (manufactured by Pharmacia) which had been equilibrated with a purifying buffer (50 mM Tris-HCl, pH 7.5). The non-adsorbed fraction in the column was washed with the same buffer, and thereafter the elution was carried out with a purifying buffer having a 0 to 1 M NaCl concentration gradient. The eluate was analyzed by SDS-polyacrylamide gel electrophoresis, and fractions corresponding to a molecular weight of H-275-Cys were collected to give a purified H-275-Cys preparation.

Example 1

Determination of Expansion Fold in Culture System of LAK Cells (Lymphokine-Activated Killer Cells) Using Low-Serum Medium (1) Isolation and Storage of PBMCs Blood component was collected from a human normal individual donor, obtained with informed consent. The collected blood component was diluted 2-folds with PBS(−), overlaid on Ficoll-paque (manufactured by Pharmacia), and centrifuged at 500×g for 20 minutes. The peripheral blood mononuclear cells (PBMCs) in the intermediate layer were collected with a pipette, and washed. The collected PBMCs were suspended in a storage solution of 90% FBS (manufactured by Bio Whittaker)/10% DMSO (manufactured by SIGMA), and stored in liquid nitrogen. During LAK induction, these stored PBMCs were rapidly melted in water bath at 37° C., and washed with RPMI 1640 medium (manufactured by Bio Whittaker) containing 10 µg/mL DNase (manufactured by Calbiochem). Thereafter, the number of living cells was calculated by trypan blue staining method. The cells were subjected to each experiment.

(2) Immobilization of Anti-Human CD3 Antibody and FN fragment

An anti-human CD3 antibody and an FN fragment were immobilized to a culture equipment used in the following experiment. Concretely, 1 mL (in a case of a 24-well plate) or 2 mL (in a case of 12.5 cm² flask) each of PBS containing an anti-human CD3 antibody (manufactured by Janssen-Kyowa) (final concentration 5 µg/mL) was added to a 24-well cell culture plate or a 12.5 cm² cell culture flask (manufactured by Falcon). Upon the addition, each of the fibronectin fragments (FNfr) listed in Preparation Example 1 was added to a group with addition of an FN fragment so as to have a final concentration of 10 µg/mL (in the case of the 24-well plate) or 25 µg/mL (in the case of the 12.5 cm² flask). As a control, there was also set a group without addition of the FNfr.

After these culture equipments were incubated at room temperature for 5 hours, the culture equipments were stored at 4° C. until use. Immediately before use, PBS containing the antibody and the FNfr was removed by aspiration from these culture equipments, and thereafter each well was washed twice with PBS, and then once with XVIVO20 medium (manufactured by Bio Whittaker), and the culture equipments were subjected to each experiment.

(3) Induction and Culture of LAK Cells

PBMCs which were prepared in item (1) of Example 1 were suspended in XVIVO20 containing 1% human AB serum (hereinafter simply referred to as 1% XVIVO20) so as to have a concentration of 1×10⁶ cells/mL, and thereafter the suspension was put on a plate immobilized with the anti-human CD3 antibody or a plate immobilized with the anti-human CD3 antibody and the FNfr, prepared in item (2) of Example 1, in a volume of 1 mL/well each, and IL-2 (manufactured by Shionogi & Co., Ltd.) was added thereto so as to have a final concentration of 1000 U/mL. These plates were subjected to culture at 37° C. in 5% CO₂ (zeroth day of culture). On the second and third days from the initiation of culture, 1% XVIVO20 containing 1000 U/mL IL-2 was added thereto in a volume of 1 mL/well each. On the fourth day from the initiation of culture, a culture medium properly diluted with 1% XVIVO20 was transferred to a fresh flask to which nothing was immobilized, and IL-2 was added thereto so as to have a final concentration of 500 U/mL. The culture was continued, the culture medium was properly diluted with 1% XVIVO20 every 2 or 3 days in the same manner as the fourth day from the initiation of culture, and IL-2 was added thereto so as to have a final concentration of 300 to 500 U/mL. On the eleventh or fifteenth day from the initiation of culture, the number of living cells was counted by trypan blue staining method, and calculated as an expansion fold by comparing the number of the cells with the number at the initiation of culture. The results are shown in Table 1.

TABLE 1

| Serum Concentration (%) | Cultured Days | Fibronectin Fragment | Expansion Fold |
|---|---|---|---|
| 1 | 11 Days | Control (Without Immobilization of FNfr) | ×252 |
| 1 | 11 Days | CH-296 | ×670 |
| 1 | 11 Days | H-296 | ×615.6 |
| 1 | 15 Days | Control (Without Immobilization of FNfr) | ×403.2 |
| 1 | 15 Days | CH-296 | ×588 |
| 1 | 15 Days | H-296 | ×708 |

As shown in Table 1, in the group using the culture equipment in which each of the fibronectin fragments was immobilized with at an early stage of the induction of the LAK cells using the medium containing a low-concentration serum, the expansion fold of the LAK cells was high as compared to that of the control group. It was clarified from the above that each of the fibronectin fragments was suitably used during the culture of the LAK cells using the medium containing a low-concentration serum.

Example 2

Determination of Expansion Fold in Culture System of LAK Cells Using Low-Serum Medium (Expansion by Repetitive Stimulation)

(1) Induction and Culture of LAK Cells

PBMCs which were prepared in item (1) of Example 1 were suspended in 0.5% or 1% XVIVO20 so as to have a concentration of 1×10⁶ cells/mL, and thereafter the suspension was put on a plate immobilized with the anti-human CD3 antibody or a plate immobilized with the anti-human CD3 antibody and the FNfr, prepared in item (2) of Example 1, in a volume of 1 mL/well each, and IL-2 (manufactured by Shionogi & Co., Ltd.) was added thereto so as to have a final concentration of 1000 U/mL. These plates were subjected to culture at 37° C. in 5% CO₂ (zeroth day of culture). On the second and third days from the initiation of culture, 0.5% or 1% XVIVO20 containing 1000 U/mL IL-2 was added thereto in a volume of 1 mL/well each. On the fourth day from the initiation of culture, a culture medium properly diluted with 0.5% or 1% XVIVO20 was transferred to a fresh flask to which nothing was immobilized, and IL-2 was added thereto so as to have a final concentration of 500 U/mL. On the ninth day from the initiation of culture, a culture medium properly diluted with 0.5% or 1% XVIVO20 was transferred to a flask immobilized with the anti-human CD3 antibody or a flask immobilized with the anti-human CD3 antibody and the FNfr (provided that the concentration of the anti-human CD3 antibody used in the immobilization was 0.5 µg/mL), prepared in the same manner as in item (2) of Example 1, and IL-2 was added thereto so as to have a final concentration of 500 U/mL. On the twelfth day from the initiation of culture, a culture medium properly diluted again with 0.5% or 1% XVIVO20 was transferred to a fresh flask to which nothing was immobilized, and IL-2 was added thereto so as to have a final concentration of 500 U/mL. On the fifteenth day from the initiation of culture, the number of living cells was counted by trypan blue staining method, and calculated as an expansion fold by comparing the number of the cells with the number at the initiation of culture. The results are shown in Table 2.

Example 3

Induction of IL-2 Receptor (IL-2R) Expression in Culture System of LAK Cells Using Low-Serum Medium (1) Induction and Culture of LAK Cells The induction and the culture of LAK cells were carried out in the same manner as in item (1) of Example 2.

(2) Determination of Ratio of IL-2R Expression in LAK Cells

LAK cells which were prepared in item (1) of Example 3 in an amount of $2 \times 10^5$ cells were fixed with PBS (manufactured

TABLE 2

| Serum Concentration (%) | Fibronectin Fragment | Stimulation on 0th Day from Initiation of Culture | Stimulation on 9th Day from Initiation of Culture | Expansion Fold (folds) |
|---|---|---|---|---|
| 0.5 | Control (Without Immobilization of FNfr) | Anti-CD3 | None | ×13 |
| 0.5 | Without Immobilization of FNfr | Anti-CD3 | Anti-CD3 | ×88 |
| 0.5 | CH-296 | Anti-CD3 + CH-296 | Anti-CD3 + CH-296 | ×410 |
| 1 | Control (Without Immobilization of FNfr) | Anti-CD3 | None | ×403 |
| 1 | Without Immobilization of FNfr | Anti-CD3 | Anti-CD3 | ×1624 |
| 1 | CH-296 | Anti-CD3 + CH-296 | None | ×588 |
| 1 | CH-296 | Anti-CD3 + CH-296 | Anti-CD3 + CH-296 | ×3560 |
| 1 | H-296 | Anti-CD3 + H-296 | None | ×708 |
| 1 | H-296 | Anti-CD3 + H-296 | Anti-CD3 + H-296 | ×3000 |

As shown in Table 2, in the group using repeatedly the culture equipment in which each of the fibronectin fragments and the anti-CD3 antibody was immobilized at an early stage and an intermediate stage of the induction of the LAK cells using the medium containing a low-concentration serum, an expansion fold of the LAK cells was high as compared to that of the control group. These expansion folds were far higher than the expansion fold in the group using repeatedly the culture equipment in which only the anti-CD3 antibody was immobilized at an early stage and an intermediate stage of the induction of the LAK cells. In other words, it was clarified that the LAK cells could be induced and cultured with a high expansion fold by stimulation using the fibronectin fragment and the anti-CD3 antibody at an early stage and an intermediate stage of induction of the LAK cells even when the medium containing a low-concentration serum was used.

by Nissui) containing 1% paraformaldehyde (manufactured by Nakalai Tesque, Inc.), and then washed with PBS. The fixed cells were suspended in 100 µL of PBS containing 1% BSA (manufactured by SIGMA), FITC-labeled mouse IgG1 or FITC-labeled mouse anti-human IL-2R (CD25) antibody (both manufactured by DAKO) was added thereto, and thereafter the mixture was incubated on ice for 30 minutes. After the incubation, the cells were washed with PBS, and suspended again in PBS containing 1% paraformaldehyde. The cells were subjected to flow cytometry using FACS Vantage (manufactured by Becton Dickinson), and the content ratio of the IL-2R expression-positive cells was determined. The results are shown in Table 3. In the table, the content ratio of the IL-2R expression-positive cells (%) is shown as the ratio of IL-2R expression (%).

TABLE 3

| Serum Concentration (%) | Fibronectin Fragment | Stimulation on 0th Day from Initiation of Culture | Stimulation on 9th Day from Initiation of Culture | Ratio of IL-2R Expression (%) |
|---|---|---|---|---|
| 0.5 | Control (Without Immobilization of FNfr) | Anti-CD3 | None | 3.48 |
| 0.5 | Without Immobilization of FNfr | Anti-CD3 | Anti-CD3 | 43.22 |
| 0.5 | CH-296 | Anti-CD3 + CH-296 | Anti-CD3 + CH-296 | 81.11 |
| 0.5 | H-296 | Anti-CD3 + H-296 | Anti-CD3 + H-296 | 71.49 |
| 1 | Control (Without Immobilization of FNfr) | Anti-CD3 | None | 8.02 |
| 1 | Without Immobilization of FNfr | Anti-CD3 | Anti-CD3 | 42.8 |
| 1 | CH-296 | Anti-CD3 + CH-296 | Anti-CD3 + CH-296 | 77.94 |
| 1 | H-296 | Anti-CD3 + H-296 | Anti-CD3 + H-296 | 70.29 |

As shown in Table 3, in the group using the culture equipment in which each of the fibronectin fragments was immobilized at an early stage and an intermediate stage of the induction of the LAK cells using the medium containing a low-concentration serum, the ratio of IL-2R expression on the surface of the LAK cells during the culture could be induced at a high level. In other words, it was clarified that the LAK cells could be induced and cultured with increasing the ratio of IL-2R expression when the LAK cells were induced using the medium containing a low-concentration serum in the copresence of the fibronectin fragment.

Example 4

Content Ratio of CD8-Positive Cells in LAK Cell Population Using Low Serum Medium (1) Induction and Culture of LAK Cells The induction and the culture of LAK cells were carried out in the same manner as in item (1) of Example 2.

(2) Determination of Content Ratio of CD8-Positive Cell Population in LAK Cells

LAK cells which were prepared in item (1) of Example 4 in an amount of $2\times10^5$ cells were fixed with PBS containing 1% paraformaldehyde, and then washed with PBS. The fixed cells were suspended in 100 μL of PBS containing 1% BSA, FITC-labeled mouse IgG1 or FITC-labeled mouse anti-human CD8 antibody (both manufactured by DAKO) was added thereto, and thereafter the mixture was incubated on ice for 30 minutes. After the incubation, the cells were washed with PBS, and suspended again in PBS containing 1% paraformaldehyde. The cells were subjected to flow cytometry using FACS Vantage, and the content ratio of the CD8-positive cells was determined. The results are shown in Table 4.

Example 5

Determination of Expansion Fold in Culture System of LAK Cells Using Serum-Free Medium (1) Induction and Culture of LAK Cells PBMCs which were prepared in item (1) of Example 1 were suspended in XVIVO20 without containing serum (hereinafter simply referred to as 0% XVIVO20) so as to have a concentration of $1\times10^6$ cells/mL, and thereafter the suspension was put on a plate immobilized with the anti-human CD3 antibody or a plate immobilized with the anti-human CD3 antibody and the FNfr, prepared in item (2) of Example 1 in a volume of 1 mL/well each, and IL-2 was added thereto so as to have a final concentration of 1000 U/mL. These plates were subjected to culture at 37° C. in 5% $CO_2$ (zeroth day of culture). On the second and third days from the initiation of culture, 0% XVIVO20 containing 1000 U/mL IL-2 was added thereto in a volume of 1 mL/well each. On the fourth day from the initiation of culture, a culture medium properly diluted with 0% XVIVO20 was transferred to a fresh flask to which nothing was immobilized, and IL-2 was added thereto so as to have a final concentration of 500 U/mL. The culture was continued, and the culture medium was properly diluted every 2 or 3 days with 0% XVIVO20 in the same manner as in the fourth day from the initiation of culture, and IL-2 was added thereto so as to have a final concentration of from 300 to 500 U/mL. On the eleventh day or the fifteenth day from the initiation of culture, the number of living cells was counted by trypan blue staining method, and calculated as an expansion fold by comparing the number of the cells with the number at the initiation of culture. The results are shown in Table 5.

TABLE 4

| Serum Concentration (%) | Fibroriectin Fragment | Stimulation on 0th Day from Initiation of Culture | Stimulation on 9th Day from Initiation of Culture | Content Ratio of CD8-Positive Cells (%) |
|---|---|---|---|---|
| 0.5 | Control (Without Immobilization of FNfr) | Anti-CD3 | Anti-CD3 | 26.95 |
| 0.5 | CH-296 | Anti-CD3 + CH-296 | Anti-CD3 + CH-296 | 44.67 |
| 1 | Control (Without Immobilization of FNfr) | Anti-CD3 | None | 53.26 |
| 1 | Without Immobilization of FNfr | Anti-CD3 | Anti-CD3 | 35.56 |
| 1 | CH-296 | Anti-CD3 + CH-296 | None | 61.29 |
| 1 | CH-296 | Anti-CD3 + CH-296 | Anti-CD3 + CH-296 | 62.58 |

As shown in Table 4, in the group using the culture equipment in which each of the fibronectin fragments was immobilized at an early stage or an early stage and an intermediate stage of the induction of the LAK cells using the medium containing a low-concentration serum, the content ratio of CD8-positive cells in the LAK cells during the culture could be induced at a high level. In other words, it was clarified that the LAK cells could be induced and cultured with increasing the content ratio of the CD8-positive cells in the LAK cells when the LAK cells were induced using the medium containing a low-concentration serum in the copresence of the fibronectin fragment.

TABLE 5

| Serum Concentration (%) | Cultured Days | Fibronectin Fragment | Expansion Fold (folds) |
|---|---|---|---|
| 0 | 11 Days | Control (Without Immobilization of FNfr) | 36 |
| 0 | 11 Days | CH-296 | 103.7 |

TABLE 5-continued

| Serum Concentration (%) | Cultured Days | Fibronectin Fragment | Expansion Fold (folds) |
|---|---|---|---|
| 0 | 15 Days | Control (Without Immobilization of FNfr) | 76.3 |
| 0 | 15 Days | CH-296 | 134.6 |
| 0 | 15 Days | Control (Without Immobilization of FNfr) | 28.8 |
| 0 | 15 Days | H-296 | 46.8 |

As shown in Table 5, in the group using the culture equipment in which each of the fibronectin fragments was immobilized at an early stage of the induction of the LAK cells using the medium without containing serum, the expansion fold of the LAK cells was high as compared to that of the control group. It was clarified from the above that each of the fibronectin fragments was suitably used during the culture of the LAK cells using the medium without containing serum.

Example 6

Determination of Expansion Fold in Culture System of LAK Cells in Serum-Free Medium (Expansion by Repetitive Stimulation)

(1) Induction and Culture of LAK Cells

PBMCs which were prepared in item (1) of Example 1 were suspended in 0% XVIVO20 so as to have a concentration of $1\times10^6$ cells/mL, and thereafter the suspension was put on a plate immobilized with the anti-human CD3 antibody or a plate immobilized with the anti-human CD3 antibody and the FNfr, prepared in item (2) of Example 1, in a volume of 1 mL/well each, and IL-2 was added thereto so as to have a final concentration of 1000 U/mL. These plates were subjected to culture at 37° C. in 5% $CO_2$ (zeroth day of culture). On the second and third days from the initiation of culture, 0% XVIVO20 containing 1000 U/mL IL-2 was added thereto in a volume of 1 mL/well each. On the fourth day from the initiation of culture, a culture medium properly diluted with 0% XVIVO20 was transferred to a fresh flask to which nothing was immobilized, and IL-2 was added thereto so as to have a final concentration of 500 U/mL. On the ninth day from the initiation of culture, a culture medium properly diluted with 0% XVIVO20 was transferred to a flask immobilized with the anti-human CD3 antibody or a flask immobilized with the anti-human CD3 antibody and the FNfr (provided that the concentration of the anti-human. CD3 antibody used in the immobilization was 0.5 µg/mL), prepared in the same manner as in item (2) of Example 1, and IL-2 was added thereto so as to have a final concentration of 500 U/mL. On the twelfth day from the initiation of culture, a culture medium properly diluted again with 0% XVIVO20 was transferred to a fresh flask to which nothing was immobilized, and IL-2 was added thereto so as to have a final concentration of 500 U/mL. On the fifteenth day from the initiation of culture, the number of living cells was counted by trypan blue staining method, and calculated as an expansion fold by comparing the number of the cells with the number at the initiation of culture. The results are shown in Table 6.

TABLE 6

| Serum Concentration (%) | Fibronectin Fragment | Stimulation on 0th Day from Initiation of Culture | Stimulation on 9th Day from Initiation of Culture | Expansion Fold (folds) |
|---|---|---|---|---|
| 0 | Control (Without Immobilization of FNfr) | Anti-CD3 | None | x29 |
| 0 | Without Immobilization of FNfr | Anti-CD3 | Anti-CD3 | x36 |
| 0 | CH-296 | Anti-CD3 + CH-296 | None | x56 |
| 0 | CH-296 | Anti-CD3 + CH-296 | Anti-CD3 + CH-296 | x199 |
| 0 | H-296 | Anti-CD3 + H-296 | None | x47 |
| 0 | H-296 | Anti-CD3 + H-296 | Anti-CD3 + H-296 | x209 |

As shown in Table 6, in the group using repeatedly the culture equipment in which each of the fibronectin fragments and the anti-CD3 antibody was immobilized at an early stage and an intermediate stage of the induction of the LAK cells using the medium without containing serum, an expansion fold of the LAK cells was high as compared to that of the control group. These expansion folds were far higher than the expansion fold in the group using repeatedly the culture equipment in which only the anti-CD3 antibody was immobilized at an early stage and an intermediate stage of the induction of the LAK cells. In other words, it was clarified that LAK cells could be induced and cultured with a high expansion fold by stimulation using the fibronectin fragment and the anti-CD3 antibody at an early stage and an intermediate stage of induction of the LAK cells even when the medium without containing serum was used.

Example 7

Induction of IL-2R Expression in Culture System of LAK Cells Using Serum-Free Medium (1) Induction and Culture of LAK Cells The induction and the culture of LAK cells were carried out in the same manner as in item (1) of Example 6.

(2) Determination of Ratio of IL-2R Expression in LAK Cells

The content ratio of the IL-2R expression-positive cells was determined in the same manner as in item (2) of Example 3. The results are shown in Table 7. In the table, the content ratio of the IL-2R expression-positive cells (%) is shown as the ratio of IL-2R expression (%).

TABLE 7

| Serum Concentration (%) | Fibronectin Fragment | Stimulation on 0th Day from Initiation of Culture | Stimulation on 9th Day from Initiation of Culture | Ratio of IL-2R Expression (%) |
| --- | --- | --- | --- | --- |
| 0 | Control (Without Immobilization of FNfr) | Anti-CD3 | None | 1.7 |
| 0 | Without Immobilization of FNfr | Anti-CD3 | Anti-CD3 | 50.5 |
| 0 | CH-296 | Anti-CD3 + CH-296 | None | 3.0 |
| 0 | CH-296 | Anti-CD3 + CH-296 | Anti-CD3 + CH-296 | 82.2 |
| 0 | H-296 | Anti-CD3 + H-296 | None | 3.2 |
| 0 | H-296 | Anti-CD + H-296 | Anti-CD3 + H-296 | 91.9 |

As shown in Table 7, in the group using the culture equipment in which each of the fibronectin fragments was immobilized at an early stage and an intermediate stage of the induction of the LAK cells using the medium without containing serum, the ratio of IL-2R expression on the surface of the LAK cells during the culture could be induced at a high level. In other words, it was clarified that the LAK cells could be induced and cultured with increasing the ratio of IL-2R expression when the LAK cells were induced using the medium without containing serum in the copresence of the fibronectin fragment.

Example 8

Determination of Expansion Fold in Culture System of LAK Cells Using Serum-Free Medium (AIM V)

(1) Induction and Culture of LAK Cells

The induction and the culture of LAK cells were carried out in the same manner as in item (1) of Example 5, provided that a medium used during the induction and the culture was changed to AIM V medium without containing serum (manufactured by Invitrogen, hereinafter simply referred to as 0% AIM V). The results are shown in Table 8.

TABLE 8

| Serum Concentration and Medium | Cultured Days | Fibronectin Fragment | Expansion Fold (folds) |
| --- | --- | --- | --- |
| 0% AIM V | 12 Days | Control (Without Immobilization of FNfr) | ×21 |
| 0% AIM V | 12 Days | CH-296 | ×110 |
| 0% AIM V | 15 Days | Control (Without Immobilization of FNfr) | ×44 |
| 0% AIM V | 15 Days | CH-296 | ×498 |
| 0% AIM V | 12 Days | Control (Without Immobilization of FNfr) | Unproliferated, not detected |
| 0% AIM V | 12 Days | H-296 | ×33 |
| 0% AIM V | 15 Days | Control (Without Immobilization of FNfr) | Unproliferated, not detected |
| 0% AIM V | 15 Days | H-296 | ×245 |

As shown in Table 8, in the group using the culture equipment in which each of the fibronectin fragments was immobilized at an early stage of the induction of the LAK cells using the medium without containing serum, the expansion fold of the LAK cells was high as compared to that of the control group. In addition, this effect was exhibited even when a basal medium for serum-free culture was changed. It was clarified from the above that each of the fibronectin fragments was suitably used during the culture of the LAK cells using the medium without containing serum.

Example 9

Determination of Expansion Fold in Culture System of LAK Cells in Serum-Free Medium (Induction and Culture of LAK Cells from Small Number of Cells/Culture Without Dilution Procedures)

(1) Induction and Culture of LAK Cells PBMCs which were prepared in item (1) of Example 1 were suspended in XVIVO20 (without containing serum) so as to have a concentration of $1 \times 10^5$ cells/mL, and thereafter the suspension was put on a plate immobilized with the anti-human CD3 antibody or a 6-well plate immobilized with the anti-human CD3 antibody and the FNfr, prepared in the same manner as in item (2) of Example 1 in a volume of 1 mL/well each, 4 mL of XVIVO20 (without containing serum) was added thereto ($1 \times 10^4$ cells/cm$^2$), and IL-2 was further added thereto so as to have a final concentration of 500 U/mL. These plates were subjected to culture at 37° C. in 5% $CO_2$ (zeroth day of culture). On the second, third and fourth days from the initiation of culture, IL-2 was added thereto so as to have a final concentration of 500 U/mL. The culture was continued, and IL-2 was added every 2 or 3 days on the seventh and subsequent days from the initiation of culture so as to have a final concentration of 500 U/mL. During the culture, dilution procedures of the culture medium were not carried out at all.

On the fifteenth day from the initiation of culture, the number of living cells was counted by trypan blue staining method, and calculated as an expansion fold by comparing the number of the cells with the number at the initiation of culture. The results are shown in Table 9.

TABLE 9

| Cultured Days | Fibronectin Fragment | Expansion Fold (folds) |
| --- | --- | --- |
| 15 Days | Control (Without Immobilization of FNfr) | Unproliferated, not detected |
| 15 Days | CH-296 | ×64.3 |

As shown in Table 9, in the group using the culture equipment in which each of the fibronectin fragments was immobilized during the induction of LAK cells from a small number of cells, a high expansion fold was obtained on the fifteenth day from the initiation of culture without necessitating the dilution procedures of the cells during the course of the induction. On the other hand, in the control group, the cells hardly proliferated even on the fifteenth day from the initiation of culture. In other words, it was clarified that the LAK cells could be induced and cultured in a high expansion fold when the LAK cells were induced from a small number of cells using the serum-free medium in the copresence of the fibronectin fragment without necessitating the dilution procedures.

Example 10

Induction of IL-2R Expression in Culture System of LAK Cells Using Serum-Free Medium (Induction and Culture of LAK Cells from Small Number of Cells/Culture Without Dilution Procedures)

(1) Induction and Culture of LAK Cells
The induction and the culture of LAK cells were carried out in the same manner as in item (1) of Example 9.
(2) Determination of Ratio of IL2R Expression in LAK Cells
The content ratio of the IL-2R expression-positive cells was determined in the same manner as in item (2) of Example 3. The results are shown in Table 10. In the table, the content ratio of the IL-2R expression-positive cells (%) is shown as the ratio of IL-2R expression (%).

TABLE 10

| Cultured Days | Fibronectin Fragment | Ratio of IL-2R Expression (%) |
| --- | --- | --- |
| 15 Days | Control (Without Immobilization of FNfr) | Unproliferated, not detected |
| 15 Days | CH-296 | 98.0 |

As shown in Table 10, in the group using the culture equipment in which each of the fibronectin fragments was immobilized during the induction of the LAK cells from a small number of cells, the ratio of IL-2R expression on the surface of the LAK cells during the culture could be induced at a high level without necessitating the dilution procedures of the cells during the course of the induction. In other words, it was clarified that the LAK cells could be induced and cultured with increasing the ratio of IL-2R expression when the LAK cells were induced from a small number of cells using the serum-free medium in the copresence of the fibronectin fragment without necessitating the dilution procedures.

Example 11

Content Ratio of CD8-Positive Cells in LAK Cell Population Cultured in Serum-Free Medium (AIM V)

(1) Induction and Culture of LAK Cells
The induction and the culture of LAK cells were carried out in the same manner as in item (1) of Example 8.
(2) Determination of Content Ratio of CD8-Positive Cell Population in LAK Cells
The content ratio of the CD8-positive cells was determined in the same manner as in item (2) of Example 4. The results are shown in Table 11.

TABLE 11

| Serum Concentration and Medium | Fibronectin Fragment | Content Ratio of CD8-Positive Cells (%) |
| --- | --- | --- |
| 0% AIM V | Control (Without Immobilization of FNfr) | 24.7 |
| 0% AIM V | CH-296 | 45.8 |
| 0% AIM V | H-296 | 62.6 |

As shown in Table 11, in the group using the culture equipment in which each of the fibronectin fragments was immobilized at an early stage of the induction of the LAK cells using the medium without containing serum, the content ratio of the CD8-positive cells in the LAK cells during the culture could be induced at a high level. In other words, it was clarified that the LAK cells could be induced and cultured with increasing the content ratio of the CD8-positive cells in the LAK cells when the LAK cells were induced using the medium without containing serum in the copresence of the fibronectin fragment.

Example 12

Determination of Expansion Fold in Culture System of LAK Cells Using Low-Serum Medium (AIM V)

(1) Induction and Culture of LAK Cells
The induction and the culture of LAK cells were carried out in the same manner as in item (3) of Example 1, provided that a medium used during the induction and the culture was changed to AIM V medium containing 1% or 5% human AB serum (hereinafter simply referred to as 1% AIM V or 5% AIM V). The results are shown in Table 12.

TABLE 12

| Serum Concentration and Medium | Cultured Days | Fibronectin Fragment | Expansion Fold (folds) |
| --- | --- | --- | --- |
| 1% AIM V | 11 Days | Control (Without Immobilization of FNfr) | ×7 |
| 1% AIM V | 11 Days | CH-296 | ×156 |
| 1% AIM V | 11 Days | H-296 | ×39 |
| 1% AIM V | 15 Days | Control (Without Immobilization of FNfr) | ×3 |
| 1% AIM V | 15 Days | CH-296 | ×651 |

TABLE 12-continued

| Serum Concentration and Medium | Cultured Days | Fibronectin Fragment | Expansion Fold (folds) |
|---|---|---|---|
| 1% AIM V | 15 Days | H-296 | ×305 |
| 5% AIM V | 11 Days | Control (Without Immobilization of FNfr) | ×454 |
| 5% AIM V | 11 Days | CH-296 | ×1087 |
| 5% AIM V | 11 Days | H-296 | ×727 |
| 5% AIM V | 15 Days | Control (Without Immobilization of FNfr) | ×778 |
| 5% AIM V | 15 Days | CH-296 | ×1548 |
| 5% AIM V | 15 Days | H-296 | ×882 |

As shown in Table 12, in the group using the culture equipment in which each of the fibronectin fragments was immobilized at an early stage of the induction of the LAK cells using the medium (AIM V) containing a low-concentration serum, the expansion fold of the LAK cells was high as compared to that of the control group. It was clarified from the above that each of the fibronectin fragments was suitably used during the culture of the LAK cells using the AIM V medium containing a low-concentration serum.

Example 13

Effects on Expansion Fold in Culture System of LAK Cells Using Various Low-Serum Media (1) induction and Culture of LAK Cells
The induction and the culture of LAK cells were carried out in the same manner as in item (3) of Example 1, provided that a medium used during the induction and the culture was changed to XVIVO20 medium, XVIVO10 medium, or AIM V medium, each containing 1% human AB serum (hereinafter simply referred to as 1% XVIVO20, 1% XVIVO10 or 1% AIM V, respectively). The expansion fold in each medium was determined. The results are shown in Table 13.

TABLE 13

| Serum Concentration and Medium | Cultured Days | Fibronectin Fragment | Expansion Fold (folds) |
|---|---|---|---|
| 1% XVIVO20 | 11 Days | Control (Without Immobilization of FNfr) | ×49 |
| 1% XVIVO20 | 11 Days | CH-296 | ×153 |
| 1% AIM V | 11 Days | Control (Without Immobilization of FNfr) | ×79 |
| 1% AIM V | 11 Days | CH-296 | ×832 |
| 1% XVIVO20 | 15 Days | Control (Without Immobilization of FNfr) | ×272 |
| 1% XVIVO20 | 15 Days | CH-296 | ×513 |
| 1% XVIVO10 | 15 Days | Control (Without Immobilization of FNfr) | ×113 |
| 1% XVIVO10 | 15 Days | CH-296 | ×162 |
| 1% AIM V | 15 Days | Control (Without Immobilization of FNfr) | ×744 |
| 1% AIM V | 15 Days | CH-296 | ×8928 |

As shown in Table 13, in the group using the culture equipment in which each of the fibronectin fragments was immobilized at an early stage of the induction of the LAK cells using the medium containing a low-concentration serum, the expansion fold of the LAK cells was high as compared to that of the control group. In addition, this effect was exhibited even when a basal medium was changed. It was clarified from the above that each of the fibronectin fragments was suitably used during the culture of the LAK cells using any medium containing a low-concentration serum.

Example 14

Determination of Expansion Fold in Culture System of LAK Cells Using Low-Serum Medium (1) Induction and Culture of LAK Cells
The induction and the culture of LAK cells were carried out in the same manner as in item (3) of Example 1, provided that a medium used during the induction and the culture was changed to XVIVO20 medium containing 0.2% human AB serum. The results are shown in Table 14.

TABLE 14

| Serum Concentration and Medium | Cultured Days | Fibronectin Fragment | Expansion Fold (folds) |
|---|---|---|---|
| 0.2% XVIVO20 | 15 Days | Control (Without Immobilization of FNfr) | ×11 |
| 0.2% XVIVO20 | 15 Days | CH-296 | ×67 |

As shown in Table 14, in the group using the culture equipment in which each of the fibronectin fragments was immobilized at an early stage of the induction of the LAK cells using the medium (XVIVO20) containing a low-concentration (0.2%) serum, the expansion fold of the LAK cells was high as compared to that of the control group. It was clarified from the above that each of the fibronectin fragments was suitably used during the culture of the LAK cells using the medium containing a low-concentration serum.

Example 15

Determination of Expansion Fold in Culture System of LAK Cells Using Low-Serum Medium (Expansion by Repetitive Stimulation)

(1) Induction and Culture of LAK Cells
The induction and the culture of LAK cells were carried out in the same manner as in item (1) of Example 2, provided that a medium used during the induction and the culture was changed to XVIVO20 medium containing 0.2% human AB serum or XVIVO10 medium containing 1% human AB serum. The results are shown in Table 15.

TABLE 15

| Serum Concentration and Medium | Fibronectin Fragment | Stimulation on 0th Day from Initiation of Culture | Stimulation on 9th Day from Initiation of Culture | Expansion Fold (folds) |
|---|---|---|---|---|
| 0.2% XVIVO20 | Control (Without Immobilization of FNfr) | Anti-CD3 | None | ×11 |

TABLE 15-continued

| Serum Concentration and Medium | Fibronectin Fragment | Stimulation on 0th Day from Initiation of Culture | Stimulation on 9th Day from Initiation of Culture | Expansion Fold (folds) |
|---|---|---|---|---|
| 0.2% XVIVO20 | Without Immobilization of FNfr | Anti-CD3 | Anti-CD3 | ×9 |
| 0.2% XVIVO20 | CH-296 | Anti-CD3 + CH-296 | Anti-CD3 + CH-296 | ×86 |
| 1% XVIVO10 | Control (Without Immobilization of FNfr) | Anti-CD3 | None | ×113 |
| 1% XVIVO10 | Without Immobilization of FNfr | Anti-CD3 | Anti-CD3 | ×281 |
| 1% XVIVO10 | CH-296 | Anti-CD3 + CH-296 | Anti-CD3 + CH-296 | ×1282 |
| 1% XVIVO10 | Control (Without Immobilization of FNfr) | Anti-CD3 | None | ×24 |
| 1% XVIVO10 | Without Immobilization of FNfr | Anti-CD3 | Anti-CD3 | ×367 |
| 1% XVIVO10 | CH-296 | Anti-CD3 + CH-296 | Anti-CD3 + CH-296 | ×1030 |
| 1% XVIVO10 | H-296 | Anti-CD3 + H-296 | Anti-CD3 + H-296 | ×1001 |

As shown in Table 15, in the group using repeatedly the culture equipment in which each of the fibronectin fragments and the anti-CD3 antibody was immobilized at an early stage and an intermediate stage of the induction of the LAK cells using the medium containing a low-concentration serum (0.2%), the expansion fold of the LAK cells was high as compared to that of the control group. These expansion folds were far higher than the expansion fold in the group using repeatedly the culture equipment in which only the anti-CD3 antibody was immobilized at an early stage and an intermediate stage of the induction of the LAK cells. In addition, this effect was exhibited even when a basal medium was changed. In other words, it was clarified that the LAK cells could be induced and cultured with a high expansion fold by stimulation using the fibronectin fragment and the anti-CD3 antibody at an early stage and an intermediate stage of induction of the LAK cells even when the medium containing a low-concentration serum was used.

Example 16

Induction of IL-2 Receptor (IL-2R) Expression in Culture System of LAK Cells Using Low-Serum Medium (1) Induction and Culture of LAK Cells The induction and the culture of LAK cells were carried out in the same manner as in item (1) of Example 2, provided that a medium used during the induction and the culture was changed to XVIVO20 medium containing 0.2% human AB serum or XVIVO10 medium containing 1% human AB serum.

(2) Determination of Ratio of IL-2R Expression in LAK Cells

The content ratio of the IL-2R expression-positive cells was determined in the same manner as in item (2) of Example 3. The results are shown in Table 16. In the table, the content ratio of the IL-2R expression-positive cells (%) is shown as the ratio of IL-2R expression (%).

TABLE 16

| Serum Concentration and Medium | Fibronectin Fragment | Stimulation on 0th Day from Initiation of Culture | Stimulation on 9th Day from Initiation of Culture | Ratio of IL-2R Expression (%) |
|---|---|---|---|---|
| 0.2% XVIVO20 | Control (Without Immobilization of FNfr) | Anti-CD3 | None | 3.01 |
| 0.2% XVIVO20 | Without Immobilization of FNfr | Anti-CD3 | Anti-CD3 | 59.08 |
| 0.2% XVIVO20 | CH-296 | Anti-CD3 + CH-296 | Anti-CD3 + CH-296 | 77.88 |
| 1% XVIVO10 | Control (Without Immobilization of FNfr) | Anti-CD3 | None | 13.77 |
| 1% XVIVO10 | Without Immobilization of FNfr | Anti-CD3 | Anti-CD3 | 58.28 |
| 1% XVIVO10 | CH-296 | Anti-CD3 + CH-296 | Anti-CD3 + CH-296 | 91.11 |

As shown in Table 16, in the group using the culture equipment in which each of the fibronectin fragments was immobilized at an early stage and an intermediate stage of the induction of the LAK cells using the medium containing a low-concentration serum, the ratio of IL-2R expression on the surface of the LAK cells during the culture could be induced at a high level. In addition, this effect was exhibited even when a basal medium was changed. In other words, it was clarified that the LAK cells could be induced and cultured with increasing the ratio of IL-2R expression when the LAK cells were induced using the medium containing a low-concentration serum in the copresence of the fibronectin fragment.

Example 17

Content Ratio of CD8-Positive Cells in LAK Cell Population Using Low Serum Medium (1) Induction and Culture of LAK Cells The induction and the culture of LAK cells were carried out in the same manner as in item (3) of Example 1, provided that a medium used during the induction and the culture was changed to XVIVO20 medium containing 0.2% or 1% human AB serum or XVIVO10 medium containing 1% human AB serum.

(2) Determination of Content Ratio of CD8-Positive Cell Population in LAK Cells

The content ratio of the CD8-positive cells was determined in the same manner as in item (2) of Example 4. The results are shown in Table 17.

TABLE 17

| Serum Concentration and Medium | Fibronectin Fragment | Content Ratio of CD8-Positive Cells (%) |
| --- | --- | --- |
| 0.2% XVIVO20 | Control (Without Immobilization of FNfr) | 50.9 |
| 0.2% XVIVO20 | CH-296 | 70.9 |
| 1% XVIVO20 | Control (Without Immobilization of FNfr) | 36.2 |
| 1% XVIVO20 | CH-296 | 53.6 |
| 1% XVIVO20 | H-296 | 50.6 |
| 1% XVIVO10 | Control (Without Immobilization of FNfr) | 19.9 |
| 1% XVIVO10 | CH-296 | 45.5 |
| 1% XVIVO10 | H-296 | 53.6 |

As shown in Table 17, in the group using the culture equipment in which each of the fibronectin fragments was immobilized at an early stage of the induction of the LAK cells using the medium containing a low-concentration serum, the content ratio of the CD8-positive cells in the LAK cells during the culture could be induced at a high level. In addition, this effect was exhibited even when a basal medium was changed. In other words, it was clarified that the LAK cells could be induced and cultured with increasing the content ratio of the CD8-positive cells in the LAK cells when the LAK cells were induced using the medium containing a low-concentration serum in the copresence of the fibronectin fragment.

Example 18

Content Ratio of CD8-Positive Cells in LAK Cell Population Using Low Serum Medium (Expansion by Repetitive Stimulation)

1) Induction and Culture of LAK Cells

The induction and the culture of LAK cells were carried out in the same manner as in item (1) of Example 2, provided that a medium used during the induction and the culture was changed to XVIVO20 medium containing 0.2% human AB serum or XVIVO10 medium containing 1% human AB serum.

(2) Determination of Content Ratio of CD8-Positive Cell Population in LAK Cells

The content ratio of the CD8-positive cells was determined in the same manner as in item (2) of Example 4. The results are shown in Table 18.

TABLE 18

| Serum Concentration and Medium | Fibronectin Fragment | Stimulation on 0th Day from Initiation of Culture | Stimulation on 9th Day from Initiation of Culture | Content Ratio of CD8-Positive Cells (%) |
| --- | --- | --- | --- | --- |
| 0.2% XVIVO20 | Control (Without Immobilization of FNfr) | Anti-CD3 | Anti-CD3 | 38.9 |
| 0.2% XVIVO20 | CH-296 | Anti-CD3 + CH-296 | Anti-CD3 + CH-296 | 44.5 |
| 1% XVIVO10 | Control (Without Immobilization of FNfr) | Anti-CD3 | Anti-CD3 | 25.6 |
| 1% XVIVO10 | CH-296 | Anti-CD3 + CH-296 | Anti-CD3 + CH-296 | 38.3 |

As shown in Table 18, in the group using the culture equipment in which each of the fibronectin fragments was immobilized at an early stage or an intermediate stage of the induction of the LAK cells using the medium containing a low-concentration serum, the content ratio of the CD8-positive cells in the LAK cells during the culture could be induced at a high level. In addition, this effect was exhibited even when a basal medium was changed. In other words, it was clarified that the LAK cells could be induced and cultured with increasing the content ratio of the CD8-positive cells in the LAK cells when the LAK cells were induced using the medium containing a low-concentration serum in the copresence of the fibronectin fragment.

Example 19

Determination of Expansion Fold in Culture System of LAK Cells Using Serum-Free Medium (1) Induction and Culture of LAK Cells The induction and the culture of LAK cells were carried out in the same manner as in item (1) of Example 5, provided that a medium used during the induction and the culture was changed to XVIVO10 medium or AIM V medium without containing serum. The results are shown in Table 19.

TABLE 19

| Serum Concentration and Medium | Cultured Days | Fibronectin Fragment | Expansion Fold (folds) |
|---|---|---|---|
| 0% XVIVO10 | 11 Days | Control (Without Immobilization of FNfr) | ×32 |
| 0% XVIVO10 | 11 Days | CH-296 | ×95 |
| 0% XVIVO10 | 15 Days | Control (Without Immobilization of FNfr) | ×205 |
| 0% XVIVO10 | 15 Days | CH-296 | ×407 |
| 0% XVIVO10 | 11 Days | Control (Without Immobilization of FNfr) | ×29 |
| 0% XVIVO10 | 11 Days | H-296 | ×78 |
| 0% XVIVO10 | 15 Days | Control (Without Immobilization of FNfr) | ×27 |
| 0% XVIVO10 | 15 Days | H-296 | ×194 |
| 0% AIM V | 11 Days | Control (Without Immobilization of FNfr) | ×25 |
| 0% AIM V | 11 Days | CH-296 | ×85 |
| 0% AIM V | 11 Days | H-296 | ×69 |
| 0% AIM V | 15 Days | Control (Without Immobilization of FNfr) | ×61 |
| 0% AIM V | 15 Days | CH-296 | ×202 |
| 0% AIM V | 15 Days | H-296 | ×392 |

As shown in Table 19, in the group using the culture equipment in which each of the fibronectin fragments was immobilized at an early stage of the induction of the LAK cells using the medium without containing serum, the expansion fold of the LAK cells was high as compared to that of the control group. In addition, this effect was exhibited even when a basal medium was changed. It was clarified from the above that each of the fibronectin fragments was suitably used during the culture of the LAK cells using the medium without containing serum.

Example 20

Determination of Expansion Fold in Culture System of LAK Cells Using Serum-Free Medium (Expansion by Repetitive Stimulation)

(1) Induction and Culture of LAK Cells

The induction and the culture of LAK cells were carried out in the same manner as in item (1) of Example 6, provided that a medium used during the induction and the culture was changed to XVIVO10 medium without containing serum. The results are shown in Table 20.

TABLE 20

| Serum Concentration and Medium | Fibronectin Fragment | Stimulation on 0th Day from Initiation of Culture | Stimulation on 9th Day from Initiation of Culture | Expansion Fold (folds) |
|---|---|---|---|---|
| 0% XVIVO10 | Control (Without Immobilization of FNfr) | Anti-CD3 | None | ×27 |
| 0% XVIVO10 | Without Immobilization of FNfr | Anti-CD3 | Anti-CD3 | ×288 |
| 0% XVIVO10 | CH-296 | Anti-CD3 + CH-296 | Anti-CD3 + CH-296 | ×845 |
| 0% XVIVO10 | H-296 | Anti-CD3 + H-296 | Anti-CD3 + H-296 | ×893 |

As shown in Table 20, in the group using repeatedly the culture equipment in which each of the fibronectin fragments and the anti-CD3 antibody was immobilized at an early stage and an intermediate stage of the induction of the LAK cells using the medium without containing serum, the expansion fold of the LAK cells was high as compared to that of the control group. These expansion folds were far higher than the expansion fold in the group using repeatedly the culture equipment in which only the anti-CD3 antibody was immobilized at an early stage and an intermediate stage of the induction of the LAK cells. In addition, this effect was exhibited even when a basal medium was changed. In other words, it was clarified that the LAK cells could be induced and cultured with a high expansion fold by stimulation using the fibronectin fragment and the anti-CD3 antibody at an early stage and an intermediate stage of induction of the LAK cells even when the medium without containing serum was used.

Example 21

Induction of IL-2R Expression in Culture System of LAK Cells Using Serum-Free Medium (1) Induction and Culture of LAK Cells The induction and the culture of LAK cells were carried out in the same manner as in item (1) of Example 6, provided that a medium used during the induction and the culture was changed to XVIVO10 medium without containing serum.

(2) Determination of Ratio of IL-2R Expression in LAK Cells

The content ratio of the IL-2R expression-positive cells was determined in the same manner as in item (2) of Example 3. The results are shown in Table 21. In the table, the content ratio of the IL-2R expression-positive cells (%) is shown as the ratio of IL-2R expression (%).

TABLE 21

| Serum Concentration and Medium | Fibronectin Fragment | Stimulation on 0th Day from Initiation of Culture | Stimulation on 9th Day from Initiation of Culture | Ratio of IL-2R Expression (%) |
|---|---|---|---|---|
| 0% XVIVO10 | Control (Without Immobilization of FNfr) | Anti-CD3 | None | 24.99 |
| 0% XVIVO10 | Without Immobilization of FNfr | Anti-CD3 | Anti-CD3 | 80.58 |
| 0% XVIVO10 | CH-296 | Anti-CD3 + CH-296 | None | 40.17 |
| 0% XVIVO10 | CH-296 | Anti-CD3 + CH-296 | Anti-CD3 + CH-296 | 92.59 |
| 0% XVIVO10 | H-296 | Anti-CD3 + H-296 | None | 30.09 |
| 0% XVIVO10 | H-296 | Anti-CD3 + H-296 | Anti-CD3 + H-296 | 87.15 |

As shown in Table 21, in the group using the culture equipment in which each of the fibronectin fragments was immobilized at an early stage and an intermediate stage of the induction of the LAK cells using the medium without containing serum, the ratio of IL-2R expression on the surface of the LAK cells during the culture could be induced at a high level. In other words, it was clarified that the LAK cells could be induced and cultured with increasing the ratio of IL-2R expression when the LAK cells were induced using the medium without containing serum in the copresence of the fibronectin fragment.

Example 22

Content Ratio of CD8-Positive Cells in Cultured LAK Cell Population Using Serum-Free Medium (1) Induction and Culture of LAK Cells The induction and the culture of LAK cells were carried out in the same manner as in item (1) of Example 5, provided that a medium used during the induction and the culture was changed to XVIVO20, XVIVO10 or AIM V medium, each without containing serum.

(2) Determination of Content Ratio of CD8-Positive Cell Population in LAK Cells

The content ratio of the CD8-positive cells was determined in the same manner as in item (2) of Example 4. The results are shown in Table 22.

TABLE 22

| Serum Concentration and Medium | Fibronectin Fragment | Content Ratio of CD8-Positive Cells (%) |
|---|---|---|
| 0% XVIVO20 | Control (Without Immobilization of FNfr) | 20.01 |
| 0% XVIVO20 | CH-296 | 64.48 |
| 0% XVIVO10 | Control (Without Immobilization of FNfr) | 27.91 |
| 0% XVIVO10 | CH-296 | 47.72 |
| 0% AIM V | Control (Without Immobilization of FNfr) | 21.14 |

TABLE 22-continued

| Serum Concentration and Medium | Fibronectin Fragment | Content Ratio of CD8-Positive Cells (%) |
|---|---|---|
| 0% AIM V | CH-296 | 58.8 |
| 0% XVIVO10 | Control (Without Immobilization of FNfr) | 16.53 |
| 0% XVIVO10 | CH-296 | 35.22 |
| 0% XVIVO10 | H-296 | 27.29 |

As shown in Table 22, in the group using the culture equipment in which each of the fibronectin fragments was immobilized at an early stage of the induction of the LAK cells using the medium without containing serum, the content ratio of the CD8-positive cells in the LAK cells during the culture could be induced at a high level. In addition, this effect was exhibited even when a basal medium was changed. In other words, it was clarified that the LAK cells could be induced and cultured with increasing the content ratio of the CD8-positive cells in the LAK cells when the LAK cells were induced using the medium without containing serum in the copresence of the fibronectin fragment.

Example 23

Content Ratio of CD8-Positive Cells in LAK Cell Population Using Serum-Free Medium (Expansion by Repetitive Stimulation)

(1) Induction and Culture of LAK Cells

The induction and the culture of LAK cells were carried out in the same manner as in item (1) of Example 6, provided that a medium used during the induction and the culture was changed to XVIVO20 or XVIVO10 medium, without containing serum.

(2) Determination of Content Ratio of CD8-Positive Cells in LAK Cells

The content ratio of the CD8-positive cells was determined in the same manner as in item (2) of Example 4. The results are shown in Table 23.

TABLE 23

| Serum Concentration and Medium | Fibronectin Fragment | Stimulation on 0th Day from Initiation of Culture | Stimulation on 9th Day from Initiation of Culture | Content Ratio of CD8-Positive Cells (%) |
|---|---|---|---|---|
| 0% XVIVO20 | Control (Without Immobilization of FNfr) | Anti-CD3 | None | 20.01 |
| 0% XVIVO20 | CH-296 | Anti-CD3 + CH-296 | None | 64.48 |
| 0% XVIVO20 | CH-296 | Anti-CD3 + CH-296 | Anti-CD3 + CH-296 | 35.21 |
| 0% XVIVO10 | Control (Without Immobilization of FNfr) | Anti-CD3 | None | 27.91 |
| 0% XVIVO10 | CH-296 | Anti-CD3 + CH-296 | None | 47.72 |
| 0% XVIVO10 | Without Immobilization of FNfr | Anti-CD3 | Anti-CD3 | 37.97 |
| 0% XVIVO10 | CH-296 | Anti-CD3 + CH-296 | Anti-CD3 + CH-296 | 50.22 |
| 0% XVIVO10 | Control (Without Immobilization of FNfr) | Anti-CD3 | None | 16.53 |
| 0% XVIVO10 | CH-296 | Anti-CD3 + CH-296 | None | 35.22 |
| 0% XVIVO10 | H-296 | Anti-CD3 + H-296 | None | 27.29 |
| 0% XVIVO10 | CH-296 | Anti-CD3 + CH-296 | Anti-CD3 + CH-296 | 75.33 |
| 0% XVIVO10 | H-296 | Anti-CD3 + H-296 | Anti-CD3 + H-296 | 61.08 |

As shown in Table 23, in the group using the culture equipment in which each of the fibronectin fragments was immobilized at an early stage or an early to intermediate stage of the induction of the LAK cells using the medium without containing serum, the content ratio of the CD8-positive cells in the LAK cells during the culture could be induced at a high level. In addition, this effect was exhibited even when a basal medium was changed. In other words, it was clarified that the LAK cells could be induced and cultured with increasing the content ratio of CD8-positive cells in the LAK cells when the LAK cells were induced using the medium containing a low-concentration serum in the copresence of the fibronectin fragment.

Example 24

Induction of IL-2R Expression in Culture System of LAK Cells Using Low-Serum Medium (Induction and Culture of LAK Cells from Small Number of Cells/Culture Without Dilution Procedures)

(1) Induction and Culture of LAK Cells

PBMCs which were prepared in item (1) of Example 1 were suspended in XVIVO20 containing 1% human AB serum (hereinafter simply referred to as 1% XVIVO20) so as to have a concentration of $1\times10^5$ cells/mL or $5\times10^4$ cells/mL, and thereafter the suspension was put on a plate immobilized with the anti-human CD3 antibody or a 6-well plate immobilized with the anti-human CD3 antibody and the FNfr, prepared in the same manner as in item (2) of Example 1 in a volume of 1 mL/well each, 4 mL of 1% XVIVO20 was added thereto ($1\times10^4$ cells/cm$^2$ or $5\times10^3$ cells/cm$^2$), and IL-2 (manufactured by Shionogi & Co., Ltd.) was further added thereto so as to have a final concentration of 500 U/mL. These plates were subjected to culture at 37° C. in 5% $CO_2$ (zeroth day of culture). On the second, third and fourth days from the initiation of culture, IL-2 was added thereto so as to have a final concentration of 500 U/mL. The culture was continued, and IL-2 was added every 2 or 3 days on the seventh and subsequent days from the initiation of culture so as to have a final concentration of 500 U/mL. During the culture, dilution procedures of the culture medium were not carried out at all. On the sixteenth day from the initiation of culture, the cells were collected.

(2) Determination of Ratio of IL-2R Expression in LAK Cells

The content ratio of the IL-2R expression-positive cells was determined in the same manner as in item (2) of Example 3. In the table, the content ratio of the IL-2R expression-positive cells (%) is shown as the ratio of IL-2R expression (%). The results are shown in Table 24.

TABLE 24

| Serum Concentration and Medium | Fibronectin Fragment | Ratio of IL-2R Expression (%) |
|---|---|---|
| 1% XVIVO20 | Control (Without Immobilization of FNfr) | 12.15 |
| | CH-296 | 97.47 |
| | H-296 | 95.43 |

As shown in Table 24, in the group using the culture equipment in which each of the fibronectin fragments was immobilized during the induction of the LAK cells from a small number of cells, the ratio of IL2R expression on the surface of the LAK cells during the culture could be induced at a high level without necessitating the dilution procedures of the cells during the course of the induction. In other words, it was clarified that the LAK cells could be induced and cultured with increasing the ratio of IL-2R expression when the LAK cells were induced from a small number of cells using the low-serum medium in the copresence of the fibronectin fragment without necessitating the dilution procedures at all.

Example 25

Determination of Cytotoxic Activity in Culture System of LAK Cells Using Serum-Free or Low-Serum Medium (1) Induction and Culture of LAK Cells The induction and the culture of LAK cells were carried out in the same manner as in item (3) of Example 1, provided that a medium used during the induction and the culture was changed to XVIVO20 medium containing from 0% to 5% human AB serum, or AIM V medium containing from 0% to 5% human AB serum, or XVIVO10 medium containing 5% human AB serum.

(2) Determination of Cytotoxic Activity of Cultured LAK Cells

The cytotoxic activity of LAK prepared in item (1) of Example 25 on the fifteenth day after the culture was evaluated by a determination method for cytotoxic activity using Calcein-AM [Lichtenfels R., et al., *J. Immunol. Methods*, 172(2), 227-239 (1994)]. Cell line K562, Daudi was suspended in RPMI 1640 medium containing 5% FBS (manufactured by Bio Whittaker) so as to have a concentration of $1\times10^6$ cells/mL. Thereafter, Calcein-AM (manufactured by Dotite) was added to the suspension so as to have a final concentration of 25 μM, and the cells were cultured at 37° C. for 1 hour. The cells were washed with a medium not containing Calcein-AM, to give Calcein-labeled target cells.

LAK cells prepared in item (1) of Example 25 were stepwise diluted with RPMI containing 5% human serum (hereinafter simply referred to as 5HRPMI) so as to have a concentration of from $1\times10^6$ to $3\times10^6$ cells/mL as effector cells. Thereafter, each of the dilutions was put in each well of 96-well cell culture plate in an amount of 100 μL/well each. Thereto were added the Calcein-labeled target cells prepared to have a concentration of $1\times10^5$ cells/mL in an amount of 100 μL/well each. The plate containing the above-mentioned cell suspension was centrifuged at 400×g for 1 minute, and thereafter incubated in a wet-type $CO_2$ incubator at 37° C. for 4 hours. After 4 hours, 100 μL of the culture supernatant was collected from each well, and the amount of calcein released (fluorescence intensity) into the culture supernatant was determined by using fluorescence plate reader (485 nm/538 nm). The cytotoxic activity of the LAK cells was calculated by the following formula 1:

Cytotoxic Activity (%)=[(Found Value in Each Well−Minimum Released Amount)/(Maximum Released Amount−Minimum Released Amount)]×100    Formula 1:

In the above formula, the minimum released amount is the amount of calcein released in the well containing only the target cells, showing the amount of calcein naturally released from the target cells. In addition, the maximum released amount refers to the amount of calcein released when the cells are completely disrupted by adding a surfactant Triton X-100 (manufactured by Nakalai Tesque, Inc.) so as to have a final concentration of 0.05% to the target cells. The results are shown in Table 25. In the table, "E/T" shows a ratio on the basis of the number of the effector cells to the number of the target cells (effector cells/target cells).

TABLE 25

| Serum Concentration and Medium | Fibronectin Fragment | E/T | Cytotoxic Activity (%) (Target Cells K562) | Cytotoxic Activity (%) (Target Cells Daudi) |
| --- | --- | --- | --- | --- |
| 0% XVIVO20 | Control (Without Immobilization of FNfr) | 20 | 28.7 | 13.3 |
| 0% XVIVO20 | CH-296 | 20 | 46.7 | 23.8 |
| 0% XVIVO20 | H-296 | 20 | 49.9 | 19.0 |

TABLE 25-continued

| Serum Concentration and Medium | Fibronectin Fragment | E/T | Cytotoxic Activity (%) (Target Cells K562) | Cytotoxic Activity (%) (Target Cells Daudi) |
| --- | --- | --- | --- | --- |
| 0.2% XVIVO20 | Control (Without Immobilization of FNfr) | 10 | 13.3 | 11.6 |
| 0.2% XVIVO20 | CH-296 | 10 | 18.2 | 18.6 |
| 1% XVIVO20 | Control (Without Immobilization of FNfr) | 20 | 36.5 | 24.8 |
| 1% XVIVO20 | H-296 | 20 | 62.8 | 39.0 |
| 5% XVIVO20 | Control (Without Immobilization of FNfr) | 30 | 57.0 | 56.6 |
| 5% XVIVO20 | CH-296 | 30 | 78.1 | 59.1 |
| 0% AIM V | Control (Without Immobilization of FNfr) | 30 | 25.2 | 23.4 |
| 0% AIM V | CH-296 | 30 | 36.8 | 28.1 |
| 5% AIM V | Control (Without Immobilization of FNfr) | 30 | 55.3 | 49.8 |
| 5% AIM V | CH-296 | 30 | 77.2 | 53.6 |
| 5% AIM V | Control (Without Immobilization of FNfr) | 10 | 35.1 | 50.5 |
| 5% AIM V | CH-296 | 10 | 71.6 | 51.8 |
| 5% AIM V | H-296 | 10 | 73.9 | 57.8 |
| 5% XVIVO10 | Control (Without Immobilization of FNfr) | 10 | 72.6 | 51.1 |
| 5% XVIVO10 | CH-296 | 10 | 84.6 | 57.4 |
| 5% XVIVO10 | H-296 | 10 | 89.3 | 69.5 |

As shown in Table 25, in the group using the culture equipment in which each of the fibronectin fragments was immobilized at an early stage of the induction of the LAK cells using the medium without containing serum or the medium containing a low-concentration serum, the cytotoxic activity of the LAK cells was high as compared to that of the control group. In addition, this effect was exhibited even when a basal medium was changed. It was clarified from the above that each of the fibronectin fragments was suitably used during the culture of the LAK cells using the medium without containing serum or the medium containing a low-concentration serum.

Example 26

Determination of Expansion Fold in Culture System of LAK Cells Using Low-Serum Medium (AIM V) (Expansion by Repetitive Stimulation)-1

(1) Induction and Culture of LAK Cells

The induction and the culture of LAK cells were carried out in the same manner as in item (1) of Example 2, provided that a medium used during the induction and the culture was changed to AIM V medium containing 1% human AB serum. The results are shown in Table 26.

TABLE 26

| Serum Concentration and Medium | Fibronectin Fragment | Stimulation on 0th Day from Initiation of Culture | Stimulation on 9th Day from Initiation of Culture | Expansion Fold (folds) |
| --- | --- | --- | --- | --- |
| 1% AIM V | Control (Without Immobilization of FNfr) | Anti-CD3 | Anti-CD3 | ×130 |
| 1% AIM V | CH-296 | Anti-CD3 + CH-296 | Anti-CD3 + CH-296 | ×2419 |

As shown in Table 26, in the group using repeatedly the culture equipment in which each of the fibronectin fragments and the anti-CD3 antibody was immobilized at an early stage and an intermediate stage of the induction of the LAK cells using AIM V medium containing a low-concentration serum (1%), the expansion fold of the LAK cells was high as compared to that of the control group. These expansion folds were far higher than the expansion fold in the group using repeatedly the culture equipment in which only the anti-CD3 antibody was immobilized at an early stage and an intermediate stage of the induction of the LAK cells. In other words, it was clarified that the LAK cells could be induced and cultured with a high expansion fold by stimulation using the fibronectin fragment and the anti-CD3 antibody at an early stage and an intermediate stage of induction of the LAK cells even when the medium containing a low-concentration serum was used.

Example 27

Determination of Expansion Fold in Culture System of LAK Cells Using Low-Serum Medium (AIM V) (Expansion by Repetitive Stimulation)-2

(1) Immobilization of Anti-Human CD3 Antibody and FN Fragment

An anti-human CD3 antibody and an FN fragment were immobilized to a culture equipment (vessel) used in the following experiment. Concretely, 1.9 mL (in a case of a 12-well plate) or 2 mL (in a case of 12.5 cm$^2$ flask) each of PBS containing an anti-human CD3 antibody (final concentration 5 μg/mL) was added to a 12-well cell culture plate or a 12.5 cm$^2$ cell culture flask (manufactured by Falcon). Upon the addition, each of the fibronectin fragments (FNfr) listed in Preparation Example 1 was added to a group with addition of an N fragment so as to have a final concentration of 10 μg/mL (in the case of the 12-well plate) or 25 μg/mL (in the case of the 12.5 cm$^2$ flask). As a control, there was also set a group without addition of the FNfr.

After these culture equipments were incubated at room temperature for 5 hours, the culture equipments were stored at 4° C. until use. Immediately before use, PBS containing the antibody and the FNfr was removed by aspiration from these culture equipments, and thereafter each well was washed twice with PBS, and then once with AIM V medium, and the culture equipments were subjected to each experiment.

(2) Induction and Culture of LAK Cells

PBMCs which were prepared in item (1) of Example 1 were suspended in 1% AIM V so as to have a concentration of $5 \times 10^5$ cells/mL, and thereafter the suspension was put on a plate immobilized with the anti-human CD3 antibody or a plate immobilized with the anti-human CD3 antibody and the FNfr, prepared in item (1) of Example 27 in a volume of 1 mL/well each, and IL-2 was added thereto so as to have a final concentration of 1000 U/mL. These plates were subjected to culture at 37° C. in 5% $CO_2$ (zeroth day of culture). On the second and third days from the initiation of culture, 1% AIM V containing 1000 U/mL IL-2 was added thereto in a volume of 1 mL/well each. On the fourth day from the initiation of culture, the culture medium was transferred to a 25 $cm^2$ cell culture flask (manufactured by Falcon) to which nothing was immobilized, 7 mL of 1% AIM V was further added thereto, and IL-2 was added thereto so as to have a final concentration of 500 U/mL. On the seventh day from the initiation of culture, a part of a culture medium of which cell concentration was adjusted to $2 \times 10^5$ cells/mL with 1 AIM V was transferred to a fresh flask to which nothing was immobilized, and IL-2 was added thereto so as to have a final concentration of 500 U/mL. On the ninth day from the initiation of culture, a part of a culture medium of which cell concentration was adjusted to $2 \times 10^5$ cells/mL with 1% AIM V was transferred to a flask immobilized with the anti-human CD3 antibody or a flask immobilized with the anti-human CD3 antibody and the FNfr (provided that the concentration of the anti-human CD3 antibody used in the immobilization was 0.5 μg/mL), prepared in the same manner as in item (1) of Example 27, and IL-2 was added thereto so as to have a final concentration of 500 U/mL. On the twelfth day from the initiation of culture, a part of a culture medium of which cell concentration was properly adjusted to $2 \times 10^5$ cells/mL with 1% AIM V was transferred again to a fresh flask to which nothing was immobilized, and IL-2 was added thereto so as to have a final concentration of 500 U/mL. On the fifteenth day from the initiation of culture, the number of living cells was counted by trypan blue staining method, and calculated as an expansion fold by comparing the number of the cells with the number at the initiation of culture. The expansion was carried out under the same conditions at n=3, and each of the results of its mean±standard deviation is shown in Table 27.

As shown in Table 27, in the group using repeatedly the culture equipment in which each of the fibronectin fragments and the anti-CD3 antibody was immobilized at an early stage and an intermediate stage of the induction of the LAK cells using the medium containing a low-concentration serum (1%), the expansion fold of the LAK cells was high as compared to that of the control group. These expansion folds were far higher than the expansion fold in the group using repeatedly the culture equipment in which only the anti-CD3 antibody was immobilized at an early stage and an intermediate stage of the induction of the LAK cells. In other words, it was clarified that the LAK cells could be induced and cultured with a high expansion fold by stimulation using the fibronectin fragment and the anti-CD3 antibody at an early stage and an intermediate stage of induction of the LAK cells even when the medium containing a low-concentration serum was used.

Example 28

Content Ratio of CD8-Positive Cells in LAK Cell Population Using Serum-Free Medium (AIM V) (Expansion by Repetitive Stimulation)

(1) Induction and Culture of LAK Cells The induction and the culture of LAK cells were carried out in the same manner as in item (1) of Example 2, provided that a medium used during the induction and the culture was changed to AIM V medium without containing human AB serum.

(2) Determination of Content Ratio of CD8-Positive Cell Population in LAK Cells

The content ratio of the CD8-positive cells was determined in the same manner as in item (2) of Example 4. The results are shown in Table 28.

TABLE 27

| Serum Concentration and Medium | Fibronectin Fragment | Stimulation on 0th Day from Initiation of Culture | Stimulation on 9th Day from Initiation of Culture | Expansion Fold (folds) |
|---|---|---|---|---|
| 1% AIM V | Control (Without Immobilization of FNfr) | Anti-CD3 | None | ×3392 ± 779 |
| 1% AIM V | Without Immobilization of FNfr | Anti-CD3 | Anti-CD3 | ×4389 ± 1234 |
| 1% AIM V | CH-296 | Anti-CD3 + CH-296 | Anti-CD3 + CH-296 | ×8545 ± 1328 | mean ± standard deviation.

TABLE 28

| Serum Concentration and Medium | Fibronectin Fragment | Stimulation on 0th Day from Initiation of Culture | Stimulation on 9th Day from Initiation of Culture | Content Ratio of CD8-Positive Cells (%) |
|---|---|---|---|---|
| 0% AIM V | Control (Without Immobilization of FNfr) | Anti-CD3 | None | 43.8 |
| 0% AIM V | CH-296 | Anti-CD3 + CH-296 | None | 64.4 |
| 0% AIM V | CH-296 | Anti-CD3 + CH-296 | Anti-CD3 + CH-296 | 76.6 |

As shown in Table 28, in the group using the culture equipment in which each of the fibronectin fragments was immobilized at an early stage or an intermediate stage of the induction of the LAK cells using AIM V medium without containing serum, the content ratio of the CD8-positive cells in the cell population after the culture of the LAK cells during the culture could be induced at a high level. In other words, it was clarified that the LAK cells could be induced and cultured with increasing the content ratio of the CD8-positive cells in the LAK cells when the LAK cells were induced using a medium containing a low-concentration serum in the copresence of the fibronectin fragment.

Example 29

Content Ratio of CD8-Positive Cells in LAK Cell Population Using Low-Serum Medium (AIM V)(Expansion by Repetitive Stimulation)

(1) Induction and Culture of LAK Cells

The induction and the culture of LAK cells were carried out in the same manner as in item (1) of Example 2, provided that a medium used during the induction and the culture was changed to AIM V medium containing 1% human AB serum.

(2) Determination of Content Ratio of CD8-Positive Cell Population in LAK Cells

The content ratio of the CD8-positive cells was determined in the same manner as in item (2) of Example 4. The results are shown in Table 29.

As shown in Table 29, in the group using the culture equipment in which each of the fibronectin fragments was immobilized at an early stage or an early to intermediate stage of the induction of the LAK cells using AIM V medium containing a low-concentration serum, the content ratio of the CD8-positive cells in the LAK cell population after the culture could be induced at a high level. In other words, it was clarified that the LAK cells could be induced and cultured with increasing the content ratio of the CD8-positive cells in the LAK cells when the LAK cells were induced using the medium containing a low-concentration serum in the copresence of the fibronectin fragment.

Example 30

Induction of IL-2 Receptor (IL-2R) Expression in Culture System of LAK Cells Using Serum-Free Medium (AIM V)

(1) Induction and Culture of LAK Cells

The induction and the culture of LAK cells were carried out in the same manner as in item (1) of Example 2, provided that a medium used during the induction and the culture was changed to AIM V medium without containing human AB serum.

(2) Determination of Ratio of IL-2R Expression in LAK Cells

The content ratio of the IL-2R expression-positive cells was determined in the same manner as in item (2) of Example 3. The results are shown in Table 30. In the table, the content ratio of the IL-2R expression-positive cells (%) is shown as the ratio of IL-2R expression (%).

TABLE 29

| Serum Concentration and Medium | Fibronectin Fragment | Stimulation on 0th Day from Initiation of Culture | Stimulation on 9th Day from Initiation of Culture | Content Ratio of CD8-Positive Cells (%) |
|---|---|---|---|---|
| 1% AIM V | Control (Without Immobilization of FNfr) | Anti-CD3 | None | 39.2 |
| 1% AIM V | Control (Without Immobilization of FNfr) | Anti-CD3 | Anti-CD3 | 60.0 |
| 1% AIM V | CH-296 | Anti-CD3 + CH-296 | None | 49.2 |
| 1% AIM V | CH-296 | Anti-CD3 + CH-296 | Anti-CD3 + CH-296 | 71.0 |

TABLE 30

| Serum Concentration and Medium (%) | Fibronectin Fragment | Stimulation on 0th Day from Initiation of Culture | Stimulation on 9th Day from Initiation of Culture | Ratio of IL-2R Expression (%) |
|---|---|---|---|---|
| 0% AIM V | Control (Without Immobilization of FNfr) | Anti-CD3 | None | 22.0 |
| 0% AIM V | Control (Without Immobilization of FNfr) | Anti-CD3 | Anti-CD3 | 39.9 |
| 0% AIM V | CH-296 | Anti-CD3 + CH-296 | Anti-CD3 + CH-296 | 51.9 |

As shown in Table 30, in the group using the culture equipment in which each of the fibronectin fragments was immobilized at an early stage and an intermediate stage of the induction of the LAK cells using AIM V medium without containing serum, the ratio of IL-2R expression on the surface of the LAK cells after the culture could be induced at a high level. In other words, it was clarified that the LAK cells could be induced and cultured with increasing the ratio of IL-2R expression when the LAK cells were induced using the medium without containing serum in the copresence of the fibronectin fragment.

Example 31

Induction of IL-2 Receptor (IL-2R) Expression in Culture System of LAK Cells Using Low-Serum Medium (AIM V) (Expansion by Repetitive) Stimulation (1) Induction and Culture of LAK Cells The induction and the culture of LAK cells were carried out in the same manner as in item (1) of Example 2, provided that a medium used during the induction and the culture was changed to AIM V medium containing 1% human AB serum.

(2) Determination of Ratio of IL-2R Expression in LAK Cells

The content ratio of the IL-2R expression-positive cells was determined in the same manner as in item (2) of Example 3. The results are shown in Table 31. In the table, the content ratio of the IL-2R expression-positive cells (%) is shown as the ratio of IL-2R expression (%).

TABLE 31

| Serum Concentration and Medium (%) | Fibronectin Fragment | Stimulation on 0th Day from Initiation of Culture | Stimulation on 9th Day from Initiation of Culture | Ratio of IL-2R Expression (%) |
|---|---|---|---|---|
| 1% AIM V | Control (Without Immobilization of FNfr) | Anti-CD3 | None | 23.6 |
| 1% AIM V | CH-296 | Anti-CD3 + CH-296 | None | 27.2 |
| 1% AIM V | CH-296 | Anti-CD3 + CH-296 | Anti-CD3 + CH-296 | 69.1 |

As shown in Table 31, in the group using the culture equipment in which each of the fibronectin fragments was immobilized at an early stage and an intermediate stage of the induction of the LAK cells using the medium containing a low-concentration serum, the ratio of IL-2R expression on the surface of the LAK cells during the culture could be induced at a high level. In other words, it was clarified that the LAK cells could be induced and cultured with increasing the ratio of IL-2R expression when the LAK cells were induced using the medium containing a low-concentration serum in the copresence of the fibronectin fragment.

Example 32

Content Ratio of CD8-Positive Cells in LAK Cell Population Using Low-Serum Medium (AIM V)

(1) Induction and Culture of LAK Cells

The induction and the culture of LAK cells were carried out in the same manner as in item (3) of Example 1, provided that a medium used during the induction and the culture was changed to AIM V medium containing 1% human AB serum.

(2) Determination of Content Ratio of CD8-Positive Cell Population in LAK Cells

The content ratio of the CD8-positive cells was determined in the same manner as in item (2) of Example 4. The results are shown in Table 32.

TABLE 32

| Serum Concentration and Medium | Fibronectin Fragment | Content Ratio of CD8-Positive Cells (%) |
|---|---|---|
| 1% AIM V | Control (Without Immobilization of FNfr) | 41.02 |
| 1% AIM V | CH-296 | 56.78 |

As shown in Table 32, in the group using the culture equipment in which each of the fibronectin fragments was immobilized at an early stage of the induction of the LAK cells using AIM V medium containing a low-concentration serum, the content ratio of the CD8-positive cells in the LAK cells during the culture could be induced at a high level. In other words, it was clarified that the LAK cells could be induced and cultured with increasing the content ratio of the CD8-positive cells in the LAK cells when the LAK cells were induced using the medium containing a low-concentration serum in the copresence of the fibronectin fragment.

Example 33

Determination of Cytotoxic Activity in Culture System of LAK Cells Using Serum-Free Medium or Low-Serum Medium (1) Induction and Culture of LAK Cells The induction and the culture of LAK cells were carried out in the same manner as in item (3) of Example 1 or in item (1) of Example 2, provided that a medium used during the induction and the culture was changed to XVIVO10, XVIVO20 or AIM V medium, containing 0% or 1% human AB serum.

(2) Determination of Cytotoxic Activity of Cultured LAK Cells

The cytotoxic activity of LAK on the fifteenth day after the culture was determined in the same manner as in item (2) of Example 25. The results are shown in Table 33.

TABLE 33

| Serum Concentration and Medium (%) | Fibronectin Fragment | Stimulation on 0th Day from Initiation of Culture | Stimulation on 9th Day from Initiation of Culture | E/T | Cytotoxic Activity (%) Target Cells K562 | Cytotoxic Activity (%) Target Cells Daudi |
|---|---|---|---|---|---|---|
| 0% XVIVO10 | Control (Without Immobilization of FNfr) | Anti-CD3 | None | 10 | 11.88 | 10.84 |
| 0% XVIVO10 | CH-296 | Anti-CD3 + CH-296 | None | 10 | 19.55 | 26.23 |
| 1% AIM V | Control (Without Immobilization of FNfr) | Anti-CD3 | None | 10 | 16.82 | 33.02 |
| 1% AIM V | CH-296 | Anti-CD3 + CH-296 | None | 10 | 46.54 | 42.3 |
| 0% XV1VO20 | Control (Without Immobilization of FNfr) | Anti-CD3 | Anti-CD3 | 10 | 24.5 | 13.3 |
| 0% XVIVO20 | CH-296 | Anti-CD3 + CH-296 | Anti-CD3 + CH-296 | 10 | 30.8 | 23.3 |
| 1% XVIVO20 | Control (Without Immobilization of FNfr) | Anti-CD3 | Anti-CD3 | 10 | 18.5 | 13.9 |
| 1% XVIVO20 | CH-296 | Anti-CD3 + CH-296 | Anti-CD3 + CH-296 | 10 | 30.8 | 28.5 |
| 1% XVIVO10 | Control (Without Immobilization of FNfr) | Anti-CD3 | Anti-CD3 | 10 | 13.8 | 8.4 |
| 1% XVIVO10 | CH-296 | Anti-CD3 + CH-296 | Anti-CD3 + CH-296 | 10 | 33.0 | 31.8 |

As shown in Table 33, in the group using the culture equipment in which each of the fibronectin fragments was immobilized at an early stage or at an early stage and an intermediate stage of the induction of the LAK cells using the medium without containing serum or the medium containing a low-concentration serum, the cytotoxic activity of the LAK cells was high as compared to that of the control group. In addition, this effect was exhibited even when a basal medium was changed. It was clarified from the above that each of the fibronectin fragments was suitably used during the culture of the LAK cells using the medium without containing serum or the medium containing a low-concentration serum.

Example 34

Determination of Expansion Fold in Culture System of LAK Cells Using Low-Serum Medium (XVIVO10) (Culture Using $CO_2$ Gas-Permeable Bag for Cell Culture)

(1) Immobilization of Anti-Human CD3 antibody and FN Fragment

An anti-human CD3 antibody and an FN fragment were immobilized to a culture equipment ($CO_2$ gas-permeable bag for cell culture) used in the following experiment. Concretely, 20 mL each of PBS containing an anti-human CD3 antibody (final concentration: 5 µg/mL) was added to a 85 cm² $CO_2$ gas-permeable bag for cell culture (manufactured by Baxter). Upon the addition, each of the fibronectin fragments (FNfr) described in Preparation Example 1 was added to a group with addition of an FN fragment so as to have a final concentration of 42.5 µg/mL. As a control, there was also set a group without addition of the FNfr.

After these culture equipments were incubated at room temperature for 5 hours, the culture equipments were stored at 4° C. until use. Immediately before use, PBS containing the antibody and the FNfr was removed from these culture equipments, and thereafter each bag was washed twice with PBS, and once with a XVIVO10 medium containing 1% human AB serum (hereinafter simply referred to as 1% XVIVO10) to be subjected to each experiment.

(2) Induction and Culture of LAK Cells

PBMCs which were prepared in item (1) of Example 1 were suspended in 1% XvIVO10 so as to have a concentration of $1 \times 10^6$ cells/mL, and thereafter the cell suspension was placed in an amount of 10 mL/bag each into a $CO_2$ gas-permeable bag for cell culture, immobilized with the anti-human CD3 antibody or a $CO_2$ gas-permeable bag for cell culture, immobilized with the anti-human CD3 antibody and the FNfr, prepared in item (1) of Example 34, and IL-2 was added thereto so as to have a final concentration of 1000 U/mL. These $CO_2$ gas-permeable bags for cell culture were incubated at 37° C. in 5% $CO_2$ (zeroth day of culture). On the second day after the initiation of culture, 1% XVIVO10 containing 1000 U/mL IL-2 was added thereto in an amount of 20 mL/bag each. On the fourth day after the initiation of culture, IL-2 was added thereto so as to have a final concentration of 500 U/mL. On the sixth day after the initiation of culture, 1% XVIVO10 was added thereto in an amount of 30 mL/bag each, and IL-2 was added thereto so as to have a final concentration of 500 U/mL. On the eighth day after the initiation of culture, a part of a culture medium was properly diluted, and thereafter the dilution was transferred to a 85 cm² $CO_2$ gas-permeable bag for cell culture to which nothing was immobilized, and IL-2 was added thereto so as to have a final concentration of 500 U/mL. On the eleventh and thirteenth days after the initiation of culture, IL-2 was added thereto so as to have a final concentration of 500 U/mL. On the fifteenth day after the initiation of culture, the number of living cells was counted by trypan blue staining method, and calculated as an expansion fold by comparing the number of the cells with the number at the initiation of culture. The results are shown in Table 34.

TABLE 34

| Serum Concentration and Medium | Cultured Days | Fibronectin Fragment | Expansion Fold (folds) |
|---|---|---|---|
| 1% XVIVO10 | 15 Days | Control (Without Immobilization of FNfr) | ×34 |
| 1% XVIVO10 | 15 Days | CH-296 | ×101 |

As shown in Table 34, in the group using the $CO_2$ gas-permeable bag for cell culture in which each of the fibronectin fragments was immobilized at an early stage of the induction of the LAK cells using the medium (XVIVO10) containing a low-concentration serum (1%) and the $CO_2$ gas-permeable bag for cell culture, the expansion fold of the LAK cells was high as compared to that of the control group. It was clarified from the above that each of the fibronectin fragments was suitably used during the culture of the LAK cells using the medium containing a low-concentration serum and the $CO_2$ gas-permeable bag for cell culture.

Example 35

Determination of Expansion Fold in Culture System of LAK Cells Using Low-Serum Medium (XVIVO10) (Culture in Combination of Flask for Cell Culture and $CO_7$ Gas-Permeable Bag for Cell Culture)

(1) Immobilization of Anti-Human CD3 Antibody and FN Fragment

An anti-human CD3 antibody and an FN fragment were immobilized to a culture equipment (25 cm² flask for cell culture) used in the following equipment. Concretely, 6 mL each of PBS containing an anti-human CD3 antibody (final concentration: 5 μg/mL) was added to a 25 cm² flask for cell culture (manufactured by Corning). Upon the addition, each of the fibronectin fragments (FNfr) described in Preparation Example 1 was added to a group with addition of an FN fragment so as to have a final concentration of 42.5 μg/mL. As a control, there was also set a group without addition of the FNfr.

After these culture equipments were incubated at room temperature for 5 hours, the culture equipments were stored at 4° C. until use. Immediately before use, PBS containing the antibody and the FNfr was removed from these culture equipments, and each flask was washed twice with PBS, and once with XVIVO10 medium containing 1% human AB serum (hereinafter simply referred to as 1% XVIVO10) to be subjected to each experiment.

(2) Induction and Culture of LAK Cells

PBMCs which were prepared in item (1) of Example 1 were suspended in 1% XVIVO10 so as to have a concentration of $1\times10^6$ cells/mL, and thereafter the cell suspension was placed in an amount of 3 mL/flask each into the flask immobilized with the anti-human CD3 antibody or the flask immobilized with an anti-human CD3 antibody and the FNfr, prepared in item (1) of Example 35, and IL-2 was added thereto so as to have a final concentration of 1000 U/mL. These flasks were incubated at 37° C. in 5% $CO_2$ (zeroth day of culture). On the first day or the second day after the initiation of culture, 1% XVIVO10 containing 1000 U/mL IL-2 was added thereto in an amount of 7 mL/flask each. Hereinafter, the incubation was carried out depending upon the stimulation period with the anti-CD3 antibody±CH-296 by two methods. (i) On the fourth day after the initiation of culture, the culture medium was transferred to a 85 cm² $CO_2$ gas-permeable bag for cell culture to which nothing was immobilized. Thereafter, 1% XVIVO10 was added thereto in an amount of 20 mL/bag each, and IL-2 was added thereto so as to have a final concentration of 500 U/mL. Further, on the sixth day after the initiation of culture, 1% XVIVO10 was added thereto in an amount of 30 mL/bag each, and IL-2 was added thereto so as to have a final concentration of 500 U/mL (stimulation period with anti-CD3 antibody±CH-296: 4 days). (ii) On the fourth day or the fifth day after the initiation of culture, IL-2 was added to the culture medium so as to have a final concentration of 500 U/mL. On the sixth day after the initiation of culture, the culture medium was transferred to a 85 cm² $CO_2$ gas-permeable bag for cell culture to which nothing was immobilized, 1% XVIVO10 was added thereto in an amount of 50 mL/bag each, and IL-2 was added thereto so as to have a final concentration of 500 U/mL (stimulation period with anti-CD3 antibody t CH-296: 6 days). In both of the conditions, on the eighth day after the initiation of culture, a part of the culture medium was properly diluted, and the dilution was transferred to a 85 cm² $CO_2$ gas-permeable bag for cell culture to which nothing was immobilized, and IL-2 was added thereto so as to have a final concentration of 500 U/mL. On the eleventh and thirteenth days after the initiation of culture, IL-2 was added thereto so as to have a final concentration of 500 U/mL. On the fifteenth day after the initiation of culture, the number of living cells was counted by trypan blue staining method, and calculated as an expansion fold by comparing the number of the cells with the number at the initiation of culture. The results are shown in Table 35.

TABLE 35

| Serum Concentration and Medium | Stimulation Period Anti-CD3 ± CH-296 | Cultured Days | Fibronectin Fragment | Expansion Fold (folds) |
|---|---|---|---|---|
| 1% XVIVO10 | 4 Days | 15 Days | Control (Without Immobilization of FNfr) | ×235 |
| 1% XVIVO10 | 4 Days | 15 Days | CH-296 | ×498 |
| 1% XVIVO10 | 6 Days | 15 Days | Control (Without Immobilization of FNfr) | ×425 |
| 1% XVIVO10 | 6 Days | 15 Days | CH-296 | ×690 |

As shown in Table 35, in the group using the flask for cell culture in which each of the fibronectin fragments was immobilized at an early stage of the induction of the LAK cells in the combination of the flask for cell culture and the $CO_2$ gas-permeable bag for cell culture using the medium (XVIVO10) containing a low-concentration serum (1%), the expansion fold of the LAK cells was high as compared to that of the control group. It was clarified from the above that each of the fibronectin fragments was suitably used during the culture of the LAK cells in the combination of the flask for cell culture and the $CO_2$ gas-permeable bag for cell culture using the medium containing a low-concentration serum.

Example 36

Determination of Expansion Fold in Culture System of LAK Cells Using Low-Serum Medium (AIM V) (Culture in Combination of Flask for Cell Culture and $CO_2$ Gas-Permeable Bag for Cell Culture)

(1) Immobilization of Anti-Human CD3 Antibody and FN Fragment

An anti-human CD3 antibody and an FN fragment were immobilized to a culture equipment (25 $cm^2$ flask for cell culture) used in the following experiment in the same manner as in item (1) of Example 35. Immediately before use, PBS containing the antibody and the FNfr was removed from these culture equipments, and each flask was washed twice with PBS, and once with AIM V medium containing 1% human AB serum (hereinafter simply referred to as 1% AIM V) to be subjected to each experiment.

(2) Induction and Culture of LAK Cells

PBMCs which were prepared in item (1) of Example 1 were suspended in 1% AIM V so as to have a concentration of $1\times10^6$ cells/mL, and thereafter the cell suspension was placed in an amount of 3 mL/flask each into the flask immobilized with the anti-human CD3 antibody or the flask immobilized with the anti-human CD3 antibody and the FNfr, prepared in item (1) of Example 36, and IL-2 was added thereto so as to have a final concentration of 1000 U/mL. These flasks were incubated in 5% $CO_2$ at 37° C. (zeroth day of culture). On the first day after the initiation of culture, 1% AIM V containing 1000 U/mL IL-2 was added thereto in an amount of 7 mL/flask each. On the fourth day after the initiation of culture, the culture medium was transferred to a 85 $cm^2$ $CO_2$ gas-permeable bag for cell culture to which nothing was immobilized, 1% AIM V was added thereto in an amount of 20 mL/bag each, and IL-2 was added thereto so as to have a final concentration of 500 U/mL. On the sixth day after the initiation of culture, 1% AIM V was added thereto in an amount of 30 mL/bag each, and IL-2 was added thereto so as to have a final concentration of 500 U/mL. On the eighth day after the initiation of culture, a part of the culture medium was properly diluted, and thereafter transferred to a 85 $cm^2$ $CO_2$ gas-permeable bag for cell culture to which nothing was immobilized, and IL-2 was added thereto so as to have a final concentration of 500 U/mL. On the eleventh and thirteenth days after the initiation of culture, IL-2 was added thereto so as to have a final concentration of 500 U/mL. On the fifteenth day after the initiation of culture, the number of living cells was counted by trypan blue staining method, and calculated as an expansion fold by comparing the number of the cells with the number at the initiation of culture. The results are shown in Table 36.

TABLE 36

| Serum Concentration and Medium | Cultured Days | Fibronectin Fragment | Expansion Fold (folds) |
| --- | --- | --- | --- |
| 1% AIM V | 15 Days | Control (Without Immobilization of FNfr) | ×327 |
| 1% AIM V | 15 Days | CH-296 | ×566 |

As shown in Table 36, in the group using the flask for cell culture in which each of the fibronectin fragments was immobilized at an early stage of the induction of the LAK cells in the combination of the flask for cell culture and the $CO_2$ gas-permeable bag for cell culture using the medium (AIM V) containing a low-concentration serum (1%), the expansion fold of the LAK cells was high as compared to that of the control group. It was clarified from the above that each of the fibronectin fragments was suitably used during the culture of the LAK cells using the combination of the flask for cell culture and the $CO_2$ gas-permeable bag for cell culture using the medium containing a low-concentration serum.

Example 37

Content Ratio of CD8-Positive Cells in LAK Cell Population Using Low-Serum Medium (XVIVO10) (Culture Using $CO_2$ Gas-Permeable Bag for Cell Culture)

(1) Induction and Culture of LAK Cells

The induction and the culture of LAK cells were carried out in the same manner as in item (2) of Example 34.

(2) Determination of Content Ratio of CD8-Positive Cell Population in LAK Cells

The content ratio of the CD8-positive cells was determined in the same manner as in item (2) of Example 4. The results are shown in Table 37.

TABLE 37

| Serum Concentration and Medium | Cultured Days | Fibronectin Fragment | Content Ratio of CD8-Positive Cells (%) |
| --- | --- | --- | --- |
| 1% XVIVO10 | 15 Days | Control (Without Immobilization of FNfr) | 45.7 |
| 1% XVIVO10 | 15 Days | CH-296 | 61.6 |

As shown in Table 37, in the group using the $CO_2$ gas-permeable bag for cell culture in which each of the fibronectin fragments was immobilized at an early stage of the induction of the LAK cells using the medium (XVIVO10) containing a low-concentration serum (1%) and the $CO_2$ gas-permeable bag for cell culture, the content ratio of the CD8-positive cells in the LAK cells after the culture could be induced at a high level. It was clarified from the above that each of the fibronectin fragments was suitably used during the culture of the LAK cells using the medium containing a low-concentration serum and the $CO_2$ gas-permeable bag for cell culture.

Gas-Permeable Bag for Cell Culture.

Example 38

Content Ratio of CD8-Positive Cells in LAK Cell Population Using Low-Serum Medium (XVIVO10) (Culture in Combination of Flask for Cell Culture and $CO_2$ Gas-Permeable Bag for Cell Culture)

(1) Induction and Culture of LAK Cells

The induction and the culture of LAK cells were carried out in the same manner as in item (2) of Example 35.

(2) Determination of Content Ratio of CD8-Positive Cell Population in LAK Cells

The content ratio of the CD8-positive cells was determined in the same manner as in item (2) of Example 4. The results are shown in Table 38.

TABLE 38

| Serum Concentration and Medium | Stimulation Period Anti-CD3 ± CH-296 | Cultured Days | Fibronectin Fragment | Content Ratio of CD8-Positive Cells (%) |
|---|---|---|---|---|
| 1% XVIVO10 | 4 Days | 15 Days | Control (Without Immobilization of FNfr) | 58.1 |
| 1% XVIVO10 | 4 Days | 15 Days | CH-296 | 70.3 |
| 1% XVIVO10 | 6 Days | 15 Days | Control (Without Immobilization of FNfr) | 58.3 |
| 1% XVIVO10 | 6 Days | 15 Days | CH-296 | 72.7 |

As shown in Table 38, in the group using the flask for cell culture in which each of the fibronectin fragments was immobilized at an early stage of the induction of the LAK cells in the combination of the flask for cell culture and the $CO_2$ gas-permeable bag for cell culture using the medium (XVIVO10) containing a low-concentration serum (1%), the content ratio of the CD8-positive cells in LAK cells after the culture could be induced at a high level as compared to that of the control group. It was clarified from the above that each of the fibronectin fragments was suitably used during the culture of the LAK cells in the combination of the flask for cell culture and the $CO_2$ gas-permeable bag for cell culture using the medium containing a low-concentration serum.

Example 39

Determination of Expansion Fold in Culture System of LAK Cells Using Low-Serum Medium (AIM V) (Concentrations at Initiation of culture and at Subculture)

The influence on an expansion fold of the cell concentrations at the initiation of culture and during the subculture in the culture system of the LAK cells was confirmed.

The cell concentrations at the initiation of culture were set at $0.5 \times 10^6$ cells/mL and $1 \times 10^6$ cells/mL. The subculture cell concentrations on the fourth day of culture were set at $0.025 \times 10^6$ cells/mL and $0.05 \times 10^6$ cells/mL. The subculture cell concentrations on the seventh, ninth and eleventh days of the culture were set at $0.2 \times 10^6$ cells/mL and $0.5 \times 10^6$ cells/mL. The above patterns are shown in the following Table 39-1.

TABLE 39-1

| | Concentration at Initiation of Culture | Concentration on Fourth Day from Initiation of Culture | Concentrations at Seventh, Ninth, and Eleventh Day from Initiation of Culture |
|---|---|---|---|
| Cell Concentration Pattern 1 | 0.500 | 0.025 | 0.2 |
| Cell Concentration Pattern 2 | 0.500 | 0.05 | 0.2 |
| Cell Concentration Pattern 3 | 0.500 | 0.05 | 0.5 |
| Cell Concentration Pattern 4 | 1.000 | 0.025 | 0.2 |
| Cell Concentration Pattern 5 | 1.000 | 0.05 | 0.2 |
| Cell Concentration Pattern 6 | 1.000 | 0.05 | 0.5 |

*Cell Concentration ($\times 10^6$ cells/mL)

(1) immobilization of Anti-Human CD3 Antibody and FN Fragment

An anti-human CD3 antibody and an FN fragment were immobilized to a culture equipment used in the following experiment. Concretely, 1 mL each of PBS containing the anti-human CD3 antibody (final concentration: 5 µg/mL) was added to a 24-well cell culture plate. Upon the addition, the fibronectin fragment (CH-296) described in Preparation Example 1 was added to a group with addition of an FN fragment so as to have a final concentration of 25 µg/mL. As a control, there was also set a group without addition of CH-296.

After these culture equipments were incubated at room temperature for 5 hours, and the culture equipments were stored at 4° C. until use. Immediately before use, PBS containing the anti-human CD3 antibody and CH-296 was removed by aspiration from these culture equipments, and each well Was washed twice with PBS, and once with an RPMI medium to be subjected to each experiment.

(2) Induction and Culture of LAK Cells

PBMCs which were prepared in item (1) of Example 1 were suspended in AIM V containing 1% human AB serum so that groups in which the cells were cultured in cell concentration patterns 1, 2 and 3 have a concentration of $0.5 \times 10^6$ cells/mL, and that groups in which the cells were cultured in cell concentration patterns 4, 5 and 6 have a concentration of $1 \times 10^6$ cells/mL. Thereafter, the cell suspension was put in an amount of 1 mL/well each on a plate immobilized with the anti-human CD3 antibody or a plate immobilized with the anti-human CD3 antibody and CH-296, prepared in item (1), and IL-2 was added thereto so as to have a final concentration of 1000 U/mL. These plates were incubated at 37° C. in 5% $CO_2$ (zeroth day of culture). On the second and third days after the initiation of culture, 1% AIM V containing 1000 U/mL IL-2 was added thereto in an amount of 1 mL/well each.

On the fourth day after the initiation of culture, the groups in which the cells were cultured in cell concentration patterns 1 and 4 were diluted with AIM V containing 1% human AB serum (maximum amount of liquid: 6 mL) so as to have a concentration of $0.025 \times 10^6$ cells/mL, and the groups in which the cells were cultured in cell concentration patterns 2, 3, 5 and 6 were diluted with AIM V containing 1% human AB serum (maximum amount of liquid: 6 mL) so as to have a concentration of $0.05 \times 10^6$ cells/mL, and the dilutions were transferred to a 12.5 cm² cell culture flask to which nothing was immobilized, respectively. In each group, IL-2 was added thereto so as to have a final concentration of 500 U/mL.

On the seventh, ninth and eleventh days after the initiation of culture, the groups in which the cells were cultured in cell concentration patterns 1, 2, 4 and 5 were each diluted with AIM V containing 1% human AB serum (maximum amount of liquid: 6 mL) so as to have a concentration of $0.2 \times 10^6$ cells/mL, and the groups in which the cells were cultured in cell concentration patterns 3 and 6 were each diluted with AIM V containing 1% human AB serum (maximum amount of liquid: 6 mL) so as to have a concentration of $0.5 \times 10^6$ cells/mL, and the dilutions were transferred to a 12.5 cm² cell culture flask to which nothing was immobilized, respectively. In each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out three times. Each of the average results is shown in Table 39-2.

TABLE 39-2

|  | Stimulation on Zeroth Day from Initiation of Culture | Expansion Fold (folds) |
| --- | --- | --- |
| Cell Concentration Pattern 1 | Anti-CD3 | 1427 |
|  | Anti-CD3 + CH-296 | 2649 |
| Cell Concentration Pattern 2 | Anti-CD3 | 3401 |
|  | Anti-CD3 + CH-296 | 3691 |
| Cell Concentration Pattern 3 | Anti-CD3 | 749 |
|  | Anti-CD3 + CH-296 | 2508 |
| Cell Concentration Pattern 4 | Anti-CD3 | 256 |
|  | Anti-CD3 + CH-296 | 436 |
| Cell Concentration Pattern 5 | Anti-CD3 | 1091 |
|  | Anti-CD3 + CH-296 | 1179 |
| Cell Concentration Pattern 6 | Anti-CD3 + CH-296 | 476 |

As shown in Table 39-2, in the culture of the LAK cells at various cell concentrations at the initiation of culture and the subculture, in any cell concentration groups, a high expansion fold was obtained in the group stimulated with CH-296 and the anti-CD3 antibody, as compared to that of the control group (stimulation only with the anti-CD3 antibody). In other words, it was shown that the LAK cells could be clearly induced and cultured at a high expansion fold by stimulation with CH-296 for cell concentrations at the initiation of culture and during the subculture, which were variable under various circumstances.

Example 40

Content Ratio of CD8-Positive Cells in LAK Cell Population Cultured Using Low-Serum Medium (AIM V) (Concentrations at Initiation of Culture and at Subculture)

(1) Induction and Culture of LAK Cells
The induction and the culture of LAK cells were carried out in the same manner as in Example 39.
(2) Determination of Content Ratio of CD8-Positive Cell Population in LAK Cells
The content ratio of the CD8-positive cells was determined in the same manner as in item (2) of Example 4. The results are shown in Table 40.

TABLE 40

|  | Stimulation on Zeroth Day from Initiation of Culture | Content Ratio of CD8-Positive Cells (%) |
| --- | --- | --- |
| Cell Concentration Pattern 1 | Anti-CD3 | 55 |
|  | Anti-CD3 + CH-296 | 63 |
| Cell Concentration Pattern 2 | Anti-CD3 | 62 |
|  | Anti-CD3 + CH-296 | 73 |
| Cell Concentration Pattern 3 | Anti-CD3 | 71 |
|  | Anti-CD3 + CH-296 | 75 |
| Cell Concentration Pattern 4 | Anti-CD3 | 56 |
|  | Anti-CD3 + CH-296 | 70 |
| Cell Concentration Pattern 5 | Anti-CD3 | 61 |
|  | Anti-CD3 + CH-296 | 70 |
| Cell Concentration Pattern 6 | Anti-CD3 + CH-296 | 76 |

As shown in Table 40, in the culture of the LAK cells at various cell concentrations at the initiation of culture and at the subculture, in any cell concentration groups, the content ratio of the CD8-positive cells in the LAK cells during culture could be induced at a high level in the group stimulated with CH-296 and the anti-CD3 antibody, as compared to that of the control group (stimulation with only anti-CD3 antibody). In other words, it was clarified that the LAK cells could be induced and cultured with clearly increasing the content ratio of the CD8-positive cells in the LAK cells by stimulation with CH-296 for cell concentrations at the initiation of culture and at the subculture, which were variable under various circumstances.

Example 41

Determination of Expansion Fold in Culture System of LAK Cells Using Low-Serum Medium (AIM V) (High-Concentration, High-Density Culture)

In the culture system of LAK cells, if the final amount of culture medium and the final culture area can be controlled as much as possible, the medium, the material and labor can be reduced. The influence on the expansion fold was confirmed when the cells were cultured in a high concentration at a high density.

There were set a group without controlling cell concentration and cell density upon the subculture (normal culture group); a group in which cell concentrations upon the subculture on the seventh and tenth days of culture were respectively 1.8 times and about 6 times that of the normal culture group (high-concentration culture group, provided that the cell density is similarly 1.8 times and about 6 times, proportional to the concentration); a group in which cell concentrations upon the subculture on the seventh and tenth days of culture were respectively 1.3 times and about 2.5 times that of the normal culture group and cell densities were respectively about 3.9 times and 7.5 times (high-concentration, high-density culture group). The cell concentration and the cell density upon subculture in each of the above groups are shown in the following Table 41-1.

TABLE 41-1

|  |  | Zeroth Day of Culture | Fourth Day of Culture | Seventh Day of Culture | Tenth Day of Culture |
| --- | --- | --- | --- | --- | --- |
| Normal Culture Group | Cell Concentration ($\times 10^6$ cells/mL) | 0.333 | 0.050 | 0.100 | 0.15 |
|  | Cell Density ($\times 10^6$ cells/cm$^2$) | 0.263 | 0.024 | 0.048 | 0.072 |
| High-Concentration Culture Group | Cell Concentration ($\times 10^6$ cells/mL) | 0.333 | 0.050 | 0.180 | 0.893 |
|  | Cell Density ($\times 10^6$ cells/cm$^2$) | 0.263 | 0.024 | 0.086 | 0.429 |

TABLE 41-1-continued

|  |  | Zeroth Day of Culture | Fourth Day of Culture | Seventh Day of Culture | Tenth Day of Culture |
|---|---|---|---|---|---|
| High-Concentration, High-Density Culture Group | Cell Concentration ($\times 10^6$ cells/mL) | 0.333 | 0.050 | 0.13 | 0.38 |
|  | Cell Density ($\times 10^6$ cells/cm$^2$) | 0.263 | 0.024 | 0.186 | 0.543 |

(1) Immobilization of Anti-Human CD3 Antibody and FN Fragment

An anti-human CD3 antibody and an FN fragment were immobilized to culture equipments used in the following experiment. Concretely, 1.9 mL each of PBS containing the anti-human CD3 antibody (final concentration: 5 µg/mL) was added to a 12-well cell culture plate. Upon the addition, a fibronectin fragment (CH-296) described in Preparation Example 1 was added to a group with addition of an FN fragment so as to have a final concentration of 25 µg/mL. As a control, there was also set a group without addition of CH-296.

After these culture equipments were incubated at room temperature for 5 hours, the culture equipments were stored at 4° C. until use. Immediately before use, PBS containing the anti-human CD3 antibody and CH-296 was removed by aspiration from these culture equipments, and thereafter each well was washed twice with PBS, and once with RPMI medium. Each experiment was carried out using the culture equipment.

(2) Induction and Culture of LAK Cells

In each culture group, PBMCs which were prepared in item (1) of Example 1 were suspended in AIM V containing 1% human AB serum so as to have a concentration of $0.33 \times 10^6$ cells/mL, and thereafter the cell suspension was put on a plate immobilized with the anti-human CD3 antibody or a plate immobilized with the anti-human CD3 antibody and CH-296, prepared in item (1) of Example 41, in a volume of 3 mL/well each, and IL-2 was added thereto so as to have a final concentration of 1000 U/mL. These plates were incubated at 37° C. in 5% $CO_2$ (zeroth day of culture).

On the fourth day from the initiation of culture, each culture group was diluted with AIM V containing 1% human AB serum (maximum amount of liquid: 6 mL) so as to have a concentration of $0.05 \times 10^6$ cells/mL, and the dilution was transferred to a 12.5 cm$^2$ cell culture flask to which nothing was immobilized. In each group, IL-2 was added thereto so as to have a final concentration of 500 U/mL.

On the seventh day from the initiation of culture, the normal culture group and the high-concentration culture group were diluted with AIM V containing 1% human AB serum (maximum amount of liquid: 6 mL), so as to have a concentration of the normal culture group of $0.1 \times 10^6$ cells/mL, and a concentration of the high-concentration culture group of $0.18 \times 10^6$ cells/mL. The dilution was transferred to a 12.5 cm$^2$ cell culture flask to which nothing was immobilized. In addition, the high-concentration, high-density culture group was diluted with AIM V containing 1% human AB serum (maximum amount of liquid: 9 mL), so as to have a concentration of $0.13 \times 10^6$ cells/mL, and the dilution was transferred to a 25 cm$^2$ cell culture flask kept upright to which nothing was immobilized. In each group, IL-2 was added thereto so as to have a final concentration of 500 U/mL.

On the tenth day from the initiation of culture, the normal culture group and the high-concentration culture group were diluted with AIM V containing 1% human AB serum (maximum amount of liquid: 6 mL), so as to have a concentration of the normal culture group of $0.15 \times 10^6$ cells/mL, and a concentration of and the high-concentration culture group of $0.893 \times 10^6$ cells/mL. The dilution was transferred to a 12.5 cm$^2$ cell culture flask to which nothing was immobilized. In addition, the high-concentration, high-density culture group was diluted with AIM V containing 1% human AB serum (maximum amount of liquid: 9 mL), so as to have a concentration of $0.38 \times 10^6$ cells/mL, and the dilution was transferred to a 25 cm$^2$ cell culture flask kept upright to which nothing was immobilized. In each group, IL-2 was added thereto so as to have a final concentration of 500 U/mL.

On the eleventh day from the initiation of culture, in each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in 41-2.

TABLE 41-2

|  | Stimulation on Zeroth Day from Initiation of Culture | Expansion Fold (fold) |
|---|---|---|
| Normal Culture Group | Anti-CD3 | 601 |
|  | Anti-CD3 + CH-296 | 2325 |
| High-Concentration Culture Group | Anti-CD3 | 112 |
|  | Anti-CD3 + CH-296 | 1131 |
| High-Concentration, High-Density Culture Group | Anti-CD3 | 215 |
|  | Anti-CD3 + CH-296 | 1307 |

As shown in Table 41-2, in the normal culture group, the high-concentration culture group or the high-concentration, high-density culture group, a high expansion fold was obtained in the group stimulated with CH-296 and the anti-CD3 antibody in any one of the groups, as compared to that of the control group (stimulation only with anti-CD3 antibody). In other words, an effect on expansion was clearly found by stimulation with CH-296 in the high-concentration, high-density culture which could reduce the medium, the material and labor.

Example 42

Content Ratio of CD 8-Positive Cells in LAK Cell Population Cultured Using Low-Serum Medium (AIM V) (High-Concentration, High-Density Culture)

(1) Induction and Culture of LAK Cells

The induction and the culture of LAK cells were carried out in the same manner as in Example 41.

(2) Determination of Content Ratio of CD8-Positive Cell Population in LAK Cells

The content ratio of the CD8-positive cells was determined in the same manner as in item (2) of Example 4. The results are shown in Table 42.

TABLE 42

|  | Stimulation on Zeroth Day from Initiation of Culture | Content Ratio of CD8-Positive Cells (%) |
|---|---|---|
| Normal Culture Group | Anti-CD3 | 53 |
|  | Anti-CD3 + CH-296 | 63 |
| High-Concentration Culture Group | Anti-CD3 | 55 |
|  | Anti-CD3 + CH-296 | 72 |
| High-Concentration, High-Density Culture Group | Anti-CD3 | 63 |
|  | Anti-CD3 + CH-296 | 65 |

As shown in Table 42, in the normal culture group, the high-concentration culture group or the high-concentration, high-density culture group, the content ratio of the CD 8-positive cells in LAK cells in all the groups during culture could be induced at a high level in the group stimulated with CH-296 and the anti-CD3 antibody in any one of the groups, as compared to that of the control group (stimulation only with anti-CD3 antibody). In other words, it was clarified that LAK cells could be clearly induced and cultured while increasing the content ratio of the CD8-positive cells in LAK cells by stimulation with CH-296 in the high-concentration, high-density culture which could reduce the medium, the material and labor.

Example 43

Determination of Expansion Fold in Culture System of LAK Cells Using Low-Serum Medium (AIM V) (Serum Concentrations 0%, 0.15% 5% 0.1%)

When blood is taken in a volume of 30 mL at one time in the culture of LAK cells, approximately 15 mL of plasma is obtained. When culture in a medium containing this plasma in a final volume of up to 10 L is taken into consideration, a plasma concentration would be 0.15%. In addition, when the culture is initiated from a plasma concentration of 5%, on the fourth or subsequent days, a plasma concentration in a medium during the subculture and the dilution of the cells would be about 0.1%. In view of the above, the influence of the serum concentration on the culture system of LAK cells Was confirmed.

At the initiation of culture, there was set a group containing 0%, 0.15% or 5% human AB serum, respectively. PBMCs which were prepared in item (1) of Example 1 were suspended in AIM V containing human AB serum at each concentration, so as to have a concentration of $0.33 \times 10^6$ cells/mL, and thereafter the suspension was put on a plate immobilized with the anti-human CD3 antibody or a plate immobilized with the anti-human CD3 antibody and CH-296, prepared in item (1) of Example 41, in a volume of 3 mL/well each, and IL-2 was added thereto so as to have a final concentration of 1000 U/mL. These plates were incubated at 37° C. in 5% $CO_2$ (zeroth day of culture).

On the fourth day from the initiation of culture, a group subjected to culture with AIM V containing 0% or 0.15% human AB serum was each diluted with AIM V containing 0% or 0.15% human AB serum, so as to have a maximum concentration of $0.05 \times 10^6$ cells/mL, and the dilution was transferred to a 12.5 $cm^2$ cell culture flask to which nothing was immobilized (amount of liquid: 2.5 mL). A group subjected to culture with AIM V containing 5% human AB serum was diluted with AIM V containing 0.1% human AB serum (amount of liquid: 6 µL) so as to have a concentration of $0.05 \times 10^6$ cells/mL, and the dilution was transferred to a 12.5 $cm^2$ cell culture flask to which nothing was immobilized. In each group, IL-2 was added thereto so as to have a final concentration of 500 U/mL.

On the seventh day from the initiation of culture, a group subjected to culture with AIM V containing 0% or 0.15% human AB serum was each diluted with AIM V containing the same serum concentration, so as to have a concentration of $0.11 \times 10^6$ cells/mL, and the dilution was transferred to a fresh 25 $cm^2$ cell culture flask kept upright to which nothing was immobilized (maximum amount of liquid: 12.6 mL). A group subjected to culture with AIM V containing 5% human AB serum was diluted with AIM V containing 0.1% human AB serum so as to have a concentration of $0.11 \times 10^6$ cells/mL, and the dilution was transferred to a fresh 25 $cm^2$ cell culture flask kept upright to which nothing was immobilized (maximum amount of liquid: 12.6 mL). In each group, IL-2 was added thereto so as to have a final concentration of 500 U/mL.

On the tenth day from the initiation of culture, a group subjected to culture with AIM V containing 0% or 0.15% human AB serum was each diluted with AIM V containing the same serum concentration, so as to have a concentration of $0.22 \times 10^6$ cells/mL, and the dilution was transferred to a fresh 25 $cm^2$ cell culture flask kept upright to which nothing was immobilized (maximum amount of liquid: 12.6 mL). A group subjected to culture with AIM V containing 5% human AB serum was diluted with AIM V containing 0.1% human AB serum so as to have a concentration of $0.6 \times 10^6$ cells/mL, and the dilution was transferred to a fresh 25 $cm^2$ cell culture flask kept upright to which nothing was immobilized (maximum amount of liquid: 12.6 mL). In each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in Table 43.

TABLE 43

| Serum Concentration and Medium | Stimulation on Zeroth Day from Initiation of Culture | Expansion Fold (fold) |
|---|---|---|
| 0% AIM V | Anti-CD3 | 25 |
|  | Anti-CD3 + CH-296 | 322 |
| 0.15% AIM V | Anti-CD3 | 42 |
|  | Anti-CD3 + CH-296 | 197 |
| 5% → 0.1% AIM V | Anti-CD3 | 175 |
|  | Anti-CD3 + CH-296 | 353 |

As shown in Table 43, in the culture of LAK cells using AIM V medium containing each serum concentration, a high expansion fold was obtained in the group stimulated with CH-296 and the anti-CD3 antibody in any one of serum concentration groups, as compared to that of the control group (stimulation only with anti-CD3 antibody). In other words, in the culture of LAK cells at a serum concentration assuming that 30 mL of blood was collected, the LAK cells could be clearly induced and cultured at a high expansion fold by stimulation with CH-296 and the anti-CD3 antibody. In addition, the cells during the culture at this time were in a high concentration and at a high density. The expansion fold was clearly high even under the conditions as described above by stimulation with CH-296, so that the effectiveness of CH-296 was found.

Example 44

Determination of Expansion Fold in Culture System of LAK Cells Using Low-Serum Medium (AIM V) (Serum Concentrations 3%→1%→0%→0%, 3%→1%→0.1%→0%. 3%→0.5%→0.2%→0.2% (About One-Half Amount of Final Culture Medium), 3%→0.5%→0.2%→0.05%)

From the same viewpoint as that of Example 43, the influence of serum concentrations on the c ulture system of LAK cells was confirmed taking plasma concentrations obtained by collection of 30 mL blood into consideration.

The human AB serum concentration was 3% at the initiation of culture. There were respectively set a group in which the cells were diluted with AIM V medium containing 1% or 0.5% human AB serum on the fourth day of culture; a group in which the cells were diluted with AIM V medium containing 0%, 0.1% or 0.2% human AB serum on the seventh day of culture; and a group in which the cells were diluted with AIM V medium containing 0%, 0.05% or 0.2% human AB serum on the tenth day of culture. The above patterns are shown in the following Table 44-1.

TABLE 44-1

|  | Fourth Day from Initiation of Culture | Seventh Day from Initiation of Culture | Tenth Day from Initiation of Culture |
| --- | --- | --- | --- |
| Serum Concentration Pattern 1 | 1% | 0% | 0% |
| Serum Concentration Pattern 2 | 1% | 0.1% | 0% |
| Serum Concentration Pattern 3 | 0.5% | 0.2% | 0.2% |
| Serum Concentration Pattern 4 | 0.5% | 0.2% | 0.05% |

*showing human AB serum concentration contained in the medium for diluting the cell culture medium PBMCs which were prepared in item (1) of Example 1 were suspended in AIM V containing 3% human AB serum so as to have a concentration of $0.33 \times 10^6$ cells/mL, and thereafter the suspension was put on a plate immobilized with the anti-human CD3 antibody or a plate immobilized with the anti-human CD3 antibody and CH-296, prepared in item (1) of Example 41, in a volume of 3 mL/well each, and IL-2 was added thereto so as to have a final concentration of 1000 U/mL. These plates were incubated at 37° C. in 5% $CO_2$ (zeroth day of culture).

On the fourth day from the initiation of culture, groups subjected to culture under the serum concentration patterns 1 and 2 were diluted with AIM V containing 1% human AB serum (amount of liquid: 6 mL) so as to have a concentration of $0.05 \times 10^6$ cells mL, and the dilution was transferred to a 12.5 cm² cell culture flask to which nothing was immobilized. Groups subjected to culture under the serum concentration patterns 3 and 4 were diluted with AIM V containing 0.5% human AB serum (amount of liquid: 6 mL) so as to have a concentration of $0.058 \times 10^6$ cells/mL, and the dilution was transferred to a 12.5 cm² cell culture flask to which nothing was immobilized. In each group, IL-2 was added thereto so as to have a final concentration of 500 U/mL.

On the seventh day from the initiation of culture, the group subjected to culture under the serum concentration pattern 1 was diluted with AIM V without containing human AB serum (amount of liquid: 12.6 mL) so as to have a concentration of $0.28 \times 10^6$ cells/mL, and the group subjected to culture under the serum concentration pattern 2 was diluted with AIM V containing 0.1% human AB serum (amount of liquid: 12.6 mL) so as to have a concentration of $0.28 \times 10^6$ cells/mL, and the dilution was transferred to a fresh 25 cm² cell culture flask kept upright to which nothing was immobilized, respectively. Groups subjected to culture under the serum concentration patterns 3 and 4 were diluted with AIM V containing 0.2% human AB serum (amount of liquid: 12.6 mL) so as to have a concentration of $0.48 \times 10^6$ cells/mL, and the dilution was transferred to a fresh 25 cm² cell culture flask kept upright to which nothing was immobilized. In each group, IL-2 was added thereto so as to have a final concentration of 500 U/mL.

On the tenth day from the initiation of culture, groups subjected to culture under the serum concentration patterns 1 and 2 were diluted with AIM V without containing human AB serum (amount of liquid: 12.6 mL) so as to have a concentration of $0.51 \times 10^6$ cells/mL, and the dilution was transferred to a fresh 25 cm² cell culture flask kept upright to which nothing was immobilized. The group subjected to culture under the serum concentration pattern 3 was diluted with AIM V containing 0.2% human AB serum (amount of liquid: 12.6 mL) so as to have a concentration of $0.839 \times 10^6$ cells/mL, and the group subjected to culture under the serum concentration pattern 4 was diluted with AIM V containing 0.05% human AB serum (amount of liquid: 12.6 mL) so as to have a concentration of $0.43 \times 10^6$ cells/mL, and the dilution was transferred to a fresh 25 cm² cell culture flask kept upright to which nothing was immobilized, respectively. In each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in Table 44-2.

TABLE 44-2

|  | Stimulation on Zeroth Day from Initiation of Culture | Expansion Fold (fold) |
| --- | --- | --- |
| Serum Concentration Pattern 1 | Anti-CD3 | 182 |
|  | Anti-CD3 + CH-296 | 425 |
| Serum Concentration Pattern 2 | Anti-CD3 | 195 |
|  | Anti-CD3 + CH-296 | 430 |
| Serum Concentration Pattern 3 (About One-Half Amount of Final Culture Medium) | Anti-CD3 | 101 |
|  | Anti-CD3 + CH-296 | 242 |
| Serum Concentration Pattern 4 | Anti-CD3 | 190 |
|  | Anti-CD3 + CH-296 | 416 |

As shown in Table 44-2, in the culture of LAK cells using AIM V medium containing each serum concentration, a high expansion fold was obtained in the group stimulated with CH-296 and the anti-CD3 antibody, in any one of serum concentration groups, as compared to that of the control group (stimulation only with anti-CD3 antibody). In other words, in the culture of LAK cells at a serum concentration assuming that 30 mL blood was collected, the LAK cells could be clearly induced and cultured at a high expansion fold by stimulation with CH-296 and the anti-CD3 antibody than the stimulation with the anti-CD3 antibody alone. In addition, the cells during the culture at this time were in a high concentration and at a high density and. The expansion fold was clearly high by stimulation with CH-296 even under the conditions as described above, so that the effectiveness of CH-296 was found.

Example 45

Determination of Expansion Fold in Culture System of LAK Cells Using Low-Serum Medium (AIM V) (Culture in Combination of Flask for Cell Culture and $CO_2$ Gas-Permeable Bag for Cell Culture)

(1) Induction and Culture of LAK Cells

The induction and the culture of LAK cells were carried out in the same manner as in item (2) of Example 36. The results are shown in Table 45.

TABLE 45

| Serum Concentration and Medium | Stimulation Period Anti-CD3 ± CH-296 | Cultured Days | Fibronectin Fragment | Expansion Fold (folds) |
|---|---|---|---|---|
| 1% AIM V | 4 Days | 15 Days | Control (Without Immobilization of FNfr) | ×327 |
| 1% AIM V | 4 Days | 15 Days | CH-296 | ×566 |
| 1% AIM V | 6 Days | 15 Days | Control (Without Immobilization of FNfr) | ×371 |
| 1% AIM V | 6 Days | 15 Days | CH-296 | ×425 |

As shown in Table 45, in the group using the flask for cell culture to which each of the fibronectin fragments was immobilized at an early stage of the induction of LAK cells in the combination of the flask for cell culture and the $CO_2$ gas-permeable bag for cell culture using the medium (AIM V) containing a low-concentration serum (1%), the expansion fold of LAK cells was high as compared to that of the control group. It was clarified from the above that each of the fibronectin fragments was suitably used during the culture of LAK cells in the combination of the flask for cell culture and the $CO_2$ gas-permeable bag for cell culture using the medium containing a low-concentration serum.

Example 46

Determination of Expansion Fold in Culture System of LAK Cells Using Freshly Isolated PBMCs and Autologous Plasma-Containing Medium (With AIM V Medium Containing 0.5% Autologous Plasma, Culture in Combination of Flask for Cell Culture and $CO_2$ Gas-Permeable Bag for Cell Culture)

(1) Isolation and Storage of PBMCs

Thirty milliliters of blood was collected with a blood collecting injection syringe from a human normal individual donor, obtained with informed consent, and thereafter the collected blood was centrifuged at 500×g for 20 minutes to collect autologous plasma and a buffy coat layer. The collected buffy coated layer was diluted with PBS, overlaid on Ficoll-paque (manufactured by Pharmacia), and centrifuged at 500×g for 20 minutes. Peripheral blood mononuclear cells (PBMCs) in an intermediate layer was collected with a pipette, and washed. Regarding the collected freshly isolated PBMCs, the number of living cells was calculated by trypan blue staining method. Each experiment was carried out using the culture equipment.

The collected autologous plasma was inactivated at 56° C. for 30 minutes, and thereafter centrifuged at 800×g for 30 minutes, and the supernatant was used as an inactivated autologous plasma (hereinafter simply referred to as autologous plasma).

(2) Immobilization of Anti-Human CD3 Antibody and FN Fragment

An anti-human CD3 antibody and an FN fragment were immobilized to a culture equipment (25 cm² flask for cell culture) used in the following experiment, in the same manner as in item (1) of Example 35. Immediately before use, PBS containing the antibody and the FNfr was removed from the culture equipment, and each flask was washed twice with PBS, and once with AIM V medium. Each experiment was carried out using the culture equipment.

(3) Induction and Culture of LAK Cells

Freshly isolated PBMCs which were prepared in item (1) of Example 46 were suspended in AIM V containing 0.5% autologous plasma (hereinafter simply referred to as 0.5% autologous plasma AIM V) so as to have a concentration of 1×10⁶ cells/mL, and thereafter the cell suspension was placed in a flask immobilized with the anti-human CD3 antibody or a flask immobilized with the anti-human CD3 antibody and the FNfr, prepared in item (2) of Example 46, in a volume of 3 mL/flask each, and IL-2 was added thereto so as to have a final concentration of 1000 U/mL. These flasks were incubated at 37° C. in 5% $CO_2$ (zeroth day of culture). On the first day from the initiation of culture, 0.5% autologous plasma AIM V containing 1000 U/mL IL-2 was added thereto in an amount of 7 mL/flask. On the fourth day from the initiation of culture a culture medium was transferred to a 85 cm² $CO_2$ gas-permeable bag for cell culture (Optisite bag or X-Fold bag manufactured by Baxter) to which nothing was immobilized. Thereafter, 0.5% autologous plasma AIM V was then added thereto in an amount of 20 mL/bag each, and IL-2 was added thereto so as to have a final concentration of 500 U/mL. On the sixth day from the initiation of culture, 0.5% autologous plasma/AIM V was added thereto in an amount of 30 mL/bag each, and IL-2 was added thereto so as to have a final concentration of 500 U/mL. On the eighth day from the initiation of culture, a part of the culture medium was appropriately diluted, the dilution was then transferred to a 85 cm² $CO_2$ gas-permeable bag for cell culture (Optisite bag or X-Fold bag) to which nothing was immobilized, and IL-2 was added thereto so as to have a final concentration of 500 U/mL. On the eleventh and thirteenth days from the initiation of culture, IL-2 was added thereto so as to have a final concentration of 500 U/mL. On the fifteenth day from the initiation of culture, the number of living cells was counted by trypan blue staining method, and calculated as an expansion fold by comparing the number of the cells with the number at the initiation of culture. The results are shown in Table 46.

TABLE 46

| Plasma Concentration, Medium and $CO_2$ Gas-Permeable Bag for Cell Culture | PBMCs Donor | Cultured Days | Fibronectin Fragment | Expansion Fold (fold) |
|---|---|---|---|---|
| 0.5% Autologous Plasma AIM V and Optisite Bag | A | 15 Days | Control (Without Immobilization of FNfr) | ×22 |

TABLE 46-continued

| Plasma Concentration, Medium and $CO_2$ Gas-Permeable Bag for Cell Culture | PBMCs Donor | Cultured Days | Fibronectin Fragment | Expansion Fold (fold) |
|---|---|---|---|---|
| 0.5% Autologous Plasma AIM V and Optisite Bag | A | 15 Days | CH-296 | ×259 |
| 0.5% Autologous Plasma AIM V and X-Fold Bag | A | 15 Days | CH-296 | ×360 |
| 0.5% Autologous Plasma AIM V and Optisite Bag | B | 15 Days | Control (Without Immobilization of FNfr) | ×34 |
| 0.5% Autologous Plasma AIM V and Optisite Bag | B | 15 Days | CH-296 | ×432 |
| 0.5% Autologous Plasma AIM V and X-Fold Bag | B | 15 Days | CH-296 | ×360 |

As shown in Table 46, in the group using the flask for cell culture to which each of the fibronectin fragments was immobilized at an early stage of the induction of the LAK cells in the combination of the flask for cell culture and the $CO_2$ gas-permeable bag for cell culture using the medium (AIM V) containing low-concentration autologous plasma (0.5%), the expansion fold of LAK cells was high regardless of the kinds of the $CO_2$ gas-permeable bags for cell culture. It was clarified from the above that each of the fibronectin fragments was suitably used during the culture of LAK cells in the combination of the flask for cell culture and the $CO_2$ gas-permeable bag for cell culture using the medium containing a low-concentration plasma.

Example 47

Determination of Ratio of CD8-Positive Cells in LAK Cell Population Using Freshly Isolated PBMCs and Autologous Plasma-Containing Medium (With AIM V Medium Containing 0.5% Autologous Plasma, Culture in Combination of Flask for Cell Culture and $CO_2$ Gas-Permeable Bag for Cell Culture)

(1) Induction and Culture of LAK Cells

The induction and the culture of LAK cells were carried out in the same manner as in item (3) of Example 46. On the fifteenth day from the initiation of culture, in the same manner as in item (2) of Example 4, the content ratio of CD8-positive cells was determined. The results are shown in Table 47.

TABLE 47

| Plasma Concentration, Medium and $CO_2$ Gas-Permeable Bag for Cell Culture | PBMCs Donor | Cultured Days | Fibronectin Fragment | Ratio of CD8-Positive Cells (%) |
|---|---|---|---|---|
| 0.5% Autologous Plasma AIM V and Optisite Bag | B | 15 Days | Control (Without Immobilization of FNfr) | 45.0 |
| 0.5% Autologous Plasma AIM V and Optisite Bag | B | 15 Days | CH-296 | 89.8 |
| 0.5% Autologous Plasma AIM V and X-Fold Bag | B | 15 Days | CH-296 | 90.0 |

As shown in Table 47, in the group using the flask for cell culture to which each of the fibronectin fragments was immobilized at an early stage of the induction of LAK cells in the combination of the flask for cell culture and the $CO_2$ gas-permeable bag for cell culture using the medium (AIM V) containing the low-concentration autologous plasma (0.5%), the CD8 cell-positive ratio in LAK cells population was high regardless of the kinds of the $CO_2$ gas-permeable bags for cell culture. It was clarified from the above that each of the fibronectin fragments was suitably used during the culture of LAK cells in the combination of the flask for cell culture and the $CO_2$ gas-permeable bag for cell culture using the medium containing a low-concentration plasma.

Example 48

Determination of Expansion Fold in Culture System of LAK Cells Using Freshly Isolated PBMCs and Autologous Plasma-Containing Medium (With AIM V Medium Containing 0.5% Autologous Plasma, Culture in Combination of Flask for Cell Culture and $CO_2$ Gas-Permeable Bag for Cell Culture)

(1) Immobilization of Anti-Human CD3 Antibody and FN Fragment

An anti-human CD3 antibody and an FN fragment were immobilized to a culture equipment (25 cm² flask for cell culture) used in the following experiment, in the same manner as in item (1) of Example 35. Immediately before use, PBS containing the antibody and the FNfr was removed from the culture equipment, and each flask was washed twice with PBS and once with AIM V medium. Each experiment was carried out using the culture equipment.

(2) Induction and Culture of LAK Cells

Freshly isolated PBMCs which were prepared in the same manner as in item (1) of Example 46 were suspended in AIM V containing 0.5% autologous plasma (hereinafter simply referred to as 0.5% autologous plasma AIM V) so as to have a concentration of $1\times10^6$ cells/mL, and thereafter the cell suspension was placed in a flask immobilized with the anti-human CD3 antibody or a flask immobilized with the anti-human CD3 antibody and the FNfr, prepared in item (1) of Example 48, in an amount of 3 mL/flask each, and IL-2 was added thereto so as to have a final concentration of 1000 U/mL. These flasks were incubated at 37° C. in 5% $CO_2$ (zeroth day of culture). On the first day from the initiation of culture, 0.5% autologous plasma AIM V containing 1000 U/mL IL-2 was added thereto in an amount of 7 mL/flask each. On the fourth day from the initiation of culture, a culture medium was transferred to a 85 cm² $CO_2$ gas-permeable bag for cell culture (Optisite bag) to which nothing was immobilized, 0.5% autologous plasma AIM V was then added thereto in an amount of 20 mL/bag each, and IL-2 was added thereto so as to have a final concentration of 500 U/mL. On the sixth day from the initiation of culture, 0.5% autologous plasma/AIM V was added thereto in an amount of 30 mL/bag each, and IL-2 was added thereto so as to have a final concentration of 500 U/mL. On the eighth day from the initiation of culture, a part of the culture medium was appropriately diluted, the dilution was then transferred to a 85 cm² $CO_2$ gas-permeable bag (Optisite bag) for cell culture to which nothing was immobilized, and IL-2 was added thereto so as to have a final concentration of 500 U/mL. On the eleventh and thirteenth days from the initiation of culture, IL-2 was added thereto so as to have a final concentration of 500 U/mL.

In addition, similarly, a part (7 mL out of 10 mL) of a culture medium which was cultured until the fourth day was transferred to a 180 cm² $CO_2$ gas-permeable bag for cell culture to which nothing was immobilized, 0.5% autologous plasma AIM V was then added thereto in an amount of 58 mL/bag each, and IL-2 was added thereto so as to have a final concentration of 500 U/mL. On the sixth day from the initiation of culture, 0.5% autologous plasma/AIM V was added thereto in an amount of 65 mL/bag each, and IL-2 was added thereto so as to have a final concentration of 500 U/mL. On the eighth day from the initiation of culture, a part of the culture medium was appropriately diluted, the dilution was then transferred to a 180 cm² $CO_2$ gas-permeable bag for cell culture (Optisite bag) to which nothing was immobilized, and IL-2 was added thereto so as to have a final concentration of 500 U/mL. On the eleventh and thirteenth days from the initiation of culture, IL-2 was added thereto so as to have a final concentration of 500 U/mL. Upon the addition, there was also set a system in which 130 mL of 0.5% autologous plasma/AIM V was added on the eleventh day from the initiation of culture. On the fifteenth day from the initiation of culture, the number of living cells was counted by trypan blue staining method, and calculated as an expansion fold by comparing the number of the cells with the number at the initiation of culture. The results are shown in Table 48.

TABLE 48

| Plasma Concentration, Medium and $CO_2$ Gas-Permeable Bag for Cell Culture | Culture Area of Bag | Addition of Medium on Eleventh Day | Cultured Days | Fibronectin Fragment | Expansion Fold (fold) |
|---|---|---|---|---|---|
| 0.5% Autologous Plasma AIM V and Optisite Bag | 85 cm² | No | 15 Days | Control (Without Immobilization of FNfr) | ×22 |
| 0.5% Autologous Plasma AIM V and Optisite Bag | 85 cm² | No | 15 Days | CH-296 | ×259 |
| 0.5% Autologous Plasma AIM V and Optisite Bag | 180 cm² | No | 15 Days | CH-296 | ×473 |
| 0.5% Autologous Plasma AIM V and Optisite Bag | 180 cm² | Yes | 15 Days | CH-296 | ×911 |

As shown in Table 48, in the group using the flask for cell culture to which each of the fibronectin fragments was immobilized at an early stage of the induction of LAK cells in the combination of the flask for cell culture and the $CO_2$ gas-permeable bag for cell culture using the medium (AIM V) containing the low-concentration autologous plasma (0.5%), the expansion fold of LAK cells was high regardless of culture area, culture method, final amount of medium for the $CO_2$ gas-permeable bag for cell culture. It was clarified from the above that each of the fibronectin fragments was suitably used during the culture of LAK cells in the combination of the flask for cell culture and the $CO_2$ gas-permeable bag for cell culture using the medium containing a low-concentration plasma.

Example 49

Determination of Ratio of CD8-Positive Cells in LAK Cell Population Using Freshly Isolated PBMCs and Autologous Plasma-Containing Medium (With AIM V Medium Containing 0.5% Autologous Plasma, Culture in Combination of Flask for Cell Culture and $CO_2$ Gas-Permeable Bag for Cell Culture)

(1) Induction and Culture of LAK Cells

The induction and the culture of LAK cells were carried out in the same manner as in item (2) of Example 48. On the fifteenth day from the initiation of culture, the content ratio of CD8-positive cells was determined in the same manner as in item (2) of Example 4. The results are shown in Table 49.

TABLE 49

| Plasma Concentration, Medium and CO$_2$ Gas-Permeable Bag for Cell Culture | Culture Area of Bag | Addition of Medium on Eleventh Day | Cultured Days | Fibronectin Fragment | Content Ratio of CD8-Positive Cells (%) |
|---|---|---|---|---|---|
| 0.5% Autologous Plasma AIM V and Optisite Bag | 85 cm$^2$ | No | 15 Days | Control (Without Immobilization of FNfr) | 37.4 |
| 0.5% Autologous Plasma AIM V and Optisite Bag | 85 cm$^2$ | No | 15 Days | CH-296 | 70.0 |
| 0.5% Autologous Plasma AIM V and Optisite Bag | 180 cm$^2$ | No | 15 Days | CH-296 | 56.2 |
| 0.5% Autologous Plasma AIM V and Optisite Bag | 180 cm$^2$ | Yes | 15 Days | CH-296 | 58.4 |

As shown in Table 49, in the group using the flask for cell culture to which each of the fibronectin fragments was immobilized at an early stage of the induction of LAK cells in the combination of the flask for cell culture and the CO$_2$ gas-permeable bag for cell culture using the medium (AIM V) containing the low-concentration autologous plasma (0.5%), the CD8 cell-positive ratio in the LAK cell population was high regardless of culture area, culture method, final amount of medium for the CO$_2$ gas-permeable bag for cell culture. It was clarified from the above that each of the fibronectin fragments was suitably used during the culture of LAK cells in the combination of the flask for cell culture and the CO$_2$ gas-permeable bag for cell culture using the medium containing a low-concentration plasma.

Example 50

Determination of Cytotoxic Activity in Culture System of LAK Cells Using Freshly Isolated PBMCs and Autologous Plasma-Containing Medium) (With AIM V Medium Containing 0.5% Autologous Plasma, and Culture in Combination of Flask for Cell Culture and CO$_2$ Gas-Permeable Bag for Cell Culture)

(1) Induction and Culture of LAK Cells

The induction and the culture of LAK cells were carried out in the same manner as in item (3) of Example 46.

(2) Determination of Cytotoxic Activity of Cultured LAK Cells

The cytotoxic activity of LAK on the fifteenth day after the culture was determined in the same manner as in item (2) of Example 25. The results are shown in Table 50.

TABLE 50

| Plasma Concentration, Medium and CO$_2$ Gas-Permeable Bag for Cell Culture | Cultured Days | Fibronectin Fragment | E/T | Cytotoxic Activity (%) (Target Cells K562) | Cytotoxic Activity (%) (Target Cells Daudi) |
|---|---|---|---|---|---|
| 0.5% Autologous Plasma AIM V and Optisite Bag | 15 Days | Control (Without Immobilization of FNfr) | 90 30 10 | 50.9 32.9 16.9 | 56.2 49.6 35.7 |
| 0.5% Autologous Plasma AIM V and Optisite Bag | 15 Days | CH-296 | 90 30 10 | 75.9 48.3 19.6 | 62.3 53.7 40.2 |

As shown in Table 50, in the group using a flask for cell culture to which each of the fibronectin fragments was immobilized at an early stage of the induction of LAK cells in the combination of the flask for cell culture and the CO$_2$ gas-permeable bag for cell culture using the medium (AIM V) containing the low-concentration autologous plasma (0.5%), the cytotoxic activity of LAK cells was high as compared to that of the control group. It was clarified from the above that each of the fibronectin fragments was suitably used during the culture of LAK cells in the combination of the flask for cell culture and the CO$_2$ gas-permeable bag for cell culture using the medium containing a low-concentration plasma.

Example 51

Determination of Expansion Fold in Culture System of LAK Cells Using Freshly Isolated PBMCs and Autologous Plasma-Containing Medium (With AIM V Medium Containing 0.5% Autologous Plasma and Culture in Combination of Flask for Cell Culture and CO$_2$ Gas-Permeable Bag for Cell Culture)

(1) Immobilization of Anti-Human CD3 Antibody and FN Fragment

An anti-human CD3 antibody and an FN fragment were immobilized to a culture equipment (25 cm$^2$ flask for cell culture) used in the following experiment, in the same manner as in item (1) of Example 35. Immediately before use, PBS containing the antibody and the FNfr was removed from the culture equipment, and each flask was twice washed with PBS, and once with AIM V medium. Each experiment was carried out using the culture equipment.

(2) Induction and Culture of LAK Cells

Freshly isolated PBMCs which were prepared in the same manner as in item (1) of Example 46 were suspended in AIM V containing 0.5% autologous plasma (hereinafter simply referred to as 0.5% autologous plasma AIM V), so as to have a concentration of $5 \times 10^5$ cells/mL (provided that the number of living cells was counted using Tulk solution (manufactured by Kanto Kagaku)), the cell suspension was then placed in a flask immobilized with the anti-human CD3 antibody or a flask immobilized with the anti-human CD3 antibody and the FNfr, prepared in item (1) of Example 51, in an amount of 3 mL/flask each, and IL-2 was added thereto so as to have a final concentration of 1000 U/mL. These flasks were incubated at 37° C. in 5% $CO_2$ (zeroth day of culture). On the first day from the initiation of culture, 0.5% autologous plasma AIM V containing 1000 U/mL IL-2 was added thereto in an amount of 7 mL/flask each. On the fourth day from the initiation of culture, a part (7 mL out of 10 mL) of the culture medium was transferred to a 180 cm$^2$ $CO_2$ gas-permeable bag for cell culture to which nothing was immobilized, 0.5% autologous plasma AIM V was then added thereto in an amount of 58 mL/bag each, and IL-2 was added thereto so as to have a final concentration of 500 U/mL. On the sixth day from the initiation of culture, 0.5% autologous plasma/AIM V was added thereto in an amount of 65 mL/bag each, and IL-2 was added thereto so as to have a final concentration of 500 U/mL. On the eighth day from the initiation of culture, a part of the culture medium was appropriately diluted, the dilution was transferred to a 180 cm$^2$ $CO_2$ gas-permeable bag for cell culture (Optisite bag) to which nothing was immobilized, and IL-2 was added thereto so as to have a final concentration of 500 U/mL. On the eleventh and thirteenth days from the initiation of culture, IL-2 was added thereto so as to have a final concentration of 500 U/mL. Upon the addition, there was also set a system in which 130 mL of AIM V without containing autologous plasma or with 0.5% autologous plasma/AIM V was added on the eleventh day from the initiation of culture. On the fifteenth day from the initiation of culture, the number of living cells was counted by trypan blue staining method, and calculated as an expansion fold by comparing the number of the cells with the number at the initiation of culture. The results are shown in Table 51.

TABLE 51

| Plasma Concentration, Medium and $CO_2$ Gas-Permeable Bag for Cell Culture | PBMCs Donor | Addition of Medium on Eleventh Day | Medium Added on Eleventh Day | Fibronectin Fragment | Expansion Fold (fold) |
|---|---|---|---|---|---|
| 0.5% Autologous Plasma AIM V and Optisite Bag | C | No | No | Control (Without Immobilization of FNfr) | ×570 |
| | | No | No | CH-296 | ×1034 |
| | | Yes | 0.5% Autologous Plasma AIM V | CH-296 | ×1857 |
| | | Yes | 0% Autologous Plasma AIM V | CH-296 | ×1882 |
| 0.5% Autologous Plasma AIM V and Optisite Bag | D | No | No | Control (Without Immobilization of FNfr) | ×947 |
| | | No | No | CH-296 | ×1213 |
| | | Yes | 0.5% Autologous Plasma AIM V | CH-296 | ×1647 |
| | | Yes | 0% Autologous Plasma AIM V | CH-296 | ×1832 |
| 0.5% Autologous Plasma AIM V and Optisite Bag | E | No | No | Control (Without Immobilization of FNfr) | ×743 |
| | | No | No | CH-296 | ×931 |
| | | Yes | 0.5% Autologous Plasma AIM V | CH-296 | ×1960 |
| | | Yes | 0% Autologous Plasma AIM V | CH-296 | ×1747 |

As shown in Table 51, in the group using the flask for cell culture to which each of the fibronectin fragments was immobilized at an early stage of the induction of LAK cells in the combination of the flask for cell culture and the $CO_2$ gas-permeable bag for cell culture using the medium (AIM V) containing the low-concentration autologous plasma (0.5%), the expansion fold of LAK cells was high regardless of culture area, culture method, final amount of medium for the $CO_2$ gas-permeable bag for cell culture. It was clarified from the above that each of the fibronectin fragments was suitably used during the culture of LAK cells in the combination of the flask for cell culture and the $CO_2$ gas-permeable bag for cell culture using the medium containing a low-concentration plasma.

Example 52

Determination of Ratio of CD8-Positive Cells in LAK Cell Population Using Freshly Isolated PBMCs and Autologous Plasma-Containing Medium (With AIM V Medium Containing 0.5% Autologous Plasma, Culture in Combination of Flask for Cell Culture and $CO_2$ Gas-Permeable Bag for Cell Culture)

(1) Induction and Culture of LAK Cells

The induction and the culture of LAK cells were carried out in the same manner as in item (2) of Example 51. On the fifteenth day from the initiation of culture, the content ratio of CD8-positive cells was determined in the same manner as in item (2) of Example 4. The results are shown in Table 52.

TABLE 52

| Plasma Concentration, Medium and $CO_2$ Gas-Permeable Bag for Cell Culture | PBMCs Donor | Addition of Medium on Eleventh Day | Medium Added on Eleventh Day | Fibronectin Fragment | Ratio of CD8-Positive Cells (%) |
|---|---|---|---|---|---|
| 0.5% Autologous Plasma AIM V and Optisite Bag | C | No | No | Control (Without Immobilization of FNfr) | 59.1 |
| | | No | No | CH-296 | 80.8 |
| | | Yes | 0.5% Autologous Plasma AIM V | CH-296 | 83.3 |
| | | Yes | 0% Autologous Plasma AIM V | CH-296 | 83.6 |
| 0.5% Autologous Plasma AIM V and Optisite Bag | D | No | No | Control (Without Immobilization of FNfr) | 77.2 |
| | | No | No | CH-296 | 83.4 |
| | | Yes | 0.5% Autologous Plasma AIM V | CH-296 | 84.0 |
| | | Yes | 0% Autologous Plasma AIM V | CH-296 | 85.9 |
| 0.5% Autologous Plasma AIM V and Optisite Bag | E | No | No | Control (Without Immobilization of FNfr) | 72.6 |
| | | No | No | CH-296 | 84.6 |
| | | Yes | 0.5% Autologous Plasma AIM V | CH-296 | 86.8 |
| | | Yes | 0% Autologous Plasma AIM V | CH-296 | 89.4 |

As shown in Table 52, in the group using the flask for cell culture to which each of the fibronectin fragments was immobilized at an early stage of the induction of LAK cells in the combination of the flask for cell culture and the $CO_2$ gas-permeable bag for cell culture using the medium (AIM V) containing a low-concentration autologous plasma (0.5%), the ratio of CD8-positive cells in the LAK cell population was high regardless of culture area, culture method, final amount of medium for the $CO_2$ gas-permeable bag for cell culture. It was clarified from the above that each of the fibronectin fragments was suitably used during the culture of LAK cells in the combination of the flask for cell culture and the $CO_2$ gas-permeable bag for cell culture using the medium containing a low-concentration plasma.

Example 53

Induction of IL-2 Receptor (IL-2R) Expression in Culture System of LAK Cells Using Low-Serum Medium (AIM V)

(1) Induction and Culture of LAK Cells

The induction and the culture of LAK cells were carried out in the same manner as in item (3) of Example 1. Upon the induction and the culture, a medium to be used was changed to AIM V medium containing 1% human AB serum.

(2) Determination of Ratio of IL-2R Expression in LAK Cells

The content ratio of the IL-2R expression-positive cells was determined in the same manner as in item (2) of Example 3. The results are shown in Table 53. In the table, the content ratio of IL-2R expression-positive cells (%) is shown as the ratio of IL-2R expression (%).

TABLE 53

| Serum Concentration and Medium | Fibronectin Fragment | Ratio of IL-2R Expression (%) |
|---|---|---|
| 1% AIM V | Control (Without Immobilization of FNfr) | 23.5 |
| 1% AIM V | CH-296 | 27.2 |

As shown in Table 53, in the group using the culture equipment to which each of the fibronectin fragments was immobilized at an early stage of the induction of LAK cells using AIM V medium containing a low-concentration serum, the ratio of IL-2R expression on the surface of LAK cells during culture could be induced at a high level. In other words, it was clarified that, the LAK cells could be induced and cultured with increasing the ratio of IL-2R expression using the medium containing a low-concentration serum, in the copresence of the fibronectin fragment during the induction of LAK cells.

Example 54

Expression of Retronectin Mutant Protein (CH-296Na)

(1) Construction of CH-296Na Expression Vector

PCR was carried out using synthetic DNA primers of SEQ ID NOs: 27 and 28 (Primer CH-296Na1 and Primer CH-296Na2, respectively), with pCH102, a CH-296 expression vector, as a template. The resulting DNA fragment was treated with restriction enzymes NdeI and HindIII. On the other hand, a pCold14ND2 vector was prepared, having an NdeI site at a translation initiation codon prepared from pCold04 described in Example 5 of WO 99/27117 Pamphlet in accordance with the method of Example 4 of the same pamphlet. The above-mentioned DNA fragment was inserted into an NdeI-HindIII restriction enzyme site of the pCold14ND2 vector to give a vector pCold14ND2-CH296. Next, PCR was carried out with a pLF2435 vector having a cDNA encoding from a part to a C-terminal of a cell binding domain of fibronectin as a template, using synthetic DNA primers of SEQ ID NOs: 28 and 29 (Primer CH-296Na2 and Primer CH-296Na3, respectively). The resulting DNA fragment was treated with restriction enzymes BamHI and HindIII. The DNA fragment thus obtained was ligated with a product obtained by treating pCold14ND2-CH296 with restriction enzymes BamHI and HindIII, to prepare a vector for expressing CH-296Na.

(2) Expression and Purification of CH-296Na

*Escherichia coli* BL21 was transformed using pCold14-CH296Na prepared in the above-mentioned item (1) of Example 54, and the resulting transformant was grown on LB medium (containing 50 μg/mL ampicillin) containing agar having a 1.5% (w/v) concentration. The grown colony was inoculated on 30 mL LB liquid medium (containing 50 μg/mL ampicillin), and the colony was cultured overnight at 37° C. A whole amount of cultured cells was inoculated on 3 L of the same LB medium, and the cells were cultured at 37° C. up to a logarithmic growth phase. Upon this culture, a 5 L minijar fermenter (manufactured by Biott) was used, and the culture was carried out under the conditions of 150 rpm and Air=1.0 L/min. After the above-mentioned culture, the culture medium was cooled to 15° C., IPTG was then added thereto so as to have a final concentration of 1.0 mM, and the culture was carried out in this state at 15° C. for 24 hours to induce expression. Thereafter, bacterial cells were harvested by centrifugation, and resuspended in a cell disruption solution [50 mM Tris-HCl (pH 7.5), 1 mM EDTA, 1 mM DTT, 1 mM PMSF, 50 mM NaCl] in an amount of 4 times the volume of the bacterial cells. The bacterial cells were disrupted by ultrasonic disruption, and the disruption was centrifuged (11,000 rpm, 20 minutes) to separate the disruption into an extract of supernatant and precipitates. The supernatant was dialyzed against 2 L of a buffer A [50 mM Tris-HCl (pH 7.5), 50 mM NaCl], and about 40 mL of the resulting solution was used for further purification by ion-exchange chromatography as follows.

Concretely, a column (ϕ4 cm, 20 cm) of SP-Sepharose (manufactured by Amersham Pharmacia) having a resin volume corresponding to 100 mL, saturated with the buffer A was furnished, and the dialyzed sample was applied to the column. The column was washed with 300 mL of the buffer A, and thereafter the elution from the column was carried out using, in order, 200 mL each of a buffer B [50 mM Tris-HCl (pH 7.5), 200 mM NaCl], a buffer C [50 mM Tris-HCl (pH 7.5), 300 mM NaCl], and a buffer D [50 mM, Tris-HCl (pH 7.5), 500 mM NaCl], and an about 100 mL portion each was collected, to give fractions 1 to 6. The collected fractions were subjected to 10% SDS-PAGE, and consequently, fractions 2 and 3 (about 200 mL) which were found to contain the desired protein having a molecular weight of about 71 kDa in a large amount were collected, and dialyzed against 2 L of the buffer A.

Next, a column (ϕ3 cm, 16 cm) of Q-Sepharose (manufactured by Amersham Pharmacia) having a resin volume corresponding to 50 mL, saturated with the buffer A was furnished, and the dialyzed sample was applied to the column. The column was washed with 200 mL of the buffer A, and thereafter the elution from the column was carried out using, in order, 150 mL each of a buffer E [50 mM Tris-HCl (pH 7.5), 140 mM NaCl], the buffer B, and the buffer C, and an about 100 mL portion each was collected, to give fractions 1 to 5. Those fractions were subjected to 10% SDS-PAGE, and consequently a fraction 1 which was found to contain only the desired protein in a large amount, was collected in an amount of about 100 mL, and dialyzed against 2 L of a buffer F [50 mM sodium carbonate buffer, pH 9.5].

Subsequently, the dialyzed fraction was concentrated about 4 times to a volume of 25 mL, with Centricone-10 (manufactured by Millipore Corporation), and the concentrate was confirmed by 10% SDS-PAGE. Consequently, the desired protein having a molecular weight of about 71 kDa was detected as an approximately single band, which was named as CH-296Na. Thereafter, a protein concentration was determined using a MicroBCA kit (manufactured by Pierce). As a result, the protein concentration was found to be 3.8 mg/mL.

Example 55

Determination of Expansion Fold in Culture System of LAK Cells Using Low-Serum Medium (AIM V) (Serum Concentrations 5%→1%→0%→0%, 5%→1%→0.05%→0.05%, 3%→1%→0.05%→0.05%, 3%→1%→0.1%→0.05%, 1%→1%→0.1%→0.05%)

From the same viewpoint as that of Example 43, and the influence of the serum concentration on the culture system of LAK cells was confirmed, taking a plasma concentration obtained by collecting 30 mL blood into consideration.

There were respectively set a group containing a human AB serum concentration of 5%, 3% or 1% at the initiation of culture, and a group subsequently diluted with AIM V medium containing a human AB serum concentration as shown in the following Table 54. Here, groups in which the subculture concentrations were changed on each subculture day as shown in the following Table 54 were set, respectively.

tration pattern 1-1 was diluted with AIM V without containing human AB serum (amount of liquid: 12.6 mL) so as to have a concentration of $0.321 \times 10^6$ cells/mL, groups in which the culture was carried out in the serum concentration patterns 1-2 and 2-1 were diluted with AIM V containing 0.05% human AB serum (amount of liquid: 12.6 mL) so as to have a concentration of $0.321 \times 10^6$ cells/mL, and each of the groups

TABLE 54

| | | Serum Concentration Patterns | | | |
|---|---|---|---|---|---|
| | | on Zeroth Day from Initiation of Culture | on Fourth Day from Initiation of Culture | on Seventh Day from Initiation of Culture | on Tenth Day from Initiation of Culture |
| Serum Concentration Pattern 1-1 | Serum Concentration | 5% | 1% | 0% | 0% |
| | Subculture Concentration | — | 0.1 | 0.321 | 0.873 |
| Serum Concentration Pattern 1-2 | Serum Concentration | 5% | 1% | 0.05% | 0.05% |
| | Subculture Concentration | — | 0.2 | 0.321 | 0.841 |
| Serum Concentration Pattern 2-1 | Serum Concentration | 3% | 1% | 0.05% | 0.05% |
| | Subculture Concentration | — | 0.1 | 0.321 | 0.746 |
| Serum Concentration Pattern 2-2 | Serum Concentration | 3% | 1% | 0.1% | 0.05% |
| | Subculture Concentration | — | 0.2 | 0.321 | 0.643 |
| Serum Concentration Pattern 3-1 | Serum Concentration | 1% | 1% | 0.1% | 0.05% |
| | Subculture Concentration | — | 0.1 | 0.321 | 0.643 |
| Serum Concentration Pattern 3-2 | Serum Concentration | 1% | 1% | 0.1% | 0.05% |
| | Subculture Concentration | — | 0.05 | 0.417 | 1.214 |
| Serum Concentration Pattern 3-3 | Serum Concentration | 1% | 1% | 0.1% | No Subculture, No Addition of Medium |
| | Subculture Concentration | — | 0.05 | 0.23 | |

*Cell Subculture Concentration: ($\times 10^6$ cells/mL)
*Serum concentrations in the table are the concentrations at the initiation for the zeroth day from the initiation of culture, and serum concentrations contained in the medium used for dilution for the subsequent days.

PBMCs which were prepared in item (1) of Example 1 were suspended in AIM V containing 5%, 3% or 1% human AB serum so as to have a concentration of $0.33 \times 10^6$ cells/mL, and thereafter the suspension was put on a plate immobilized with the anti-human CD3 antibody or a plate immobilized with the anti-human CD3 antibody and CH-296, prepared in item (1) of Example 41, in a volume of 3 mL/well each, and IL-2 was added thereto so as to have a final concentration of 1000 U/mL. These plates were incubated at 37° C. in 5% $CO_2$ (zeroth day of culture).

On the fourth day from the initiation of culture, each of the groups was diluted with AIM V containing 1% human AB serum (amount of liquid: 6 mL) so as to have a concentration of $0.1 \times 10^6$ cells/mL for groups in which the culture was carried out under the serum concentration patterns 1-1, 2-1 and 3-1, or so as to have a concentration of $0.2 \times 10^6$ cells/mL for groups in which the culture was carried out under the serum concentration patterns 1-2 and 2-2, or so as to have a concentration of $0.05 \times 10^6$ cells/mL for groups in which the culture was carried out under the serum concentration patterns 3-2 and 3-3. The dilution was transferred to a 12.5 cm² cell culture flask to which nothing was immobilized. In each group, IL-2 was added thereto so as to have a final concentration of 500 U/mL.

On the seventh day from the initiation of culture, the group in which the culture was carried out under the serum concentration pattern 1-1 was diluted with AIM V containing 0.1% human AB serum (amount of liquid: 12.6 mL), so as to have a concentration of $0.321 \times 10^6$ cells/mL for groups in which the culture was carried out under the serum concentration patterns 2-2 and 3-1, or so as to have a concentration of $0.417 \times 10^6$ cells/mL for the group in which the culture was carried out under the serum concentration pattern 3-2, or so as to have a concentration of $0.23 \times 10^6$ cells/mL for the group in which the culture was carried out under the serum concentration pattern 3-3, respectively. Each group was transferred to a fresh 25 cm² cell culture flask kept upright to which nothing was immobilized. In each group, IL-2 was added thereto so as to have a final concentration of 500 U/mL.

On the tenth day from the initiation of culture, the group in which the culture was carried out under the serum concentration pattern 1-1 was diluted with AIM V without containing human AB serum (amount of liquid: 12.6 mL) so as to have a concentration of $0.873 \times 10^6$ cells/mL, and each of the groups was diluted with AIM V containing 0.05% human AB serum (amount of liquid: 12.6 mL), so as to have a concentration of $0.841 \times 10^6$ cells/mL for the group in which the culture was carried out under the serum concentration pattern 1-2, or so as to have a concentration of $0.746 \times 10^6$ cells/mL for the group in which the culture was carried out under the serum concentration pattern 2-1, or so as to have a concentration of $0.643 \times 10^6$ cells/mL for the groups in which the culture was carried out under the serum concentration patterns 2-2 and 3-1, or so as to have a concentration of $1.214 \times 10^6$ cells/mL for the group in which the culture was carried out under the serum concentration pattern 3-2, respectively. The dilution was transferred to a fresh 25 cm² cell culture flask kept upright to which nothing was immobilized. In each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in Table 55.

TABLE 55

| | Stimulation on Zeroth Day from Initiation of Culture | Expansion Fold (fold) |
|---|---|---|
| Serum Concentration Pattern 1-1 | Anti-CD3 | 460 |
| | Anti-CD3 + CH-296 | 708 |

TABLE 55-continued

| | Stimulation on Zeroth Day from Initiation of Culture | Expansion Fold (fold) |
|---|---|---|
| Serum Concentration Pattern 1-2 | Anti-CD3 | 354 |
| | Anti-CD3 + CH-296 | 616 |
| Serum Concentration Pattern 2-1 | Anti-CD3 | 338 |
| | Anti-CD3 + CH-296 | 630 |
| Serum Concentration Pattern 2-2 | Anti-CD3 | 289 |
| | Anti-CD3 + CH-296 | 514 |
| Serum Concentration Pattern 3-1 | Anti-CD3 | 317 |
| | Anti-CD3 + CH-296 | 551 |
| Serum Concentration Pattern 3-2 | Anti-CD3 | 243 |
| | Anti-CD3 + CH-296 | 587 |
| Serum Concentration Pattern 3-3 | Anti-CD3 | 257 |
| | Anti-CD3 + CH-296 | 564 |

As shown in Table 55, during the culture of LAK cells using AIM V medium containing each serum concentration, in any of serum concentration groups and in any of subculture concentration group, a high expansion fold was obtained in the group stimulated with CH-296 and the anti-CD3 antibody as compared to that of the control group (stimulation only with anti-CD3 antibody). In other words, in the culture of LAK cells at a serum concentration on the assumption of 30 mL blood collection, the LAK cells could be clearly induced and cultured at a high expansion fold by stimulation with CH-296 and the anti-CD3 antibody than the stimulation with only the anti-CD3 antibody. In addition, the cells during this culture were in a high concentration and at a high density, and the expansion fold was clearly high by stimulation with CH-296 even under the conditions mentioned above, so that the effectiveness of CH-296 was found.

Example 56

Determination of Expansion Fold in Culture System of LAK Cells Using Low-Serum Medium (AIM V)(IL-2 concentrations 100 U/mL→150 U/mL→150 U/mL→300 U/mL, 200 U/mL→300 U/mL→300 U/mL→400 U/mL, 1000 U/mL→500 U/mL→500 U/mL→500 U/mL)

The influence of IL-2 concentration on the culture system of LAK cells was confirmed.

IL-2 concentrations to be added at the initiation of culture and during the subculture were set as shown in the following Table 56-1.

TABLE 56-1

| | on Zeroth Day from Initiation of Culture | on Fourth Day from Initiation of Culture | on Seventh Day from Initiation of Culture | on Tenth Day from Initiation of Culture |
|---|---|---|---|---|
| IL-2 Concentration Pattern 1 | 100 | 150 | 150 | 300 |
| IL-2 Concentration Pattern 2 | 200 | 300 | 300 | 400 |
| IL-2 Concentration Pattern 3 | 1000 | 500 | 500 | 500 |

*IL-2 concentration (U/mL)

PBMCs which were prepared in item (1) of Example 1 were suspended in AIM V containing 3% human AB serum so as to have a concentration of $0.33 \times 10^6$ cells/mL, and thereafter the suspension was put on a plate immobilized with the anti-human CD3 antibody or a plate immobilized with the anti-human CD3 antibody and CH-296, prepared in item (1) of Example 41, in a volume of 3 mL/well each, and IL-2 was added thereto so as to have a final concentration of 100 U/mL, 200 U/mL or 1000 U/mL. These plates were incubated at 37° C. in 5% $CO_2$ (zeroth day of culture).

On the fourth day from the initiation of culture, each group was diluted with AIM V containing 1% human AB serum (amount of liquid: 6 mL) so as to have a concentration of $0.1 \times 10^6$ cells/mL, and the dilution was transferred to a 12.5 cm² cell culture flask to which nothing was immobilized. IL-2 was added thereto so as to have a final concentration of 150 U/mL in the IL-2 concentration pattern 1, or so as to have a final concentration of 300 U/mL in the IL-2 concentration pattern 2, or so as to have a final concentration of 500 U/mL in the IL-2 concentration pattern 3, respectively.

On the seventh day from the initiation of culture, each group was diluted with AIM V containing 0.05% human AB serum (amount of liquid: 12.6 mL) so as to have a concentration of $0.262 \times 10^6$ cells/mL, and the dilution was transferred to a fresh 25 cm² cell culture flask kept upright to which nothing was immobilized. IL-2 was added thereto so as to have a final concentration of 150 U/mL in the IL-2 concentration pattern 1, or so as to have a final concentration of 300 U/mL in the IL-2 concentration pattern 2, or so as to have a final concentration of 500 U/mL in the IL-2 concentration pattern 3, respectively.

On the tenth day from the initiation of culture, each group was diluted with AIM V containing 0.05% human AB serum (amount of liquid: 12.6 mL) so as to have a concentration of $0.585\times10^6$ cells/mL, and the dilution was transferred to a fresh 25 cm² cell culture flask kept upright to which nothing was immobilized. IL-2 was added thereto so as to have a final concentration of 300 U/mL in the IL-2 concentration pattern 1, or so as to have a final concentration of 400 U/mL in the IL-2 concentration pattern 2, or so as to have a final concentration of 500 U/mL in the IL-2 concentration pattern 3.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in Table 56-2.

TABLE 56-2

| | Stimulation on Zeroth Day from Initiation of Culture | Expansion Fold (fold) |
|---|---|---|
| IL-2 Concentration Pattern 1 | Anti-CD3 | 312 |
| | Anti-CD3 + CH-296 | 522 |
| IL-2 Concentration Pattern 2 | Anti-CD3 | 331 |
| | Anti-CD3 + CH-296 | 730 |
| IL-2 Concentration Pattern 3 | Anti-CD3 | 146 |
| | Anti-CD3 + CH-296 | 571 |

As shown in Table 56-2, during the culture of LAK cells in which the culture was carried out in various IL-2 concentrations during the subculture, in any of the IL-2 concentration groups, a high expansion fold was obtained in the group stimulated with CH-296 and the anti-CD3 antibody as compared to that of the control group (stimulation only with anti-CD3 antibody). In other words, even when the IL-2 concentrations were changed, the LAK cells could be induced and cultured clearly at a high expansion fold by stimulation with CH-296 and the anti-CD3 antibody, than that of stimulation only with the anti-CD3 antibody. In addition, the cells during this culture were in a high concentration and at a high density. Also, the serum concentration was set assuming that blood is collected in a volume of 30 mL, and a total amount of the culture medium is 10 L, and the expansion fold was clearly high even under the conditions mentioned above by stimulation with CH-296, so that the effectiveness of CH-296 was found.

Example 57

Content Ratio of CD8-Positive Cells in LAK Cell Population Cultured Using Low-Serum Medium (AIM V) (Studies on IL-2 Concentration)

(1) Induction and Culture of LAK Cells

The induction and the culture of LAK cells were carried out in the same manner as in Example 56.

(2) Determination of Content Ratio of CD8-Positive Cell Population in LAK Cells

The content ratio of the CD8-positive cells was determined in the same manner as in item (2) of Example 4. The results are shown in Table 57.

TABLE 57

| | Stimulation on Zeroth Day from Initiation of Culture | Content Ratio of CD8-Positive Cells (%) |
|---|---|---|
| IL-2 Concentration Pattern 1 | Anti-CD3 | 60 |
| | Anti-CD3 + CH-296 | 65 |
| IL-2 Concentration Pattern 2 | Anti-CD3 | 60 |
| | Anti-CD3 + CH-296 | 62 |
| IL-2 Concentration Pattern 3 | Anti-CD3 | 59 |
| | Anti-CD3 + CH-296 | 67 |

As shown in Table 57, in any of the groups in which the IL-2 concentrations were changed at the initiation of culture or during the subculture, the content ratio of the CD8-positive cells in LAK cells during the culture could be induced at a high level in the group stimulated with CH-296 and the anti-CD3 antibody as compared to that of the control group (stimulated only with anti-CD3 antibody). In other words, it was clarified that the LAK cells could be clearly induced and cultured while increasing the content ratio of the CD8-positive cells in the LAK cells by stimulation with CH-296, even when the IL-2 concentrations were changed.

Example 58

Determination of Expansion Fold in Culture System of LAK Cells Using Low-Serum Medium (AIM V) (Studies on Initial Concentration at Initiation of Culture)

The influence of the initial cell concentration at the initiation of culture on the expansion fold in the culture system of LAK Cells on the assumptions of 30 mL blood collection, and about 10 L of a final culture medium amount was confirmed.

Each group having an initial cell concentration at the initiation of culture of $0.083\times10^6$ cells/mL, $0.167\times10^6$ cells/mL or $0.33\times10^6$ cells/mL was set.

(1) Immobilization of Anti-Human CD3 Antibody and FN Fragment

An anti-human CD3 antibody and an FN fragment were immobilized to a culture equipment used in the following experiment. Concretely, 1.9 mL each or 4.8 mL each of PBS containing the anti-human CD3 antibody (final concentration: 5 µg/mL) was added to a 12-well cell culture plate or a 6-well cell culture plate (manufactured by Falcon). Upon the addition, a fibronectin fragment (CH-296) described in Preparation Example 1 was added to a group with addition of an FN fragment so as to have a final concentration of 25 µg/mL. As a control, there was also set a group without addition of CH-296.

These culture equipments were incubated at room temperature for 5 hours, and stored at 4° C. until use. Immediately before use, PBS containing the anti-human CD3 antibody and CH-296 was removed by aspiration from these culture equipments, and each well was washed twice with PBS, and once with RPMI medium. Each experiment was carried out using the culture equipment.

(2) Induction and Culture of LAK Cells

PBMCs which were prepared in item (1) of Example 1 were suspended in AIM V containing 3% human AB serum so as to have a concentration of $0.083\times10^6$ cells/mL, $0.167\times10^6$ cells/mL or $0.33\times10^6$ cells/mL. Thereafter, the suspension was put on a 6-well cell culture plate immobilized with the anti-human CD3 antibody or a 6-well cell culture plate immobilized with the anti-human CD3 antibody and CH-296, prepared in item (1) of Example 58, in a volume of 7.5 mL/well each, in a group in which the culture was initiated at a concentration of 0.083×10⁶ cells/mL or 0.167×10⁶ cells/mL; or the suspension was put on a 12-well cell culture plate immobilized with the anti-human CD3 antibody or a 12-well cell culture plate immobilized with the anti-human CD3 antibody and CH-296, prepared in item (1) of Example 58, in a volume of 3 mL/well each, in a group in which the culture was initiated at 0.33×10⁶ cells/mL. IL-2 was added thereto so as to have a final concentration of 1000 U/mL. These plates were incubated at 37° C. in 5% $CO_2$ (zeroth day of culture).

On the fourth day from the initiation of culture, each group was diluted with AIM V containing 1% human AB serum (amount of liquid: 6 mL) so as to have a maximum concentration of 0.1×10⁶ cells/mL, and the dilution was transferred to a 12.5 cm² cell culture flask to which nothing was immobilized. In each group, IL-2 was added thereto so as to have a final concentration of 500 U/mL.

On the seventh day from the initiation of culture, each group was diluted with AIM V containing 0.05% human AB serum (maximum amount of liquid: 12.6 mL), so as to have a concentration of 0.227×10⁶ cells/mL for the group in which culture was initiated at a concentration of 0.083×10⁶ cells/mL, or so as to have a concentration of 0.276×10⁶ cells/mL for the group in which culture was initiated at a concentration of 0.167×10⁶ cells/mL, or so as to have a concentration of 0.465×10⁶ cells/mL for the group in which culture was initiated at a concentration of 0.33×10⁶ cells/mL, respectively. The dilution was transferred to a fresh 25 cm² cell culture flask kept upright to which nothing was immobilized. In each group, Il-2 was added thereto so as to have a final concentration of 500 U/mL.

On the tenth day from the initiation of culture, each group was diluted with AIM V containing 0.05% human AB serum (amount of liquid: 12.6 mL), so as to have a concentration of 0.58×10⁶ cells/mL for the group in which culture was initiated at a concentration of 0.083×10⁶ cells/mL, so as to have a concentration of 0.75×10⁶ cells/mL for the group in which culture was initiated at a concentration of 0.167×10⁶ cells/mL, or so as to have a concentration of 0.79×10⁶ cells/mL for the group in which culture was initiated at a concentration of 0.33×10⁶ cells/mL, respectively. The dilution was transferred to a fresh 25 cm² cell culture flask kept upright to which nothing was immobilized. In each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in Table 58.

TABLE 58

| Initial Cell Concentration at Initiation of Culture (×10⁶ cells/mL) | Stimulation on Zeroth Day from Initiation of Culture | Expansion Fold (fold) |
|---|---|---|
| 0.083 | Anti-CD3 | 70 |
|  | Anti-CD3 + CH-296 | 593 |
| 0.167 | Anti-CD3 | 104 |
|  | Anti-CD3 + CH-296 | 525 |
| 0.33 | Anti-CD3 | 272 |
|  | Anti-CD3 + CH-296 | 565 |

As shown in Table 58, even in the group in which the culture was initiated at any of cell concentrations, a high expansion fold was obtained in the group stimulated with CH-296 and the anti-CD3 antibody as compared to that of the control group (stimulation only with anti-CD3 antibody). In other words, even when the culture was initiated at various cell concentrations, the LAK cells could be clearly induced and cultured at a high expansion fold by stimulation with CH-296 and the anti-CD3 antibody as compared to that of stimulation only with the anti-CD3 antibody. In addition, the culture was carried out on the assumption of 30 mL blood collection, and 10 L of a final culture medium amount, and the expansion fold was clearly high by stimulation with CH-296 even under the conditions mentioned above, so that the effectiveness of CH-296 was found. Further, in the control group, although a case where the expansion fold was greatly fluctuated depending on the initial cell concentration at the initiation of culture was confirmed, stable expansion folds were obtained in the groups stimulated with CH-296, regardless of the initial cell concentration at the initiation of culture.

Example 59

Determination of Expansion Fold in Culture System of LAK Cells Using Low-Serum Medium (AIM V) (Stimulation Period)

The influence of the day numbers of stimulation at the initiation of culture only with the anti-CD3 antibody or with the anti-CD3 antibody and CH-296 in the culture system of LAK cells on the expansion fold was confirmed.

Each group in which the day number of stimulation was 2 days, 3 days or 4 days was set.

PBMCs which were prepared in item (1) of Example 1 were suspended in AIM V containing 3% human AB serum so as to have a concentration of 0.33×10⁶ cells/mL in each group, the suspension was then put on a plate immobilized with the anti-human CD3 antibody or a plate immobilized with the anti-human CD3 antibody and CH-296, prepared in item (1) of Example 41, in a volume of 3 mL/well each, and IL-2 was added thereto so as to have a final concentration of 1000 U/mL. These plates were incubated at 37° C. in 5% $CO_2$ (zeroth day of culture).

On the second day or the third day from the initiation of culture, the group with 2-day stimulation or the group with 3-day stimulation was transferred as it was to a fresh 12-well culture plate to which nothing was immobilized.

On the fourth day from the initiation of culture, each group was diluted with AIM V containing 1% human AB serum (amount of liquid: 6 mL) so as to have a concentration of 0.1×10⁶ cells/mL, and each dilution was transferred to a 12.5 cm² cell culture flask to which nothing was immobilized. In each group, IL-2 was respectively added thereto so as to have a final concentration of 500 U/mL.

On the seventh day from the initiation of culture, each group was diluted with AIM V containing 0.05% human AB serum (amount of liquid: 12.6 mL) so as to have a concentration of 0.45×10⁶ cells/mL, and each dilution was transferred to a fresh 25 cm² cell culture flask kept upright to which nothing was immobilized. In each group, IL-2 was respectively added thereto so as to have a final concentration of 500 U/mL.

On the tenth day from the initiation of culture, each group was diluted with AIM V containing 0.05% human AB serum (amount of liquid: 12.6 mL) so as to have a concentration of 0.6×10⁶ cells/mL, and each dilution was transferred to a fresh 25 cm² cell culture flask kept upright to which nothing was immobilized. In each group, IL-2 was respectively added thereto so as to have a final concentration of 500 U/mL.

On the fifteenth day from the initiation of culture, the number of living cells was counted by trypan blue staining method, and calculated as an expansion fold by comparing the number with of the cells the number at the initiation of culture. Each experiment was carried out twice. Each of the average results is shown in Table 59.

TABLE 59

| | Stimulation on Zeroth Day from Initiation of Culture | Expansion Fold (fold) |
|---|---|---|
| Stimulation Period: 2 days | Anti-CD3 | 266 |
| | Anti-CD3 + CH-296 | 438 |
| Stimulation Period: 3 days | Anti-CD3 | 424 |
| | Anti-CD3 + CH-296 | 562 |
| Stimulation Period: 4 days | Anti-CD3 | 257 |
| | Anti-CD3 + CH-296 | 568 |

As shown in Table 59, during the culture of LAK cells cultured for the various stimulation periods from the initiation of culture, in any groups with any stimulation period, the high expansion folds were obtained in the groups stimulated with CH-296 and the anti-CD3 antibody as compared to those of the control group (stimulation only with anti-CD3 antibody). In other words, even when the stimulation period was changed, the LAK cells could be clearly induced and cultured at a high expansion fold by stimulation with CH-296 and the anti-CD3 antibody, than that of stimulation only with the anti-CD3 antibody. In addition, the cells during this culture were in a high concentration and at a high density, and the serum concentration was on assumption of 30 mL blood collection and a total culture medium amount of 10 L and, the expansion fold was clearly high by stimulation with CH-296 even under the conditions described above, so that the effectiveness of CH-296 was found.

Example 60

Determination of Expansion Fold in Culture System of LAK Cells Using Low-Serum Medium (AIM V) (CH-296Na)

An expansion fold in the culture system of LAK cells using CH-296Na as an FN fragment was determined.

A group in which CH-296Na was immobilized to a cell culture plate, and a group in which CH-296Na was added as it was to a cell culture medium were set.

(1) Immobilization of Anti-Human CD3 Antibody and FN Fragment

An anti-human CD3 antibody and an FN fragment were immobilized to a culture equipment used in the following experiment. Concretely, 1.9 mL each of PBS containing the anti-human CD3 antibody (final concentration: 5 µg/mL) was added to a 12-well cell culture plate. Upon the addition, a fibronectin fragment (CH-296Na) described in Example 54 was added to a group with addition of an FN fragment so as to have a final concentration of 28.6 µg/mL. As a control, there was also set a group without addition of CH-296Na.

These culture equipments were incubated at room temperature for 5 hours, and stored at 4° C. until use. Immediately before use, PBS containing the anti-human CD3 antibody and CH-296Na was removed by aspiration from these culture equipments, and each well was washed twice with PBS, and once with RPMI medium. Each experiment was carried out using the culture equipment.

(2) Induction and Culture of LAK Cells

PBMCs which were prepared in item (1) of Example 1 were respectively suspended in AIM V containing 3% human AB serum so as to have a concentration of $0.33 \times 10^6$ cells/mL, and thereafter the suspension was put on a cell culture plate immobilized with the anti-human CD3 antibody or a cell culture plate immobilized with the anti-human CD3 antibody and CH-296Na, prepared in item (1) of Example 60, in a volume of 3 mL/well each. In addition, in the group in which CH-296Na was added as it was to a cell culture medium, CH-296Na was added to the cells which were put on the cell culture plate immobilized with the anti-human CD3 antibody, so as to have a final concentration of 1 µg/mL. In each group, IL-2 was added thereto so as to have a final concentration of 1000 U/mL. These plates were incubated at 37° C. in 5% $CO_2$ (zeroth day of culture).

On the fourth day from the initiation of culture, each group was diluted with AIM V containing 1% human AB serum (amount of liquid: 6 mL) so as to have a concentration of $0.1 \times 10^6$ cells/mL, and the dilution was transferred to a 12.5 $cm^2$ cell culture flask to which nothing was immobilized. In each group, IL-2 was added thereto so as to have a final concentration of 500 U/mL.

On the seventh day from the initiation of culture, each group was diluted with AIM V containing 0.05% human AB serum (amount of liquid: 12.6 mL), respectively, so as to have a concentration of $0.5 \times 10^6$ cells/mL, and each dilution was transferred to a fresh 25 $cm^2$ cell culture flask kept upright to which nothing was immobilized. In each group, IL-2 was added thereto so as to have a final concentration of 500 U/mL.

On the tenth day from the initiation of culture, each group was diluted with AIM V containing 0.05% human AB serum (amount of liquid: 12.6 mL), respectively, so as to have a concentration of $0.94 \times 10^6$ cells/mL, and each dilution was transferred to a fresh 25 $cm^2$ cell culture flask kept upright to which nothing was immobilized. In each group, IL-2 was added thereto so as to have a final concentration of 500 U/mL.

On the fifteenth day at the initiation of culture, the number of living cells was counted by trypan blue staining method, and calculated as an expansion fold by comparing the number of the cells with the number at the initiation of culture. Each experiment was carried out twice. Each of the average results is shown in Table 60.

TABLE 60

| Stimulation on Zeroth Day from Initiation of Culture | Expansion Fold (fold) |
|---|---|
| Anti-CD3 | 222 |
| Immobilized with Anti-CD3 + CH-296Na | 922 |
| Addition of Anti-CD3 + CH-296Na Solution | 651 |

As shown in Table 60, a high expansion fold was obtained in any group in which CH-296Na was immobilized or added as a solution, as compared to that of the control group (stimulation only with anti-CD3 antibody). In other words, the LAK cells could be clearly induced and cultured in a high expansion fold by stimulation with CH-296Na and the anti-CD3 antibody, as compared to that of stimulation only with the anti-CD3 antibody. Here, the culture was on the assumptions of 30 mL blood collection, and a final culture medium amount of 10 L, and the expansion fold was clearly high by stimulation with CH-296Na under the conditions as described above, so that the effectiveness of CH-296Na was found.

Example 61

Preparation of CH-296 Beads

As beads for immobilizing CH-296, Dynabeas M-450 Epoxy (manufactured by Dynal) were used. $2.8 \times 10^8$ Dynabeas M-450 Epoxy were washed three times with a 0.1 M phosphate buffer (pH 7.0). The washed $2.8 \times 10^8$ Dynabeas M-450 Epoxy were suspended in 0.7 mL of PBS containing 140 µg of CH-296, and an immobilization reaction was carried out overnight at 4° C. while gently mixing. The reaction solution was removed, and replaced three times with 0.7 mL of PBS containing 0.1% human serum albumin (HSA), and then stored at 4° C., to give CH-296 beads.

In addition, beads without containing CH-296 were treated in the same manner, to give control beads.

Example 62

Preparation of CD3/CH-296 Beads

As beads for immobilizing CH-296 and the anti-human CD3 antibody, Dynabeas M-450 Epoxy were used. $4 \times 10$ Dynabeas M-450 Epoxy were washed three times with a 0.1 M phosphate buffer (pH 7.0). The washed $4 \times 10^8$ Dynabeas M-450 Epoxy were suspended in 1 mL of PBS containing 160 µg of CH-296 and 32 µg of the anti-human CD3 antibody, and an immobilization reaction was carried out overnight at 4° C. while gently mixing. The reaction solution was removed, and replaced three times with 1 mL of PBS containing 0.1% human serum albumin (HSA), and then stored at 4° C., to give CD3/CH-296 beads.

Example 63

Determination of Expansion Fold in Culture System of LAK Cells Using Low-Serum Medium (AIM V) (Stimulation with Beads Immobilized with FNfr)

The effects on an LAK cell culture using a fibronectin fragment (CH-296) immobilized to a cell culture carrier (beads) was confirmed.

A group stimulated with the CD3 beads in which the anti-CD3 antibody was immobilized to the beads and the control beads to which nothing was immobilized (CD3 beads group), a group stimulated with the CD3 beads and the CH-296 beads in which the CH-296 was immobilized to the beads (CD3 beads+CH-296 beads group), and a group stimulated with CD3/CH-296 beads in which the anti-CD3 antibody and CH-296 were immobilized to beads (CD3/CH-296 beads group) were set.

PBMCs which were prepared in item (1) of Example 1 were suspended in AIM V containing 1% human AB serum so as to have a concentration of $0.33 \times 10^6$ cells/mL. Thereafter, the suspension was put on a 12-well culture plate to which nothing was immobilized in a volume of 3 mL/well each, so that CD3 beads (Dynabeads M-450 CD3 (panT), Bellitus, DB11113) were added thereto in an amount of $1 \times 10^6$ beads/well and control beads which were prepared in Example 61 were added thereto in an amount of $3.8 \times 10^6$ beads/well in the CD3 beads group, or that the CD3 beads were added thereto in an amount of $1 \times 10^6$ beads/well, and CH-296 beads which were prepared in Example 61 were added thereto in an amount of $0.76 \times 10^6$ beads/well in the CD3 beads+CH-296 beads group, or that CD3/CH-296 beads which were prepared in Example 62 were added thereto in an amount of $2.3 \times 10^6$ beads/well in the CD3/CH-296 beads group. IL-2 was added to each well so as to have a final concentration of 1000 U/mL. These plates were incubated at 37° C. in 5% $CO_2$ (zeroth day of culture).

On the fourth day from the initiation of culture, in each group, each of the beads contained in the culture medium was removed with a magnetic stand, and thereafter the culture medium was diluted with AIM V containing 1% human AB serum (amount of liquid: 6 mL) so as to have a concentration of $0.07 \times 10^6$ cells/mL, and the dilution was transferred to a 12.5 $cm^2$ cell culture flask to which nothing was immobilized. In each group, IL-2 was added thereto so as to have a final concentration of 500 U/mL.

On the seventh day from the initiation of culture, each group was diluted with AIM V containing 1% human AB serum (amount of liquid: 12.6 mL) so as to have a concentration of $0.25 \times 10^6$ cells/mL, and each dilution was transferred to a fresh 25 $cm^2$ cell culture flask kept upright to which nothing was immobilized. In each group, IL-2 was added thereto so as to have a final concentration of 500 U/mL.

On the tenth day from the initiation of culture, each group was diluted with AIM V containing 1% human AB serum (amount of liquid: 12.6 mL) so as to have a concentration of $0.685 \times 10^6$ cells/mL, and the dilution was transferred to a fresh 25 $cm^2$ cell culture flask kept upright to which nothing was immobilized. In each group, IL-2 was added thereto so as to have a final concentration of 500 U/mL.

On the fifteenth day from the initiation of culture, the number of living cells was counted by trypan blue staining method, and calculated as an expansion fold by comparing the number of the cells with the number at the initiation of culture. Each experiment was carried out twice. Each of the average results is shown in Table 61.

TABLE 61

|  | Stimulation on Zeroth Day from Initiation of Culture | Expansion Fold (fold) |
| --- | --- | --- |
| CD3 Beads | Anti-CD3 | 420 |
| CD3 Beads + CH-296 Beads | Anti-CD3 + CH-296 | 830 |
| CD3/CH-296 Beads | Anti-CD3 + CH-296 | 748 |

As shown in Table 61, in the LAK cell culture stimulated with each of the beads, a high expansion fold was obtained in the group stimulated in the CD3 beads+CH-296 beads group and the CD3/CH-296 beads group, as compared to that of the CD3 beads. In other words, in the culture of LAK cells using beads as a cell culture carrier, the LAK cells could be clearly induced and cultured at a high expansion fold by stimulation with the beads immobilized with CH-296 and the anti-CD3 antibody, as compared to that of stimulation with the beads immobilized only with the anti-CD3 antibody. In addition, the cells during the culture were in a high concentration and at a high density, and the expansion fold was clearly high by stimulation with CH-296 beads even under the conditions as described above, so that the effectiveness of CH-296 was found.

Example 64

Content Ratio of CD8-Positive Cells in LAK Cell Population Cultured Using Low-Serum Medium (AIM V) (Stimulation with Beads Immobilized with FNfr)

(1) Induction and Culture of LAK Cells

The induction and the culture of LAK cells were carried out in the same manner as in Example 63.
(2) Determination of Content Ratio of CD8-Positive Cell Population in LAK Cells The content ratio of the CD8-positive cells was determined in the same manner as in item (2) of Example 4. The results are shown in Table 62.

TABLE 62

| | Stimulation on Zeroth Day from Initiation of Culture | Content Ratio of CD8-Positive Cells (%) |
|---|---|---|
| CD3 Beads | Anti-CD3 | 47 |
| CD3 Beads + CH-296 Beads | Anti-CD3 + CH-296 | 49 |
| CD3/CH-296 Beads | Anti-CD3 + CH-296 | 59 |

As shown in Table 62, in the culture of LAK cells stimulated with each of the beads, the content ratio of the CD8-positive cells in LAK cells during the culture could be induced at a high level in the group stimulated in the CD3 beads+CH-296 beads group and the CD3/CH-296 beads group, as compared to that of the CD3 beads group. In other words, in the culture of LAK cells using beads as a cell culture carrier, it was clarified that the LAK cells could be clearly induced and cultured, while increasing the content ratio of the CD8-positive cells in LAK cells by stimulation with the beads immobilized with CH-296 and the anti-CD3 antibody, as compared to that of stimulation with the beads immobilized only with the anti-CD3 antibody.

Sequence Listing Free Text
SEQ ID NO: 1; Partial region of fibronectin named III-8.
SEQ ID NO: 2; Partial region of fibronectin named III-9.
SEQ ID NO: 3; Partial region of fibronectin named III-10.
SEQ ID NO: 4; Partial region of fibronectin named III-11.
SEQ ID NO: 5; Partial region of fibronectin named III-12.
SEQ ID NO: 6; Partial region of fibronectin named III-13.
SEQ ID NO: 7; Partial region of fibronectin named III-14.
SEQ ID NO: 8; Partial region of fibronectin named CS-1.
SEQ ID NO: 9; Fibronectin fragment named C-274.
SEQ ID NO: 10; Fibronectin fragment named H-271.
SEQ ID NO: 11; Fibronectin fragment named H-296.
SEQ ID NO: 12; Fibronectin fragment named CH-271.
SEQ ID NO: 13; Fibronectin fragment named CH-296.
SEQ ID NO: 14; Fibronectin fragment named C-CS1.
SEQ ID NO: 15; Fibronectin fragment named CHV-89.
SEQ ID NO: 16; Fibronectin fragment named CHV-90.
SEQ ID NO: 17; Fibronectin fragment named CHV-92.
SEQ ID NO: 18; Fibronectin fragment named CHV-179.
SEQ ID NO: 19; Fibronectin fragment named CHV-181.
SEQ ID NO: 20; Fibronectin fragment named H-275-Cys.
SEQ ID NO: 21; Primer 12S.
SEQ ID NO: 22; Primer 14A.
SEQ ID NO: 23; Primer Cys-A.
SEQ ID NO: 24; Primer Cys-S.
SEQ ID NO: 25; Fibronectin fragment named CH-296Na.
SEQ ID NO: 26; Polynucleotide coding Fibronectin fragment named CH-296Na.
SEQ ID NO: 27; Primer CH-296Na1.
SEQ ID NO: 28; Primer CH-296Na2.
SEQ ID NO: 29; Primer CH-296Na3.

Industrial Applicability

According to the process for preparing a cytotoxic lymphocyte of the present invention, there is obtained a cytotoxic lymphocyte in which expansion fold is high even when a serum-free medium or a low-serum concentration medium is used, a high cytotoxic activity is maintained, an expression level of IL-2R is significantly increased, and a ratio of a CD8-positive cell is improved. The lymphocyte is suitably used, for instance, in adoptive immunotherapy. Therefore, there is expected a great contribution of the process of the present invention to the medical field.

The invention claimed is:

1. A method for preparing cytotoxic lymphocytes comprising:
   a) culturing peripheral mononuclear cells obtained from blood in a medium containing serum and plasma at a total concentration of 0-5% by volume and IL-2, and a stimulatory composition consisting essentially of one or more recombinant fibronectin fragments and an anti-CD3 antibody, wherein said one or more fibronectin fragments are one or more polypeptides comprising an amino acid sequence selected from the group consisting of SEQ ID NOs: 1 to 20, and wherein said one or more fibronectin fragments comprise cell adhesion activity and/or heparin binding activity, wherein the cells are cultured for a total of 2 to 15 days, and wherein an antigen-presenting cell comprising antigenic peptide on its surface is not further added to the peripheral mononuclear cells or the medium, wherein the medium is contained in cell culture equipment;
   b) diluting the cell culture medium, exchanging the cell culture medium, or exchanging the cell culture equipment; and
   c) re-stimulating the cells obtained in step b) by culturing the step b) cells with a medium containing serum and plasma at a total concentration of 0-5% by volume in the presence of a stimulatory composition consisting essentially of one or more recombinant fibronectin fragments and anti-CD3 antibody added at the initiation of step c), wherein said one or more fibronectin fragments are one or more polypeptides comprising an amino acid sequence selected from the group consisting of SEQ ID NOs: 1 to 20 and IL-2,
   thereby obtaining induced and expanded cytotoxic lymphocytes.

2. The method according to claim 1, wherein the induced and expanded cytotoxic lymphocytes highly express an interleukin-2 receptor as compared to induced and expanded cytotoxic lymphocytes prepared according to claim 1 modified by practicing steps a)-c) in the absence of one or more recombinant fibronectin fragments.

3. The method according to claim 1, wherein the induced and expanded cytotoxic lymphocytes comprise CD8-positive cells in a higher ratio as compared to induced and expanded cytotoxic lymphocytes prepared according to claim 1 modified by practicing steps a)-c) in the absence of one or more recombinant fibronectin fragments.

4. The method according to claim 1, wherein a ratio of the number of cells after the expansion to the number of cells before the expansion is higher as compared to preparing cells according to claim 1 modified by practicing steps a)-c) in the absence of one or more recombinant fibronectin fragments.

5. The method according to claim 1, wherein the one or more recombinant fibronectin fragments are immobilized on a solid phase.

6. The method according to claim 5, wherein the solid phase is the cell culture equipment or a cell culture carrier.

7. The method according to claim 6, wherein the cell culture equipment is a petri dish, a flask or a bag, or the cell culture carrier is beads, a membrane or a slide glass.

8. The method according to claim 1, wherein the induced and expanded cytotoxic lymphocytes are lymphokine-activated killer cells.

9. The method according to claim 1 which is carried out in cell culture equipment, wherein the method satisfies the conditions of:
   (i) the ratio of the number of cells to the culture area in the cell culture equipment at initiation of the culture being 1 cell/cm$^2$ to 5×10$^5$ cells/cm$^2$; and/or
   (ii) the concentration of cells in the medium at initiation of culture being 1 cell/mL to 5×10$^5$ cell s/mL.

10. The method according to claim 9, wherein the method does not include a step of diluting the cell culture medium.

11. The method according to claim 1, wherein the culture conditions immediately after b) satisfy the conditions of:
    (i) the concentration of cells in the cell culture solution being 2×10$^5$ cells/mL to 1×10$^8$ cells/mL; or
    (ii) the ratio of the number of cells in the cell culture solution to the culture area in the cell culture equipment being 1×10$^5$ cells/cm$^2$ to 1×10$^8$ cells/cm$^2$.

12. The method according to claim 1, wherein the total concentration of serum and plasma in the medium immediately after step b) is the same as the total concentration of serum and plasma in the medium at initiation of the culture or lowered as compared to that at initiation of the culture.

13. The method according to claim 1, further comprising a step of transducing a foreign gene into the cytotoxic lymphocytes.

14. The method according to claim 13, wherein the foreign gene is transduced using a retrovirus, adenovirus, adeno-associated virus or simian virus.

15. The method according to claim 1, wherein after step c) the medium of step c) is further diluted, the medium of step c) is exchanged with new medium, or the cells obtained from step c) are exchanged in a further cell culture equipment.

16. The method according to claim 15, wherein the culture conditions immediately after step b) satisfy the following conditions:
    (i) the concentration of cells in the cell culture solution is 2×10$^5$ cells/mL to 1×10$^8$ cells/mL; or
    (ii) the ratio of the number of cells in the cell culture solution to the culture area in the cell culture equipment being 1×10$^5$ cells/cm$^2$ to 1×10$^8$ cells/cm$^2$.

17. The method according to claim 15, wherein the total concentration of serum and plasma in the medium immediately after step b), or immediately after step c), is the same or lower than the total concentration of serum and plasma in the medium at initiation of the culture.

18. The method according to claim 1, further comprising step d) in which the cells of step c) are transferred to a third cell culture equipment without the stimulatory composition.

* * * * *